US012797559B2

(12) United States Patent
Diaz et al.

(10) Patent No.: US 12,797,559 B2
(45) Date of Patent: Nov. 17, 2026

(54) INJECTION SYSTEM AND METHOD

(71) Applicant: CREDENCE MEDSYSTEMS, INC., Menlo Park, CA (US)

(72) Inventors: Stephen H. Diaz, Palo Alto, CA (US); John Robert Lund, Los Altos, CA (US); Gary Steese-Bradley, San Jose, CA (US); Alan E. Shluzas, San Carlos, CA (US); Jeff Tillack, Foster City, CA (US)

(73) Assignee: CREDENCE MEDSYSTEMS, INC., Menlo Park, CA (US)

( * ) Notice: Subject to any disclaimer, the term of this patent is extended or adjusted under 35 U.S.C. 154(b) by 367 days.

(21) Appl. No.: 18/377,601

(22) Filed: Oct. 6, 2023

(65) Prior Publication Data

US 2024/0115801 A1 Apr. 11, 2024

Related U.S. Application Data

(60) Provisional application No. 63/414,055, filed on Oct. 7, 2022.

(51) Int. Cl.
*A61M 5/32* (2006.01)
*A61M 5/31* (2006.01)

(52) U.S. Cl.
CPC ........ *A61M 5/3293* (2013.01); *A61M 5/3134* (2013.01); *A61M 2005/3128* (2013.01)

(58) Field of Classification Search
CPC .. A61M 2005/1787; A61M 2005/3128; A61M 5/3293; A61M 5/3134; A61M 5/31596
See application file for complete search history.

(56) References Cited

U.S. PATENT DOCUMENTS

| | | | |
|---|---|---|---|
| 3,091,240 | A | 5/1963 | Mcconnaughey |
| 5,704,918 | A | 1/1998 | Higashikawa |

(Continued)

FOREIGN PATENT DOCUMENTS

| | | |
|---|---|---|
| AU | 8156494 | 2/1995 |

OTHER PUBLICATIONS

PCT International Search Report and Written Opinion for International Appln. No. PCT/US2023/034647, Applicant Credence Medsystems, Inc., dated Feb. 7, 2024.

(Continued)

*Primary Examiner* — William H Rodriguez
(74) *Attorney, Agent, or Firm* — Vista IP Law Group, LLP

(57) ABSTRACT

An injection system includes an injection system body defining a proximal opening at a proximal end thereof and a distal needle interface at a distal end thereof. The system also includes proximal and distal stopper members disposed in the injection system body, forming a proximal drug and a distal drug chamber. The system further includes a plunger member configured to insert the proximal stopper member relative to the injection system body. Moreover, the system includes a valve forming an openable barrier between the distal needle interface and the distal drug chamber. The valve includes an outer member including a distal diaphragm, and an inner member. The distal diaphragm is configured to elastically deform distally away from the inner member with increased pressure in the distal drug chamber to allow flow from the distal drug chamber to the distal needle interface.

18 Claims, 42 Drawing Sheets

(56) References Cited

U.S. PATENT DOCUMENTS

| | | | | |
|---|---|---|---|---|
| 9,850,058 | B2 * | 12/2017 | Kolonia | A61M 5/31 |
| 11,116,905 | B2 * | 9/2021 | Diaz | A61M 5/19 |
| 2012/0265171 | A1 * | 10/2012 | Thorne, Jr. | A61M 5/19 604/207 |
| 2019/0117901 | A1 * | 4/2019 | Szapiro | A61M 5/31505 |
| 2020/0268973 | A1 * | 8/2020 | Tillack | A61J 1/062 |
| 2020/0398000 | A1 * | 12/2020 | Diaz | A61M 5/19 |
| 2021/0402094 | A1 | 12/2021 | Diaz | |
| 2023/0181832 | A1 | 6/2023 | Kulkarni et al. | |
| 2023/0248913 | A1 * | 8/2023 | Diaz | A61M 5/3294 604/181 |
| 2024/0173479 | A1 * | 5/2024 | Konana Thippeswamy | A61M 5/178 |
| 2024/0285860 | A1 * | 8/2024 | Sadleir | A61M 5/16827 |
| 2025/0229036 | A1 * | 7/2025 | Malviya | A61M 5/31596 |
| 2025/0262383 | A1 * | 8/2025 | Diaz | A61M 5/3202 |

OTHER PUBLICATIONS

Foreign Examination Report for EP Patent Appln. No. 23 800 646.4, dated Jan. 27, 2026.
Foreign Response for EP Patent Appln. No. 23800646.4 dated May 27, 2026.
Foreign Examination Report for EP Patent Appln. No. 23 800 646.4 dated Aug. 14, 2026.

* cited by examiner

PRIOR ART

INJECTION SYSTEM AND METHOD

The present application claims priority to U.S. Provisional Patent Application Ser. No. 63/414,055, filed on Oct. 7, 2022 under entitled "INJECTION SYSTEM AND METHOD." This application includes subject matter similar to the subject matter described in the following co-owned U.S. patent applications: (1) U.S. Utility patent application Ser. No. 14/321,706, filed Jul. 1, 2014 and issued as U.S. Utility Pat. No. 9,814,842 on Nov. 14, 2017 under entitled "SAFETY SYRINGE"; (2) U.S. Utility patent application Ser. No. 14/543,787, filed Nov. 17, 2014 and issued as U.S. Utility Pat. No. 10,300,217 on May 28, 2019 under entitled "SYSTEM AND METHOD FOR DRUG DELIVERY WITH A SAFETY SYRINGE"; (3) U.S. Utility patent application Ser. No. 14/696,342, filed Apr. 24, 2015, and issued as U.S. Utility Pat. No. 10,010,677 on Jul. 7, 2018 under entitled "SYSTEM AND METHOD FOR SAFETY SYRINGE"; (4) U.S. Utility patent application Ser. No. 15/801,239, filed on Nov. 1, 2017 and issued as U.S. Utility Pat. No. 10,926,038 on Feb. 23, 2021 under entitled "SYSTEM AND METHOD FOR SAFETY SYRINGE"; (5) U.S. Utility patent application Ser. No. 15/801,259, filed on Nov. 1, 2017, and issued as U.S. Utility Pat. No. 10,864,330 on Dec. 15, 2020 under entitled "SYSTEM AND METHOD FOR SAFETY SYRINGE"; (6) U.S. Utility patent application Ser. No. 15/801,281 filed on Nov. 1, 2017 and issued as U.S. Utility Pat. No. 10,912,894 on Feb. 9, 2021 under entitled "CARTRIDGE SAFETY INJECTION SYSTEM AND METHODS"; (7) U.S. Utility patent application Ser. No. 15/801,304 filed on Nov. 1, 2017 and issued as U.S. Utility Pat. No. 10,960,144 on Mar. 30, 2021 under entitled "SYSTEM AND METHOD FOR SAFETY SYRINGE"; (8) U.S. patent application Ser. No. 16/798,188, filed on Feb. 21, 2020 under entitled "SYSTEM AND METHOD FOR SAFETY SYRINGE"; (9) U.S. Utility patent application Ser. No. 16/435,429 filed on Jun. 7, 2019 under entitled "SYSTEM AND METHOD FOR SAFETY SYRINGE"; (10) U.S. Utility patent application Ser. No. 16/837,835, filed Apr. 1, 2020 under entitled "POLYMERIC INJECTION SYSTEMS"; (11) U.S. patent application Ser. No. 16/908,531 filed on Jun. 22, 2020 under entitled "INJECTION SYSTEM AND METHOD"; (12) U.S. Provisional Patent Application Ser. No. 62/904,988 filed on Sep. 24, 2019 under entitled "SYSTEM AND METHOD FOR SAFETY SYRINGE"; (13) U.S. Provisional Patent Application Ser. No. 63/094,313 filed on Oct. 20, 2020 under entitled "RETRACTION MECHANISM FOR SAFE INJECTION SYSTEM"; (14) U.S. Provisional Patent Application Ser. No. 62/682,381, filed on Jun. 8, 2018 under entitled "SYSTEM AND METHOD FOR SAFETY SYRINGE"; (15) U.S. Provisional Patent Application Ser. No. 62/729,880, filed on Sep. 11, 2018 under entitled "SYSTEM AND METHOD FOR SAFETY SYRINGE"; (16) U.S. Provisional Patent Application Ser. No. 63/094,313 filed on Oct. 20, 2020 under entitled "RETRACTION MECHANISM FOR SAFE INJECTION SYSTEM"; (17) U.S. Provisional Patent Application Ser. No. 63/046,517, filed on Jun. 30, 2020 under entitled "SYSTEM AND METHOD FOR SAFETY SYRINGE"; (18) U.S. Provisional Patent Application Ser. No. 63/156,264, filed on Mar. 3, 2021 under entitled "SYSTEM AND METHOD FOR SAFETY SYRINGE"; (19) U.S. Provisional Patent Application Ser. No. 63/193,466, filed on May 26, 2021 under entitled "SYSTEM AND METHOD FOR SAFETY SYRINGE"; and U.S. Provisional Patent Application Ser. No. 63/300,394, filed on Jan. 18, 2022 under entitled "INJECTION SYSTEM AND METHOD". The contents of the applications and patents identified herein are fully incorporated herein by reference as though set forth in full.

FIELD OF THE DISCLOSURE

The present disclosure relates generally to injection systems, devices, and processes for facilitating various levels of control over fluid infusion, and more particularly to systems and methods related to multiple chamber injection systems, with or without safety features, in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling. The use of needle injection configurations, on the other hand, carries with it the risk of a sharp needle contacting or stabbing a person or structure that is not desired. For this reason, so called "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possibly malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for prefilled syringe assemblies such as those depicted in FIGS. 5A and 5B, which generally comprise a syringe body, or “drug enclosure containment delivery system”, (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating (e.g., polytetrafluoroethylene (“PTFE”)), to facilitate preferred sealing and relative motion characteristics against the associated syringe body structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a “clipped flange” while the other is known as a “full flange.” The flange is used to grasp the syringe with the fingers to provide support for pushing on the plunger to give the injection. The syringe body (34) preferably comprises a translucent material such as a glass or polymer and/or a combination thereof. To form a contained volume within the chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross-sectional shape may establish a seal against the syringe body (34)), or be configured to have other cross-sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more “vertical” solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

In some cases, multi-component injection systems may mix injectable components (e.g., liquids and/or powders) before injection. Some systems utilize a single injection device to draw a component liquid from one container and inject the liquid component into another container to solubilize the dry component therein. The solubilized dry component is then drawn into the injection device for injection into a patient. Such systems require much handling of unsheathed needles, leading to unnecessary exposure of a user to one or more uncapped needles. Further, manually transferring the liquid component from one container to another can result in incomplete transfer of the liquid component and affect the ratio of the components in the final mixed injectable. Moreover, accessing and manipulating multiple containers of components complicates the injection process, thereby increasing the risk of user error. Accordingly, there exists a need for multi-component injection systems that simplify the manual accessing and mixing of multiple components from multiple containers.

These limitations are addressed by multiple chamber injection systems configured to mix and inject multiple components as disclosed in U.S. patent application Ser. Nos. 14/696,342, 15/801,259, and 63/300,394, which were previously incorporated by reference herein. However, there remains a need for precise control of multiple chamber injection systems for accurate handling, mixing, and delivery of multi-component injectables.

In addition, an increasing number of injectable liquids (e.g., medicines) have yet another requirement that time of exposure of the injectable liquid to metals (e.g., stainless steel of a needle) be minimized.

It is also desirable to incorporate needle stick prevention technology into the injection system. The ability to retract the sharp end of the needle at least partially inside of the syringe protects the person giving the injection and the patient from inadvertent needle stick injuries.

There is a need for injection systems which address the shortcomings of currently-available configurations. In particular, there is a need for multiple chamber safety injection solutions with precise control, which may utilize the existing and relatively well-controlled supply chain of conventionally delivered prefilled syringe assemblies such as those described in reference to FIGS. 5A and 5B.

SUMMARY

Embodiments are directed to injection systems. In particular, the embodiments are directed to multiple chamber safe injection systems with precise control of handling, mixing, and delivery of multi-component injectables.

In one embodiment, an injection system includes an injection system body defining a proximal opening at a proximal end thereof and a distal needle interface at a distal end thereof. The system also includes proximal and distal stopper members disposed in the injection system body, forming a proximal drug chamber between the proximal and distal stopper members and a distal drug chamber between the distal stopper member and the distal end of the injection system body. The system further includes a plunger member configured to insert the proximal stopper member relative to the injection system body. Moreover, the system includes a valve forming an openable barrier between the distal needle interface and the distal drug chamber. The valve includes an outer member including a distal diaphragm which defines a distal opening therein. The valve also includes an inner member including a distally extending member configured to fit in and interfere with the distal opening in the distal diaphragm when the distally extending member is disposed in the distal opening in the distal diaphragm. The distal diaphragm is configured to elastically deform distally away from the inner member with increased pressure in the distal drug chamber to allow flow from the distal drug chamber to the distal needle interface.

In one or more embodiments, the distal diaphragm is biased in a closed configuration in which the distal diaphragm is disposed against the inner member to position the distal opening in the distal diaphragm around the distally extending member of the inner member unless the distal diaphragm is deformed in an open configuration in which the distal diaphragm is disposed away from the inner member. The distal diaphragm may be configured to convert from the closed configuration to the open configuration when a pressure in the distal drug chamber is equal to or greater than approximately 10 psi. When the distal diaphragm is in the open configuration, the distal diaphragm may exert minimal resistance on fluid flow from the distal drug chamber through the distal opening in the distal diaphragm to the distal needle interface.

In one or more embodiments, the outer member further includes a plurality of radially outward annular members configured to form a fluid-tight seal between the outer member and an inner surface of the injection system body. At least one pair of longitudinally adjacent radially outward annular members of the plurality of radially outward annular members may define a space therebetween. The outer member may further include a distally extending ring configured to provide a space for the distal diaphragm to deform distally to convert from the closed configuration to the open configuration.

In one or more embodiments, the outer member defines an annular groove configured to secure the inner member in the outer member. The inner member may define an annular groove, and the outer member may further include a radially inward annular member configured to interfere with the annular groove in the inner member to secure the inner member in the outer member. The inner member may define a proximal opening, and the distal diaphragm may interfere with fluid flow through with the proximal opening when the distal diaphragm is in the closed configuration. The outer member may be formed from a deformable material, and the inner member may be formed from a rigid material.

In one or more embodiments, the system further includes a needle member removably coupled to the distal needle interface. The inner member may define an outer proximally extending cylindrical member, and the outer member may define an inner proximally extending cylindrical member disposed coaxially around a portion of the needle and at least partially coaxially within the outer proximally extending cylindrical member. The outer member may further include a distally facing funnel disposed adjacent the distal opening in the distal diaphragm.

In another embodiment, an injection system includes an injection system body defining a proximal opening at a proximal end thereof and a distal needle interface at a distal end thereof. The system also includes proximal and distal stopper members disposed in the injection system body, forming a proximal drug chamber between the proximal and distal stopper members and a distal drug chamber between the distal stopper member and the distal end of the injection system body. The system further includes a plunger member configured to insert the proximal stopper member relative to the injection system body. Moreover, the system includes a needle member removably coupled to the distal needle interface and having a middle opening disposed adjacent a distal end of the syringe body. In addition, the system includes a valve forming an openable barrier between the middle opening and the distal drug chamber. The valve includes an elastic diaphragm defining a diaphragm opening therein and disposed around the needle member adjacent the middle opening therein. The valve also includes a seal around the diaphragm opening configured to prevent fluid flow from the distal drug chamber through the middle opening of the needle member when the elastic diaphragm is in a closed configuration. The elastic diaphragm is configured to elastically deform into an open configuration with increased pressure in the distal drug chamber to move the seal distally relative to the needle member to allow flow from the distal drug chamber through the middle opening of the needle member.

In one or more embodiments, the elastic diaphragm is biased in the closed configuration in which the seal is disposed around the needle member proximal of the middle opening unless the elastic diaphragm is deformed into the open configuration in which the elastic diaphragm is disposed at least partially distal of the middle opening. The elastic diaphragm may be configured to convert from the closed configuration to the open configuration when a pressure in the distal drug chamber is equal to or greater than approximately 10 psi. When the elastic diaphragm is in the open configuration, the elastic diaphragm may exert minimal resistance on fluid flow from the distal drug chamber through the distal opening in the elastic diaphragm to the distal needle interface.

In one or more embodiments, the valve further includes a plurality of radially outward annular members configured to form a fluid-tight seal between the valve and an inner surface of the injection system body. At least one pair of longitudinally adjacent radially outward annular members of the plurality of radially outward annular members may define a space therebetween. The valve may further include a distally extending ring configured to provide a space for the elastic diaphragm to deform distally to convert from the closed configuration to the open configuration. The valve may further include a distally facing funnel disposed adjacent the diaphragm opening. The valve may be formed from a deformable material.

In one or more embodiments, the valve further includes a distally extending support member disposed adjacent the diaphragm opening. The distally extending support member may be configured to elastically deform into a shortened configuration from a normal configuration with increased pressure in the distal drug chamber to allow the diaphragm to deform into the open configuration to move the seal distally relative to the fluid conveying member to allow flow from the distal drug chamber through the middle opening of the fluid conveying member. The distally extending support member may be configured to return to the normal configuration from the shortened configuration with normal pressure in the distal drug chamber.

In yet another embodiment, an injection system includes an injection system body defining a proximal opening at a proximal end thereof and a distal needle interface at a distal end thereof. The system also includes a stopper member disposed in the injection system body, forming a drug chamber between the stopper member and the distal end of the injection system body. The system further includes a plunger member configured to insert the stopper member relative to the injection system body. Moreover, the system includes a needle hub assembly coupled to the distal needle interface. The needle hub assembly includes a needle hub coupled to the distal needle interface, and a needle member removably coupled to the needle hub and having a middle opening disposed adjacent the distal end of the injection system body. In addition, the system includes a valve forming an openable barrier between the middle opening and the drug chamber, the valve comprising an elastic diaphragm having an circumferentially inward facing surface defining a diaphragm opening therein and disposed around the needle member proximal of the middle opening therein. The circumferentially inward facing surface is configured to form a seal around the with the needle member to prevent fluid flow from the drug chamber to the middle opening of the needle member when the elastic diaphragm is in a closed configuration. The elastic diaphragm is configured to elastically deform into an open configuration with increased pressure in the drug chamber to deform the elastic diaphragm distally relative to the needle member to move the circumferentially inward facing surface away from the needle member to allow flow from the drug chamber to the middle opening of the needle member.

In one or more embodiments, the needle member is made from a metal.

In still another embodiment, an injection system includes an injection system body defining a proximal opening at a proximal end thereof and a distal needle interface at a distal end thereof. The system also includes a stopper member disposed in the injection system body, forming a drug chamber between the stopper member and the distal end of the injection system body. The system further includes a plunger member configured to insert the stopper member relative to the injection system body. Moreover, the system includes a valve forming an openable barrier between the distal needle interface and the drug chamber. The valve includes a diaphragm defining a diaphragm opening therein, and a plug member configured to fit in the diaphragm opening. The plug member is configured to interfere with the diaphragm opening when the diaphragm is in a closed configuration and the plug member is disposed in the diaphragm to form the openable barrier between the distal needle interface and the drug chamber. The diaphragm is configured to elastically deform into an open configuration with increased pressure in the drug chamber to deform the elastic diaphragm distally away from the stopper member to allow the plug member to separate from the diaphragm to allow flow from the drug chamber to the distal needle interface.

In one or more embodiments, the plug member is made from a metal. The plug member may include a smaller radius portion disposed longitudinally between proximal and distal larger radius portions.

The aforementioned and other embodiments of the invention are described in the Detailed Description which follows.

Figure 1A:
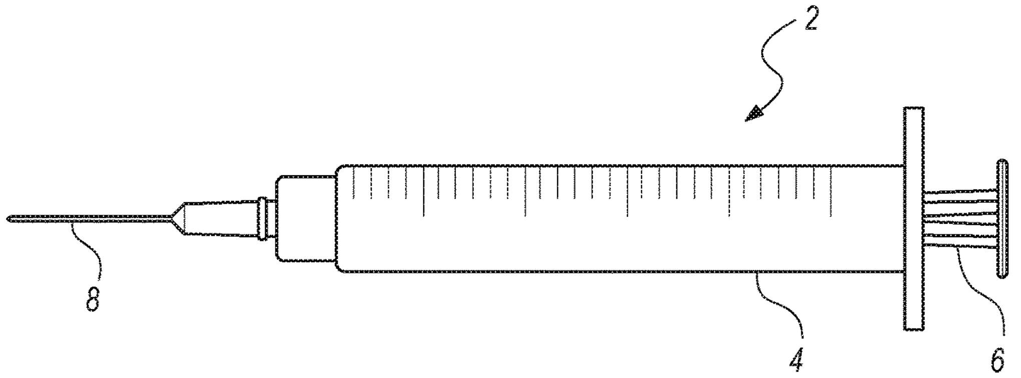
FIG. 1A PRIOR ART
FIGS. 1A to 5C illustrate various aspects of conventional injection syringe configurations.
Figure 1B:
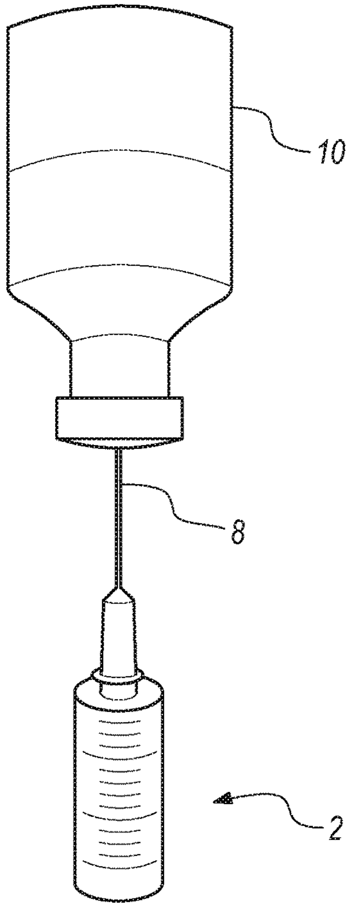
FIG. 1B PRIOR ART
Figure 2A:
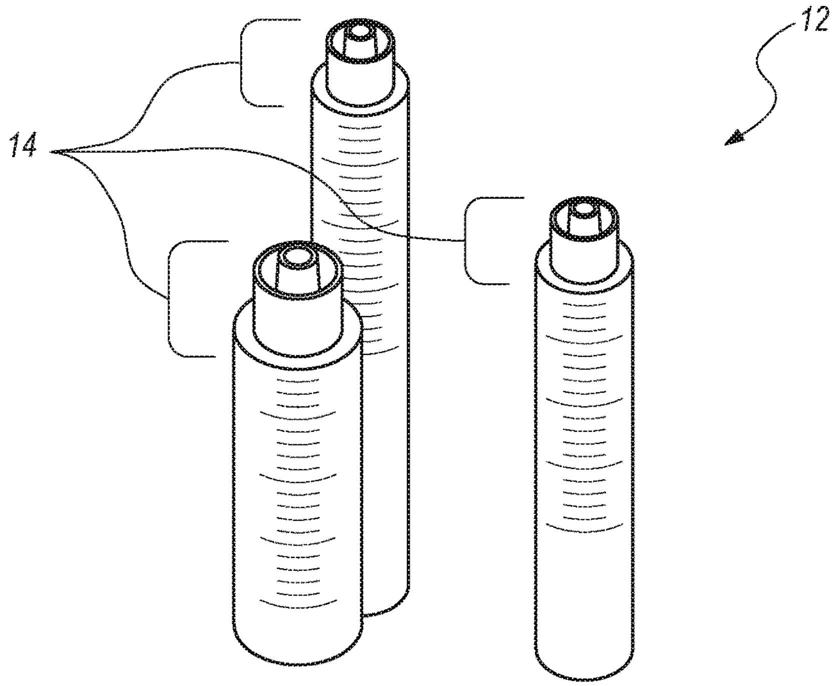
FIG. 2A PRIOR ART
Figure 2B:
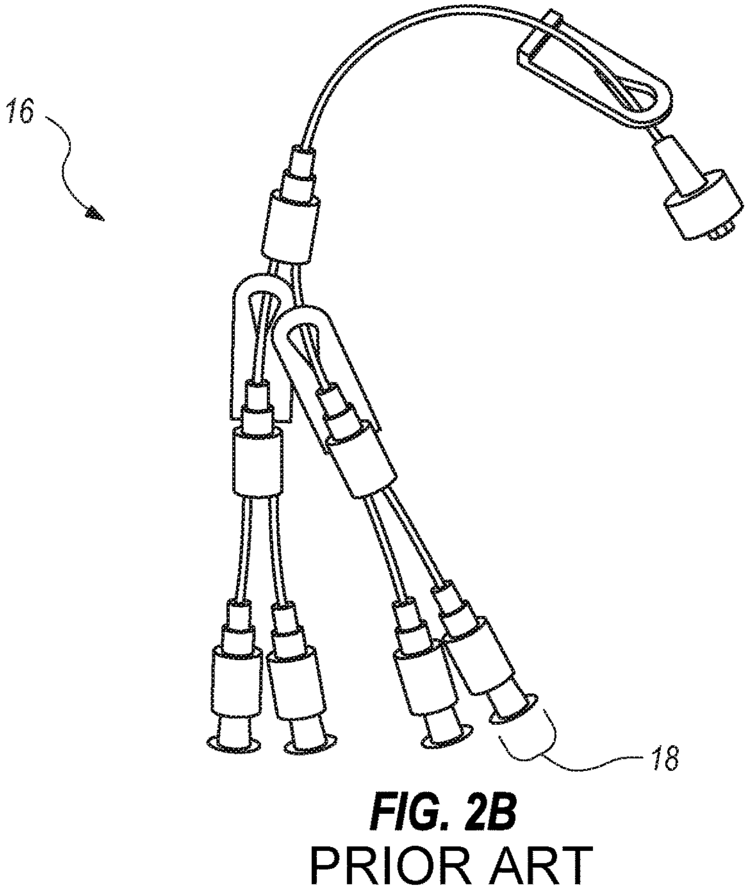
FIG. 2B PRIOR ART
Figure 3:
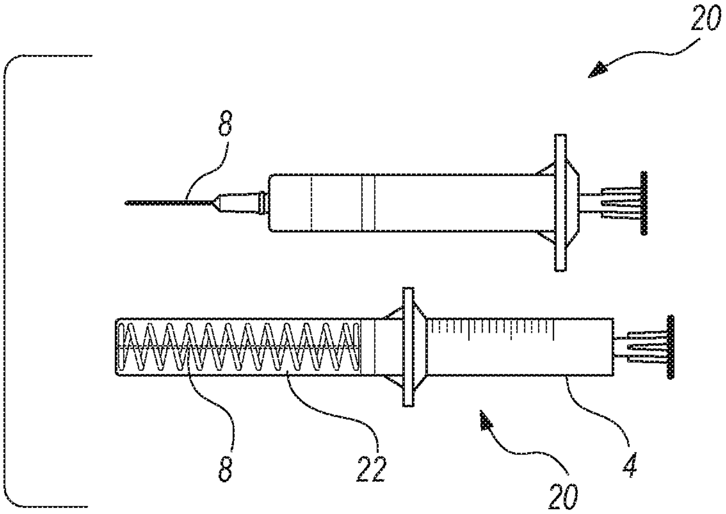
Figure 4A:
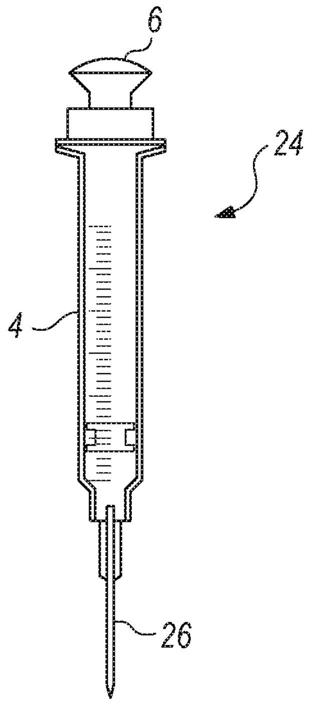
FIG. 4A PRIOR ART
Figure 4B:
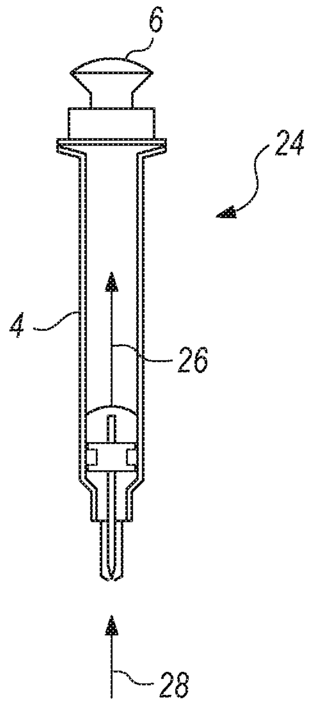
FIG. 4B PRIOR ART
Figure 5A:
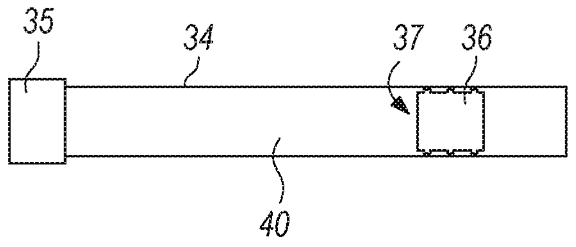
FIG. 5A PRIOR ART
Figure 5B:
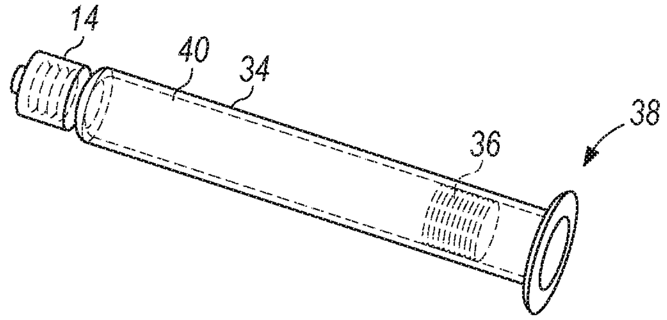
FIG. 5B PRIOR ART
Figure 5C:
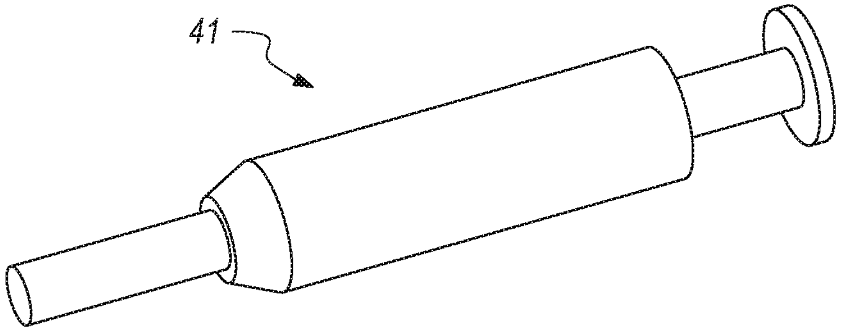
FIG. 5C PRIOR ART

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Prefilled Dual Chamber Safe Injection Systems

Exemplary Dual Chamber Safe Syringe Systems

Figure 6A:
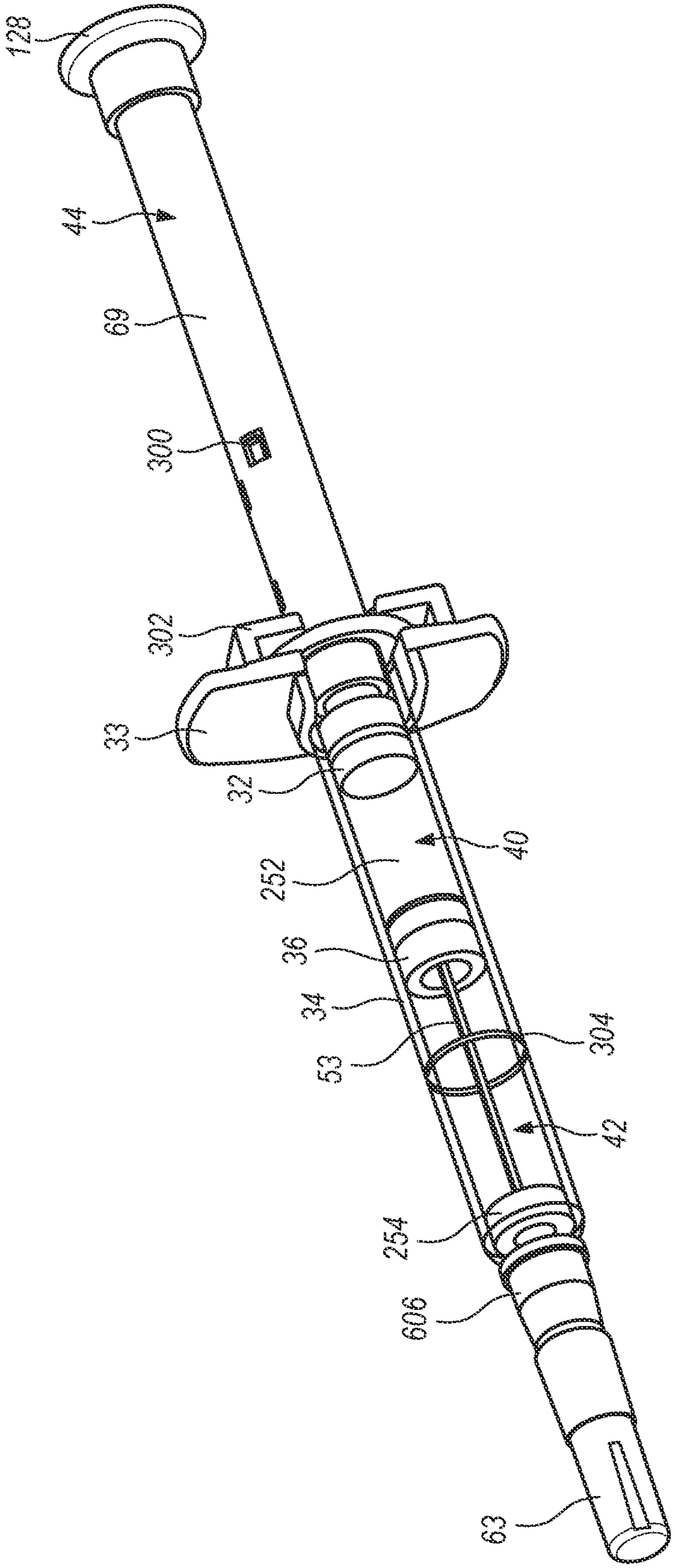
FIGS. 6A and 6B are perspective and longitudinal cross-sectional views illustrating various aspects of syringe based dual chamber safe injection systems wherein a distal needle end/tip may be withdrawn into a protected configuration after use according to some embodiments.
Figure 6B:
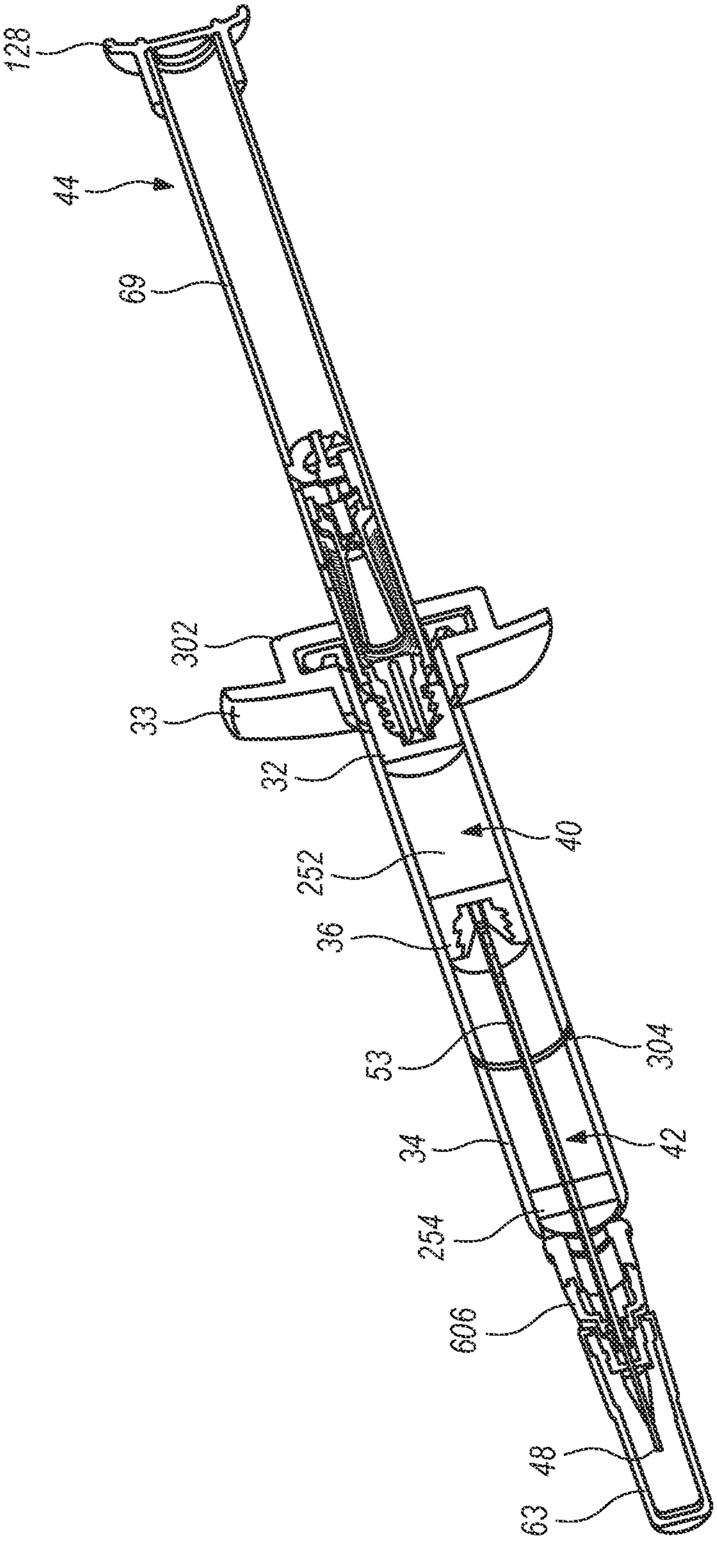

Referring to FIGS. 6A-6B, a perspective and a longitudinal cross-sectional view of a dual chamber safe injection system are shown, with a conventional off-the-shelf pre-filled syringe body (34) with conventional proximal and distal stopper members (32, 36) disposed therein. The proximal and distal stopper members (32, 36) together with the syringe body (34) define proximal and distal medicine chambers (40, 42). The proximal and distal stopper members (36, 37) occlude the proximal and distal ends of the proximal medicine chamber (40). The distal stopper member (36) occludes a proximal end of the distal medicine chamber (42). A needle coupling assembly (606) is disposed at the distal end of the distal medicine chamber (42) with a needle cover member (63) installed for storage. The dual chamber safe injection system controls transfer of a first medicine component from the proximal medicine chamber (40) to the distal medicine chamber (42) and exit of a mixed/combined medicine from the distal medicine chamber (42) distally subject to sequential insertion of a plunger member (44) relative to the syringe body (34) to various degrees by a user. The plunger member (44) includes the proximal stopper member (32), a plunger housing member (69) and a plunger manipulation interface (128). The first medicine component (252) located in the proximal medicine chamber (40) may be a liquid such as aqueous or oil based medicine solutions, a gel, or the first medicine component may be a diluent for mixing with the second medicine component (254) in the distal medicine chamber (42). The second medicine component (254) in the distal medicine chamber (42) may be a dry form medicine such as a powder, microspheres, emulsion, lyophilized or freeze dried medicine, or a cake like solid medicine.

In some embodiments, the plunger member (44) may be configured to be manually manipulated to insert the proximal stopper member (44) relative to the syringe body (34). In some embodiments, the plunger member (44) may be configured to be inserted using a spring or a motor of an injection device such as an auto injector. In some embodiments, the plunger member (44) may be configured to be inserted using a pen injection system.

The dual chamber safe injection system has a staked needle configuration wherein upon presentation to the user, a needle assembly, comprising a needle coupling assembly (606), a needle distal end/tip (48), a needle joining member, and a needle proximal end (53) are mounted in position ready for injection after removal of a needle cover member (63) which may comprise an elastomeric sealing material on its internal surface to interface with the needle distal end (48) or the distal housing portion (610) during storage. Alternatively, the needle cover member (63) may comprise a vent (not shown) for allowing pressure resulting from the transfer and mixing of the medicine components to escape from inside the syringe body (34) while preventing contamination from entering the syringe body (34). While, the staked needle is depicted as mounted in position, the staked needle may be removably coupled to the syringe body (34) using a Luer interface (not shown), with the needle proximal end (53) of the needle member extending through the Luer interface and into the distal medicine chamber (42). In the embodiments depicted in FIGS. 6A-7P, a significant portion of the safe needle retraction hardware resides within a plunger housing (69).

The dual chamber safe injection system (100) has a staked needle configuration wherein upon presentation to the user, a needle assembly, including a needle spine assembly ("needle") (76) and a needle coupling assembly (606) are mounted in position ready for injection after removal of a needle cover member (63) which may comprise an elastomeric sealing material on its internal surface to interface with a needle distal end (78) and/or a distal housing portion during storage. Alternatively, the needle cover member (63) may comprise a vent (not shown) for allowing pressure resulting from the transfer of the first medicine component/diluent (252) to escape from inside the syringe body (34) while preventing contamination from entering the syringe body (34). While, the staked needle is depicted as mounted in position, the staked needle may be removably coupled to the syringe body (34) using a Luer slip or a Luer lock interface (not shown), with the needle proximal end (53) of the needle member extending through the Luer interface and into the distal chamber (42). Alternatively, the needle may be fixedly or removably mounted to the flange on a cartridge body instead of a syringe. Such cartridge injection systems are disclosed in U.S. Utility patent application Ser. No. 15/801,281, which was previously incorporated by reference herein. In the embodiments depicted in FIGS. 6A and 6B, a significant portion of the safe needle retraction hardware resides within a plunger housing (69).

Figure 7A:
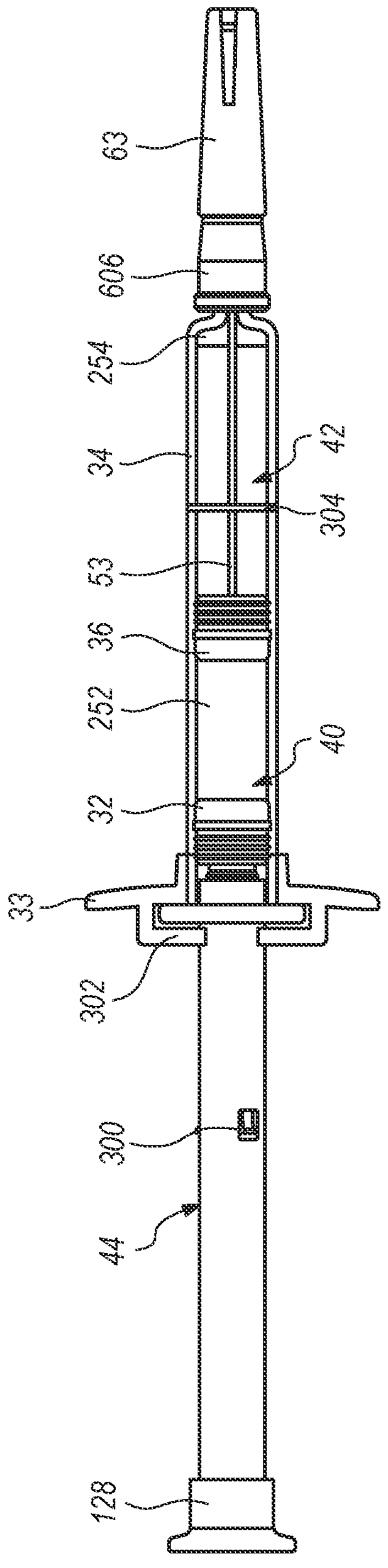
FIGS. 7A to 7P are side and longitudinal cross-sectional views illustrating various aspects of syringe based dual chamber safe injection systems during steps in methods for mixing and injecting using same according to some embodiments.
Figure 7B:
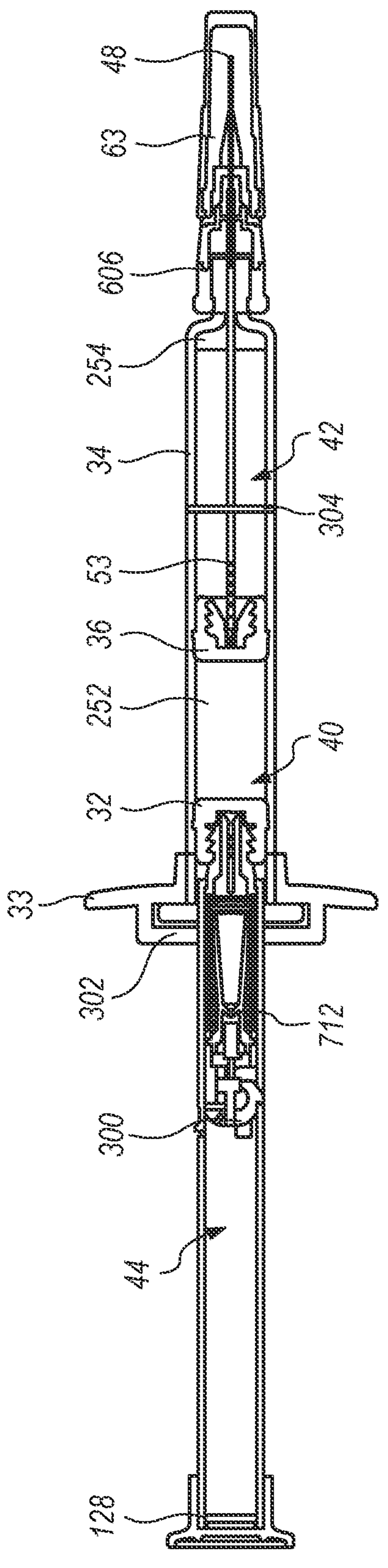
Figure 7C:
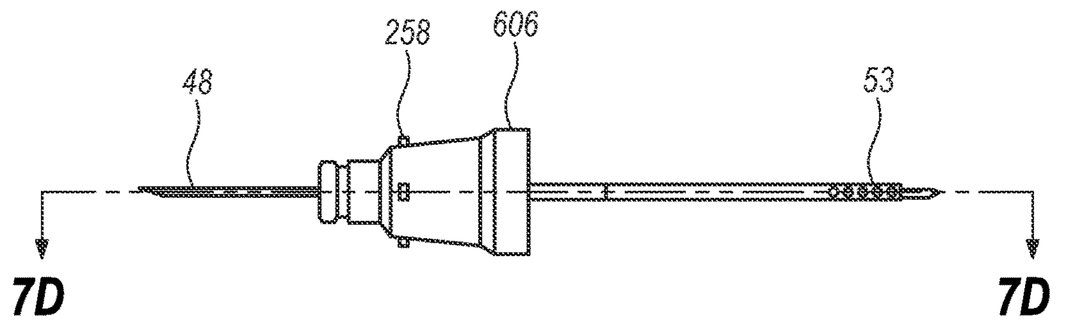
Figure 7D:
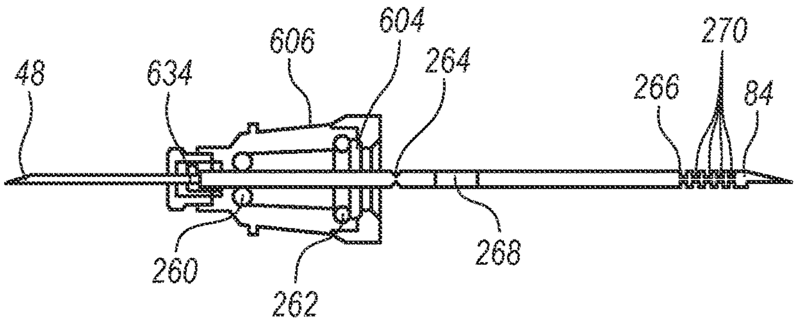
Figure 7E:
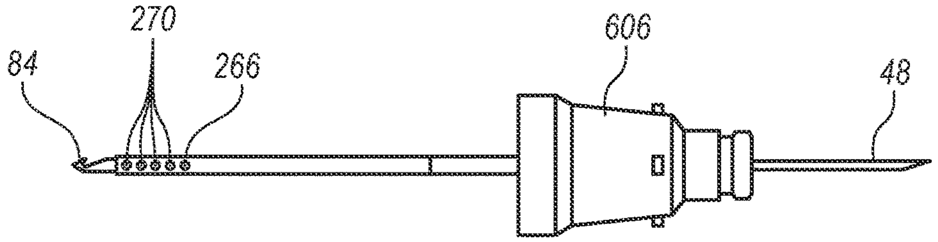
Figure 7F:
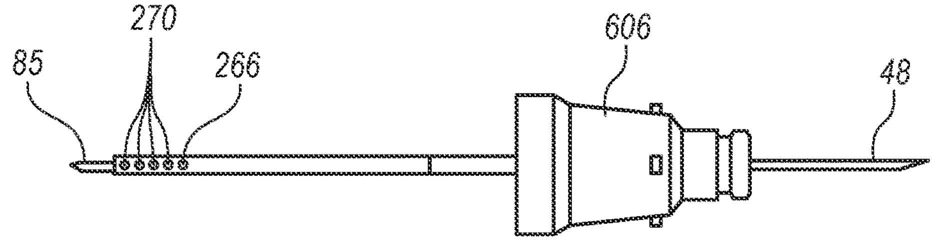
Figure 7G:
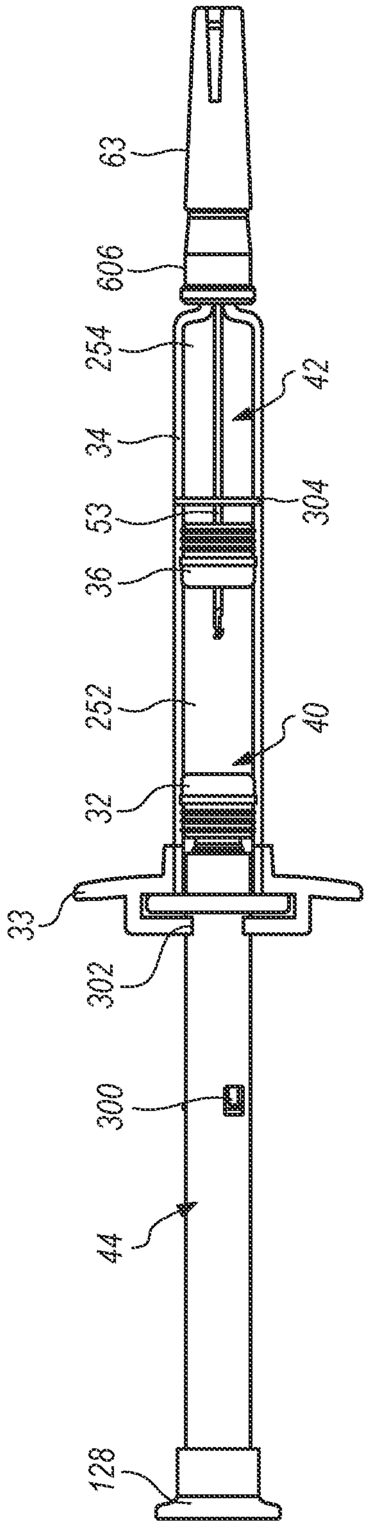
Figure 7H:
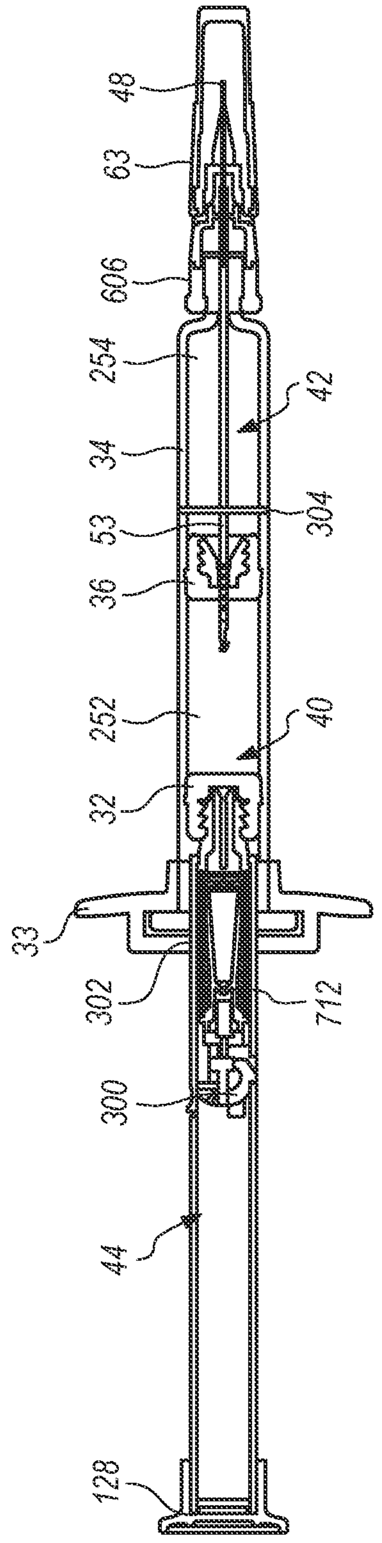
Figure 7I:
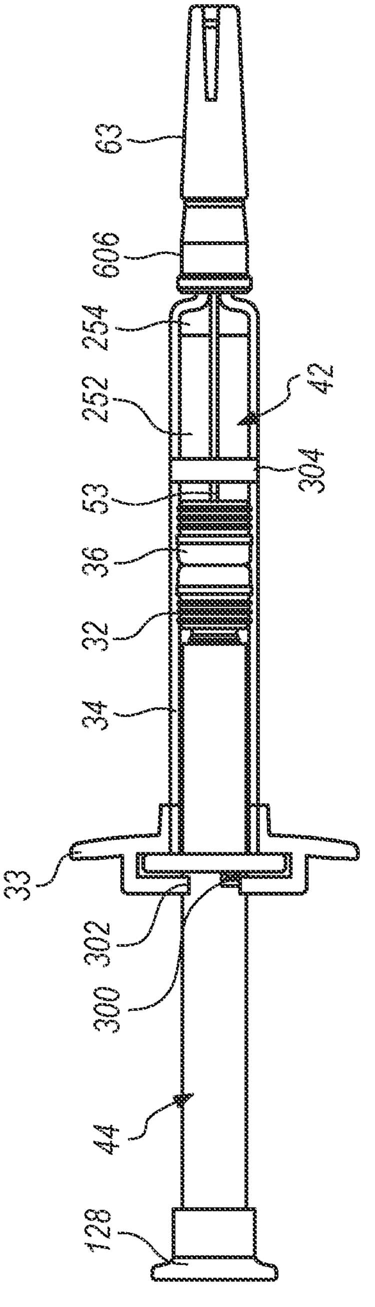
Figure 7J:
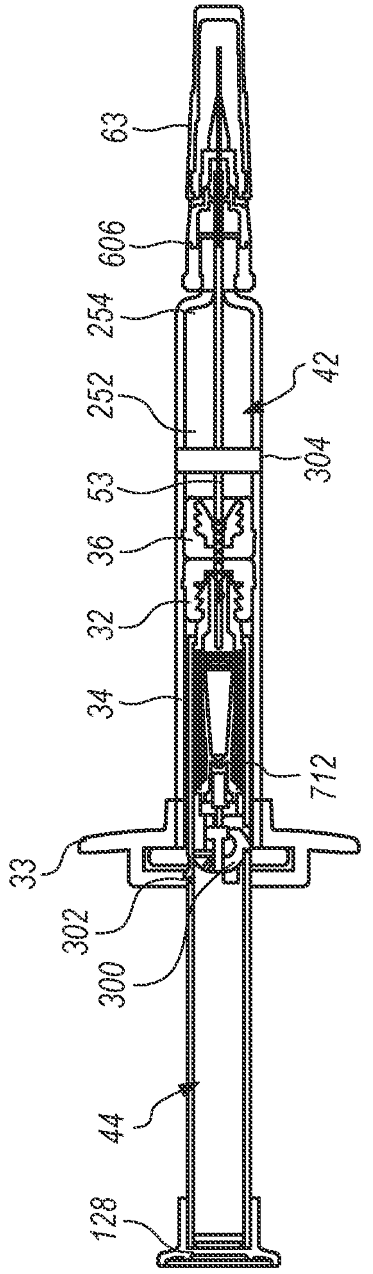
Figure 7K:
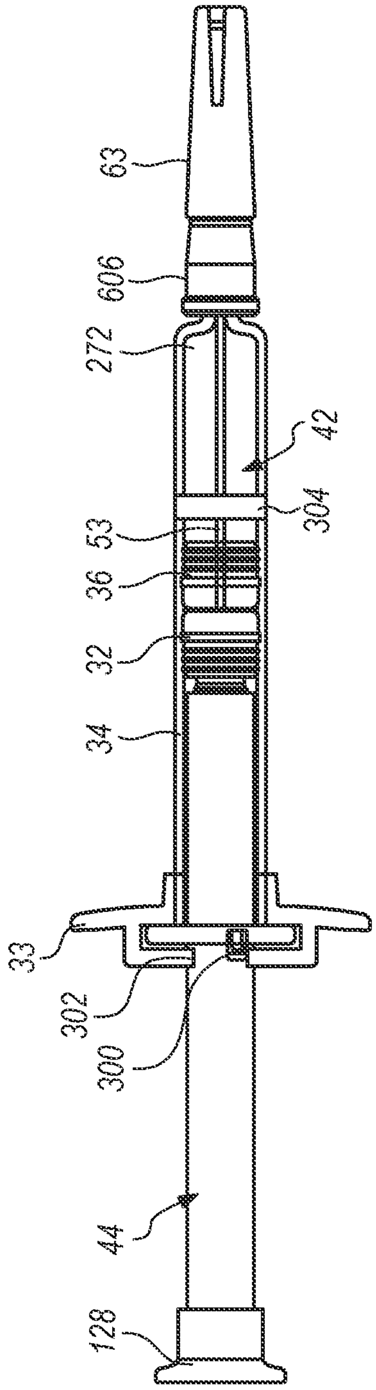
Figure 7L:
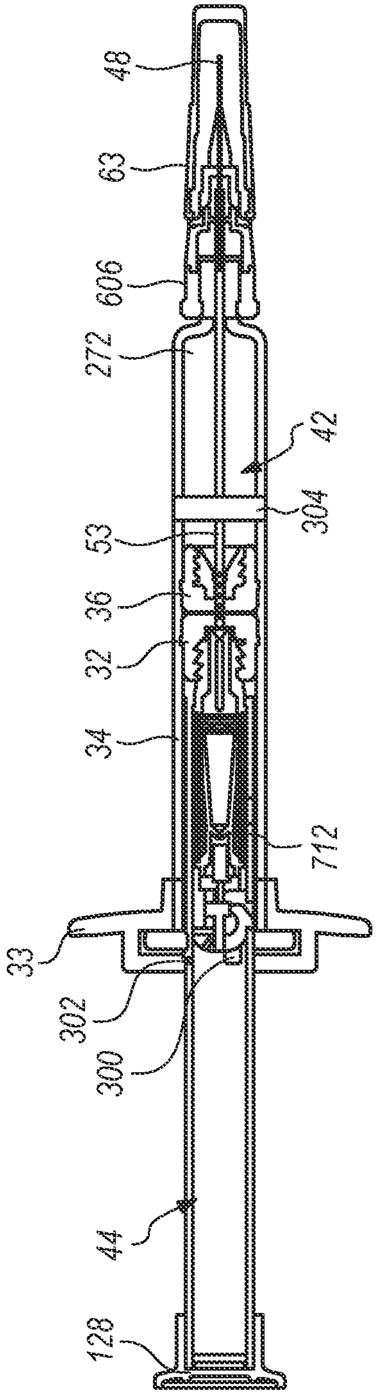
Figure 7M:
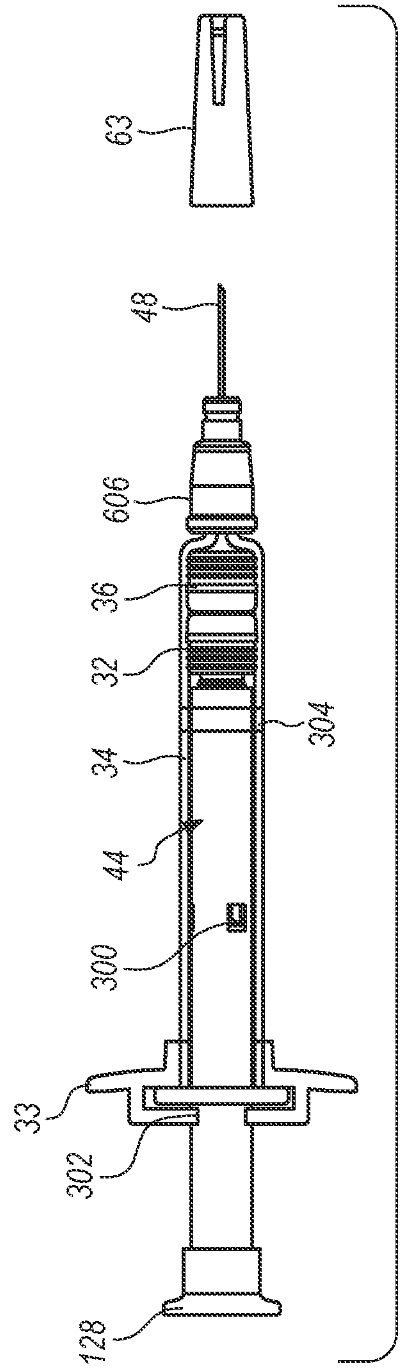
Figure 7N:
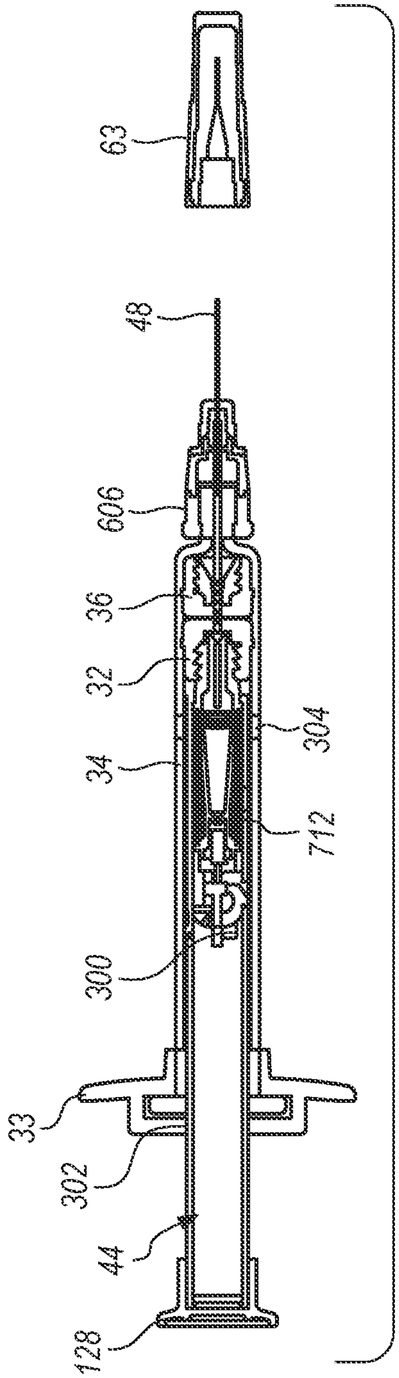
Figure 7O:
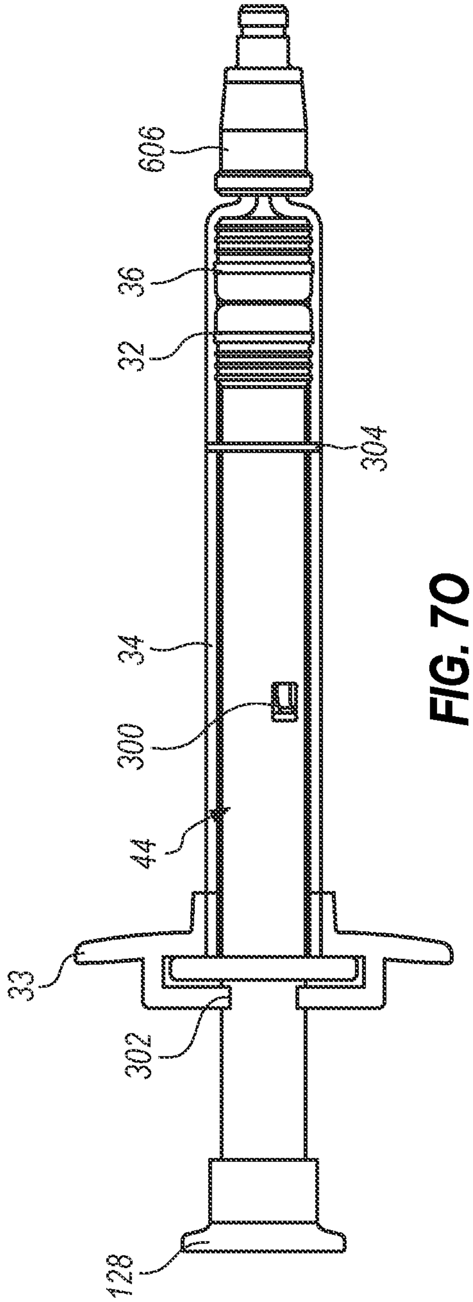
Figure 7P:
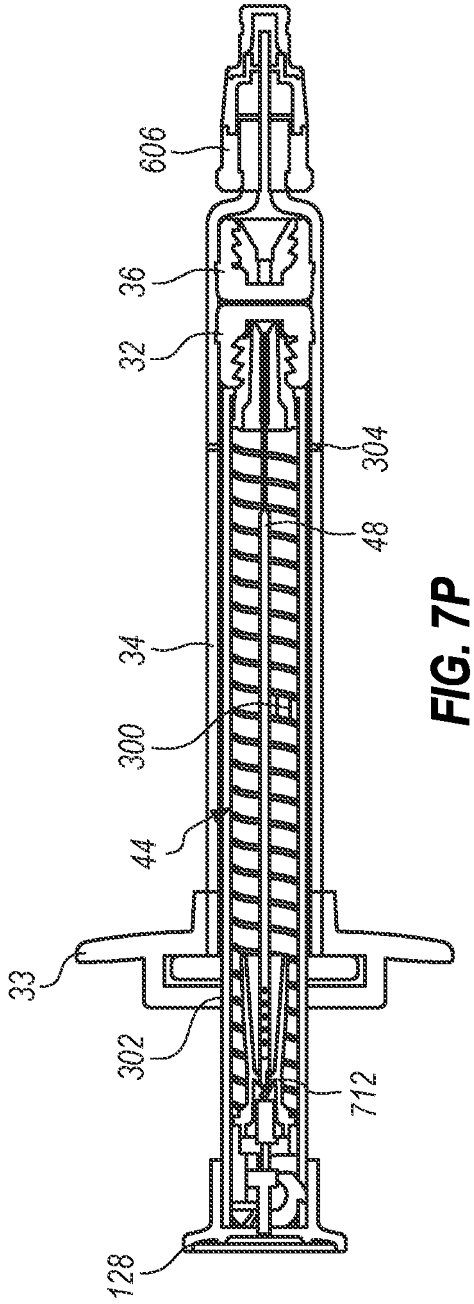

Referring to FIGS. 7A-7P, various aspects of configurations designed to facilitate injection of multi-part medications and retractions of a needle into a syringe body are illustrated, wherein two or more medication components are combined to form an injection combination or solution shortly before delivery into the patient. In one variation, a liquid first medicine component/diluent (252) may be combined with a substantially non-liquid second medicine component (254), such as a powdered form, of a drug agent, such as a freeze-dried or lyophilized drug component, shortly before injection. The configurations described herein in reference to FIGS. 7A-7P relate to dual-chamber configurations, wherein two or more chambers within the same syringe body (34) are utilized to carry, mix, and inject an injection solution.

Referring to FIGS. 7A and 7B, proximal and distal medicine chambers (40, 42) are formed by a distal stopper member (36) in between two portions of the interior of a syringe body (34), such that the distal medicine chamber (42) contains an air or gas gap, as well as a non-liquid medication (254); a proximal medicine chamber (40), on the opposite side of the distal stopper member (36) contains a liquid diluent (252), which is proximally contained by a proximal stopper member (32). The liquid diluent (252) is a first component of a medicine and the non-liquid medication (254) is a second component of the medicine. While the distal medicine chamber (42) is described as containing a non-liquid medicine (254) as a preferred embodiment, the distal medicine chamber (42) may contain a liquid, solid, or gel medicine intended to be mixed with the liquid diluent (252) in the proximal medicine chamber (40).

Referring to FIG. 7C, and the associated cross-sectional view in FIG. 7D, various components of a needle coupling assembly (here a so-called "staked" needle coupling assembly (606) is illustrated, but other needle assemblies as described below, including Luer-coupled as well as staked configurations, may be utilized). Lug features (258) are configured to assist with coupling the needle coupling assembly (606) to a needle cover member (63), as shown in FIG. 7A, for example. A small O-ring may be utilized as a sealing member (260) around the needle shaft, while a larger O-ring may be utilized as a sealing member (262) at the syringe body (34)/needle coupling assembly (606) interface. Alternatively, the small O-ring (260) and the large O-ring (262) may be combined into a single seal that performs both of the O-ring sealing functions. Also, the small O-ring (260) may be used to seal both around the needle shaft and to the syringe body (34).

The needle includes a plurality (e.g., four) of proximal openings/ports (270) configured to allow for entry of a liquid diluent, to be expelled out of a more distally-located middle opening/aperture (266); a lumen plug (268) occludes the needle lumen to create the flow path from the proximal openings (270) to the middle opening (266) under conditions such as those described above in reference to FIGS. 6N and 7H. The needle also includes a distal opening (264) on the opposite side of the lumen plug (268) from the middle opening (266). The distal opening (264) is fluidly coupled to the needle distal end (48) through the needle to inject liquid into a patient.

Referring to FIG. 7E, a proximal harpoon interface (84) is configured to serially penetrate proximal and distal stopper members (32, 36), and couple with a coupling feature (such as a needle retention feature are illustrated, for example, in FIGS. 7N and 7P, element (712)) in the plunger member (44). FIG. 7F illustrates a spike style harpoon coupling interface (85) that is configured to serially pierce both proximal and distal stopper members (32, 36) and couple with a coupling feature in the plunger member (44) to retract the needle member at least partially into the plunger member (44) after the injection has been given to the patient.

FIGS. 7A, 7B, and 7G-7P illustrate a sequence of actions for an injection procedure utilizing a dual chamber safe injection system such as that described above. Referring to FIGS. 7A and 7B, an injection assembly is in a stable configuration wherein it may be shipped or brought to an injection patient care scenario; a first drug component/liquid diluent (252) is isolated from a second non-liquid drug component (254), both within a syringe body on opposite sides of a distal stopper member (36).

FIGS. 7G and 7H illustrate initial insertion movement of the plunger member (44), advancing the distal (36) and proximal (32) stopper members together relative to the syringe body (34). Referring to FIG. 7H, with advancement sufficient to stab the needle proximal end (53) of the needle assembly across the distal stopper member (36), a fluid pathway is formed between the two previously isolated chambers (40, 42) of the syringe body (34), such that the liquid first drug component (252) in the proximal medicine chamber (40) may flow into at least one of the proximal openings (270), through the transfer pipe (46), and exit the more distal middle opening (266), to reach the non-liquid second drug component (254) in the distal medicine chamber (42).

FIGS. 7I and 7J illustrate that with further insertion until the stopper members (36, 32) are immediately adjacent each other, the liquid first drug component/diluent (252) has moved into the distal medicine chamber (42) to join the non-liquid second drug component (254). FIGS. 7K and 7L illustrate that with time and/or manual agitation, the liquid first drug component/diluent (252) and previously non-liquid second drug component (254) become mixed to form a mixed medication solution (272).

In some embodiment, especially with lyophilized non-liquid second drug components, the mixed medication solution (272) may be formed with minimal or no agitation or time passage. In another embodiment, especially with drugs which are held in suspension or emulsified drugs, vigorous shaking may be necessary to facilitate mixing. In the case of vigorous shaking it is useful to the user to be able to remove their thumb from the plunger manipulation interface (128). During transfer of liquid first medicine component (252) from the proximal to the distal medicine chambers (40, 42) pressure may build up in the distal medicine chamber (42). This pressure acts upon the proximal and distal stopper members (32, 36) to resist stopper motion. The pressure buildup may also move the stopper members (32, 36) and plunger manipulation interface (128) proximally if the user does not have their thumb restraining the plunger member (44). Mixed configuration latches or "mix clicks" in the plunger member (44) (described in U.S. Utility patent application Ser. No. 15/801,259, which was previously incorporated by reference herein) may be utilized to provide resistance to plunger manipulation interface (128) motion due to pressure buildup and allow the user to release their thumb from the plunger manipulation interface (128) for shaking or mixing of the drug. The mix clicks may also provide an audible and/or tactile indication that the transfer of liquid first medicine component (252) has been completed. The distal medicine chamber (42) may also include an agitation device, which assists in mixing of the medicine components.

With the assembly ready for injection of the mixed solution (272), the needle cover member (63) may be removed and the patient may be injected with the exposed needle distal end (48) with depression/insertion of the plunger member (44) and associated stopper members (36, 32) as shown in FIGS. 7M and 7N. Referring to FIGS. 7O and 7P, with full depression/insertion of the plunger member (44) and associated stopper members (32, 36), the sharp needle distal end/point (48) may automatically retract at least partially through the distal and proximal stopper members (36, 32) to a safe position within either the syringe body (34), the needle coupling assembly (606), or at least partially within the plunger member (44). Automatic retraction of the needle at least partially within the plunger is described in U.S. utility patent application Ser. No. 14/696,342, which was previously incorporated by reference herein.

Further details regarding multiple chamber injection systems (components, methods using same, etc.) are disclosed in U.S. Utility patent application Ser. No. 15/801,259, and U.S. Provisional Patent Application Ser. Nos. 62/682,381 and 62/729,880, which were all previously incorporated by reference herein.

Exemplary Dual Chamber Injection Systems with Distal Valves

Figure 8:
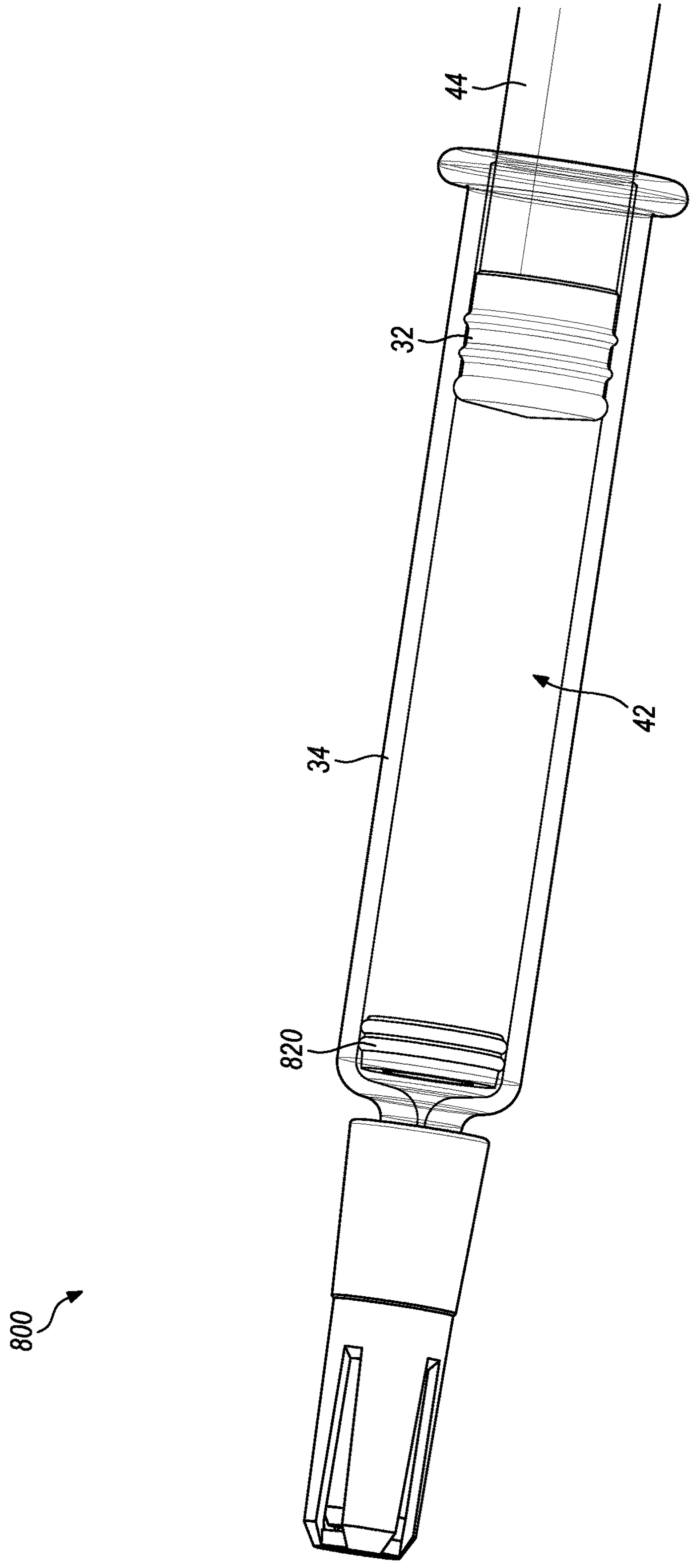
FIG. 8 is a perspective view illustrating various aspects of syringe based dual chamber injection systems with various components omitted for clarity according to some embodiments.

FIG. 8 depicts an injection system (800) having a valve (820) disposed therein according to some embodiments. While the injection system (800) is depicted without dual chamber components for clarity, the valve (820) is configured for use with either single chamber or dual chamber injection systems such as those described herein. In the case of a single chamber injection system, the medicine would be pre-mixed and ready for injection. The injection system (800) as shown includes an injection system body (34), a proximal stopper member (32), a plunger member (44), and an elongate fluid conveying member/needle member (50; see FIGS. 9 and 10). The elongate fluid conveying member/needle member (50) may be constructed of metal such as stainless steel. The proximal stopper member (32) together with the injection system body (34) forms a drug chamber (42). The injection system body (34) includes a distal needle interface (810) at a distal end thereof. In some embodiments, the distal needle interface (810) may include a pre-attached staked needle. In some embodiments, the distal needle interface (810) may be a Luer connector.

Figure 9:
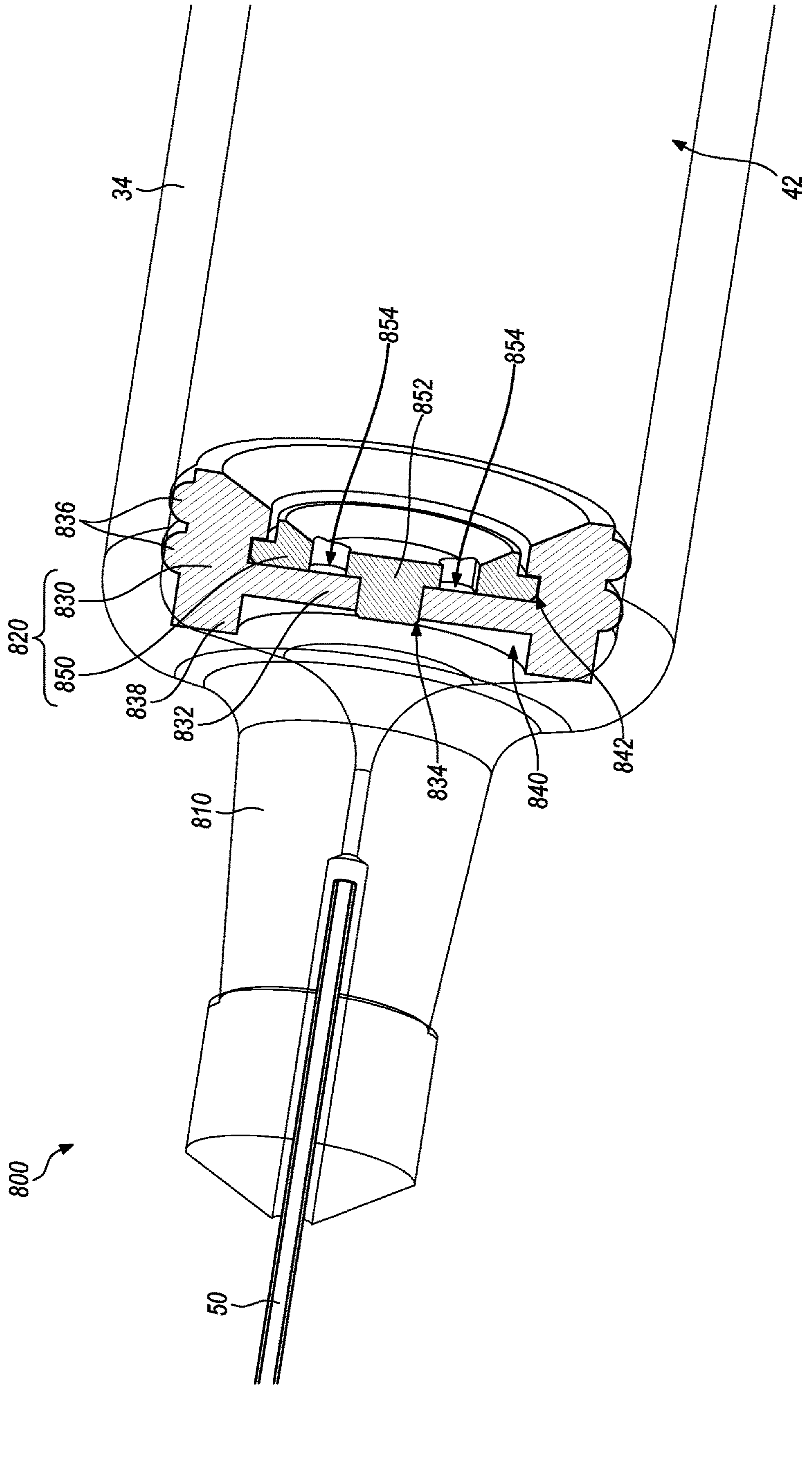
FIGS. 9 and 10 are detailed longitudinal cross-sectional illustrating various aspects of syringe based dual chamber injection systems with various components omitted for clarity according to some embodiments.

FIG. 9 depicts the injection system (800) and the valve (820) in greater detail in a closed configuration in which flow between the drug chamber (42) and the distal needle interface (810) is prevented. The valve (820) includes an outer member (830) and an inner member (850). The outer member (830) may be formed from an elastic material, and the inner member (850) may be formed from a rigid material. The elastic material forming the outer member (830) may be one or more of the following materials: rubber, butyl rubber, chlorobutyl rubber, bromobutyl rubber, thermoplastic elastomer, silicone rubber, thermoplastic, Polytetrafluoroethylene (PTFE), thermoset plastic. The outer member (830) may be coated with a lubricious polymer such as PTFE, silicone oil, and/or other lubricious coatings. The rigid material forming the inner member (850) may be one or more of the following materials: polymer, metal, glass, ceramic, hard durometer rubber, stainless steel, titanium, glass coated polymer, ceramic coated polymer, cyclic olefin copolymer (COC), cyclic olefin polymer (COP). The inner member (850) may be coated with a lubricious polymer such as PTFE film, silicone oil, and/or other lubricious coatings.

The outer member (830) includes a distal diaphragm (832) that defines a distal opening (834) therein. In the embodiment depicted in FIG. 9, the distal opening (834) is in an approximate center of the distal diaphragm (832). The outer member (830) also includes a pair of outward annular members (836) configured to form a fluid-tight seal between the outer member (830) and an inner surface of the injection system body (34). While a pair of outward annular members (836) are shown in FIG. 9, there may be one annular member or more than two annular members configured to form a fluid tight seal between the outer member (830) and the inner surface of the injection system body (34). The outer member (830) further includes a distally extending ring (838) to position the distal diaphragm (832) proximally away from a distal end of the injection system body (34) to provide a space (840) into which the distal diaphragm (832) may deflect. The outer member (830) also defines an annular groove (842) configured to secure the inner member (850) in the outer member (830). In the closed configuration depicted in FIG. 9, the distal diaphragm (832) is disposed against the inner member (850). The distal diaphragm (832) is configured/biased to be in the closed configuration depicted in FIG. 9 when no external forces are acting thereon.

The inner member (850) includes a distally extending member (852) configured to fit in and interfere with the distal opening (834) in the distal diaphragm (832) when the distal diaphragm (832) is in the closed configuration. In various embodiments, the distally extending member (852) may be made from polymer, plastic, metal, glass, or other materials. The inner member (850) defines a pair of proximal openings (854), which are closed/interfered with by the distal diaphragm (832) when the distal diaphragm (832) is in the closed configuration.

With the distal diaphragm (832) in the closed configuration against the inner member (850) as depicted in FIG. 9, the distal diaphragm (832) closes the proximal openings (854) interfering with flow therethrough. Further, with the distal diaphragm (832) in the closed configuration, the distally extending member (852) closes the distal opening (834) in the distal diaphragm (832) interfering with flow therethrough.

Figure 10:
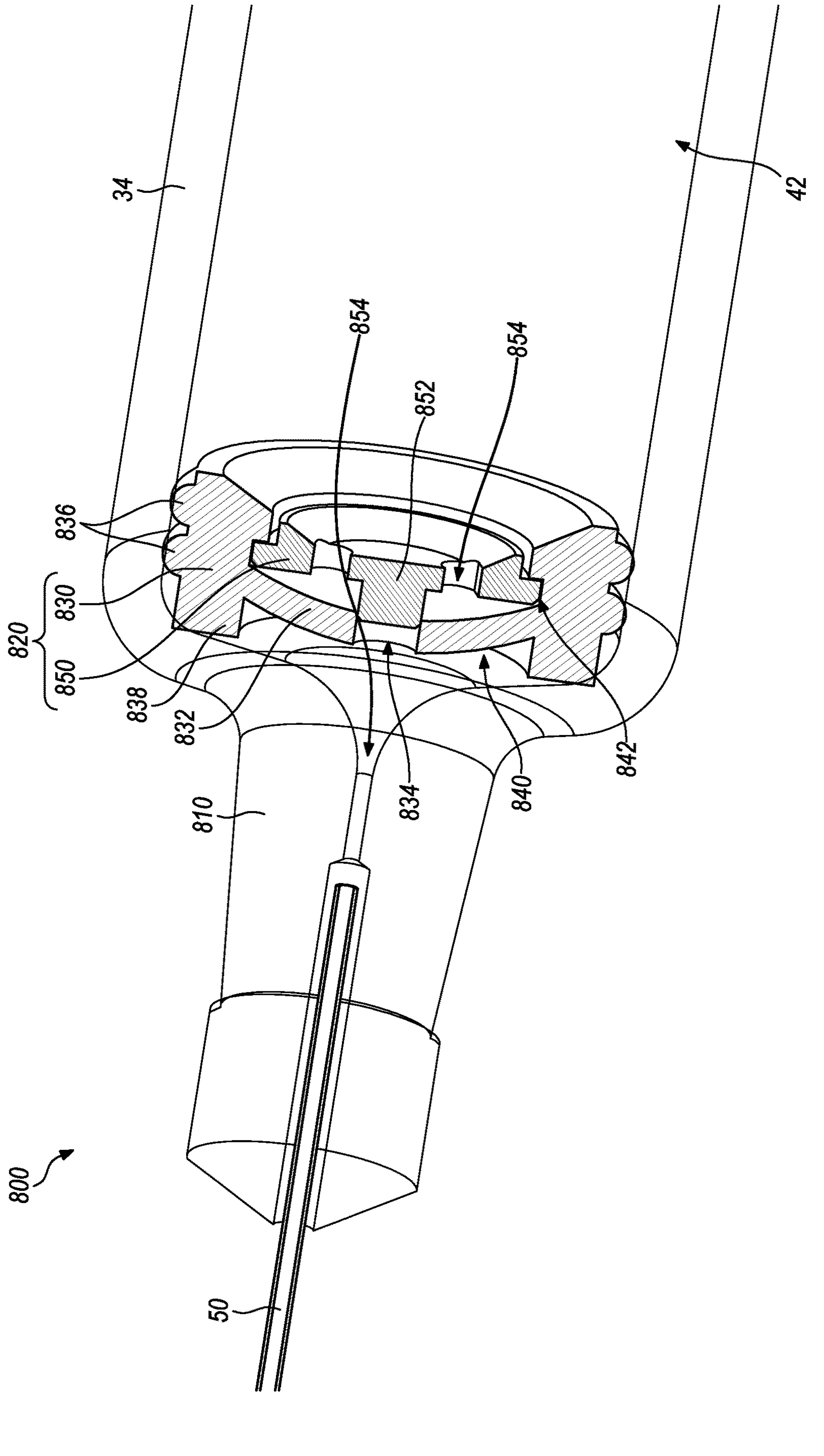

FIG. 10 depicts the injection system (800) and the valve (820) in an open configuration in which flow between the drug chamber (42) and the distal needle interface (810) is enabled. In the open configuration, the distal diaphragm (832) deforms/deflects distally away from the inner member (850) thereby unblocking the proximal openings (854) in the inner member (850) and the distal opening (834) in the distal diaphragm (832). The distal diaphragm (832) converts from the closed configuration depicted in FIG. 9 to the open configuration depicted in FIG. 10 with increased pressure in the drug chamber (42). In some embodiments, the distal diaphragm (832) is configured to convert from the closed configuration to the open configuration when a pressure in the drug chamber (42) is equal to or greater than approximately 10 psi. The distal diaphragm (832) is configured such that the distal diaphragm (832) exerts minimal resistance on fluid flow from the drug chamber (42) through the proximal and distal openings (854, 834) when the distal diaphragm (832) is in the open configuration.

Figure 11:
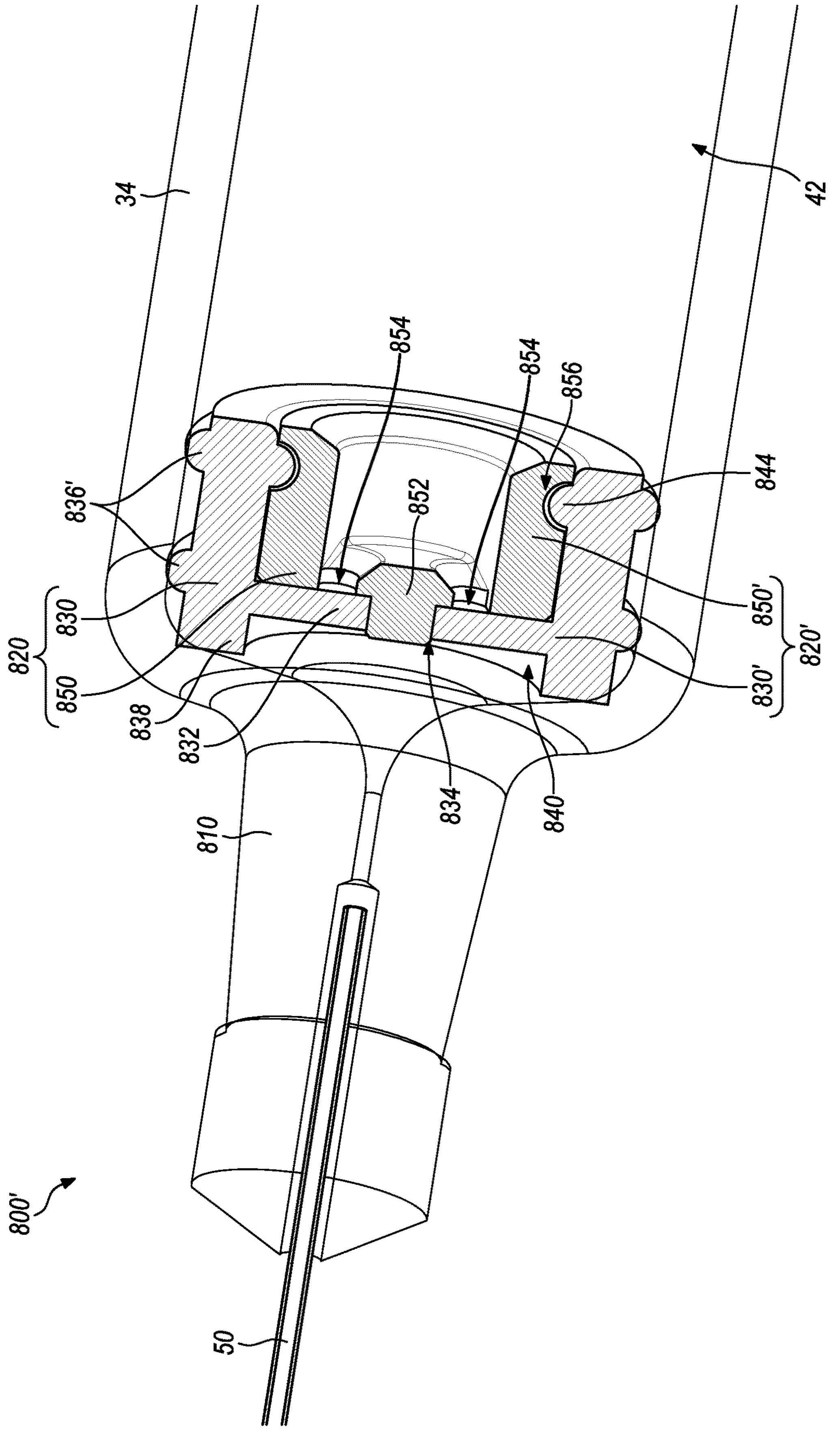
FIGS. 11 and 12 are detailed longitudinal cross-sectional illustrating various aspects of syringe based dual chamber injection systems with various components omitted for clarity according to some embodiments.
Figure 12:
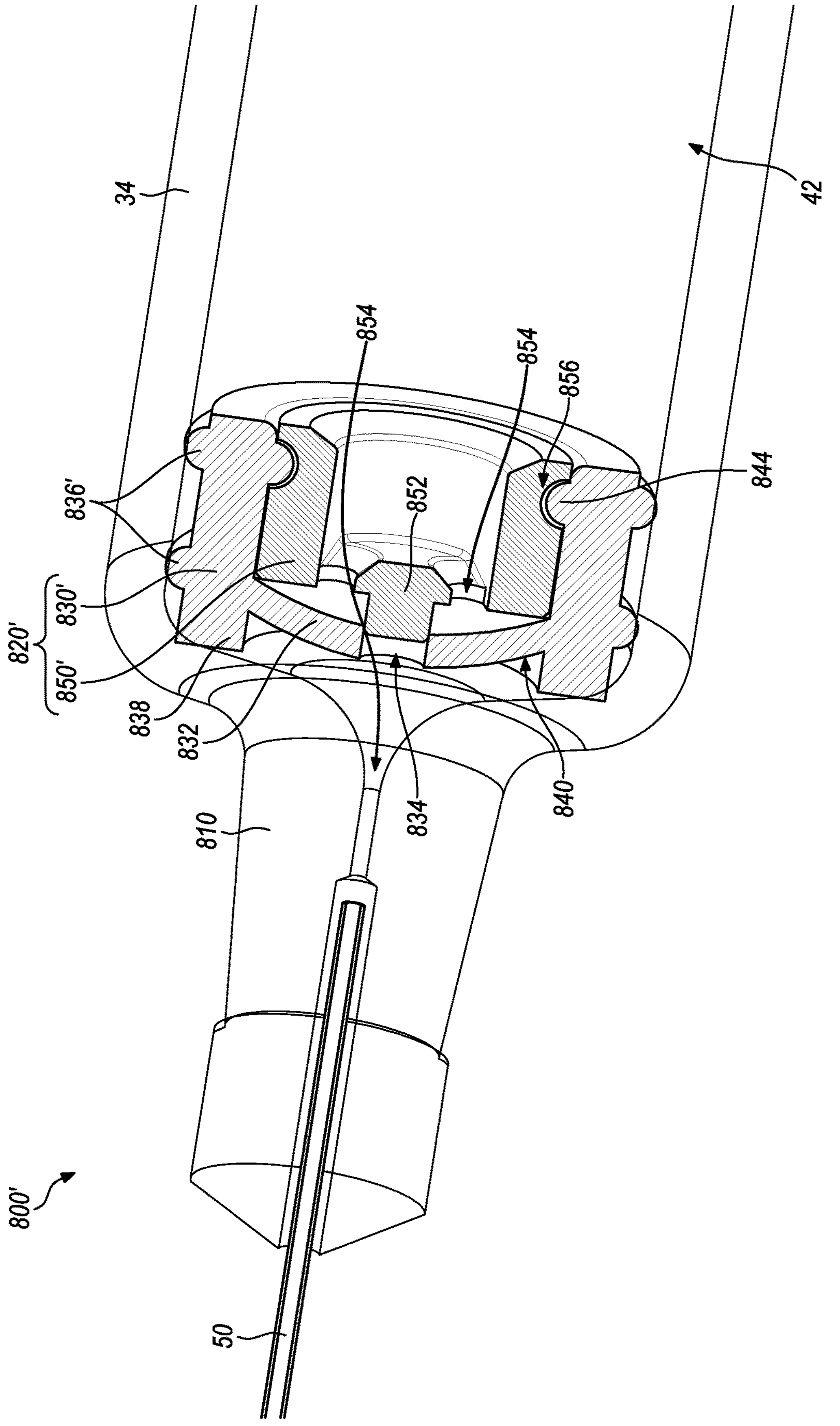

FIGS. 11 and 12 depict an injection system (800') and the valve (820') according to some embodiments in respective closed and open configurations. The injection system (800') and the valve (820') depicted in FIGS. 11 and 12 are similar to the injection system (800) and the valve (820) depicted in FIGS. 9 and 10. The difference between the injection systems (800, 800') and the valves (820, 820') is that the outer and inner members (830', 850') of the valve (820') are elongated to provide a space between the radially outward annular members (836') of the outer member (830'). Spacing apart the radially outward annular members (836') facilitates vacuum-assisted assembly to move the valve (820') axially along the injection system body (34) while maintaining stability to prevent tipping of the valve (820'). The valve (820) depicted in FIGS. 9 and 10 is more suitable to mechanically-assisted assembly (e.g., with a vent tube), which minimizes tipping of the valve (820).

Another difference between the valves (820, 820') is the securing mechanism between the outer and inner members (830', 850'). The inner member (850') defines an annular groove (856) and the outer member (830') includes a radially inward annular member (844) configured to interfere with the annular groove (856) to secure the inner member (850') in the outer member (830').

In the closed configuration depicted in FIG. 11, the distal diaphragm (832) closes the proximal openings (854) interfering with flow therethrough. Further, with the distal diaphragm (832) in the closed configuration, the distally extending member (852) closes the distal opening (834) in the distal diaphragm (832) interfering with flow therethrough. As such, flow from the drug chamber (42) through the valve (820') to the needle interface member (810) is prevented when the distal diaphragm (832) is in the closed configuration depicted in FIG. 11.

With increased pressure (e.g., 10 psi) in the drug chamber (42), the distal diaphragm (832) converts to the open configuration shown in FIG. 12 in which flow between the drug chamber (42) and the distal needle interface (810) is enabled. In the open configuration, the distal diaphragm (832) deforms/deflects distally away from the inner member (850) thereby unblocking the proximal openings (854) in the inner member (850) and the distal opening (834) in the distal diaphragm (832). The distal diaphragm (832) is configured such that the distal diaphragm (832) exerts minimal resistance on fluid flow from the drug chamber (42) through the proximal and distal openings (854, 834) when the distal diaphragm (832) is in the open configuration.

The valve (820) may be configured to perform one, two, three, or all of four functions described below. First, the valve (820) may minimize and/or eliminate movement of the non-liquid second medicine component into the distal needle interface (810) during assembly and storage of the injection system (800). Second, the valve (820) may prevent contact between stainless steel sensitive medications and the elongate fluid conveying member/needle member (50), which may be constructed of stainless steel. As such, the valve (820) may allow medication which may be corrosive or degraded by contact with stainless steel to be stored in the distal medicine chamber. This is useful in dual chamber configurations and in single chamber configurations where the medicine is pre-mixed and pre-filled in the medicine chamber. Third, the valve (820) may minimize and/or eliminate drug loss during shaking mixing from a vented injection system (800). Fourth, in vented injection systems (800) where the distal needle interface (810) is open to the atmosphere to allow air to escape during liquid transfer from the proximal chamber (40) to the distal chamber (42), the valve (820) may prevent loss of the mixed medicine from the opening in the distal needle interface (810) during shaking and mixing of the medicine components. This fourth function prevents drug loss and protects the environment from toxic drugs. These valve functions, especially the third and fourth functions, facilitate the drug components in the proximal and distal chambers (40, 42) to be fully mixed before the mixed medicine is ejected distally out of the injection system body (34) through the distal needle interface (810) (e.g., into either a medication bag or a needle).

Figure 13:
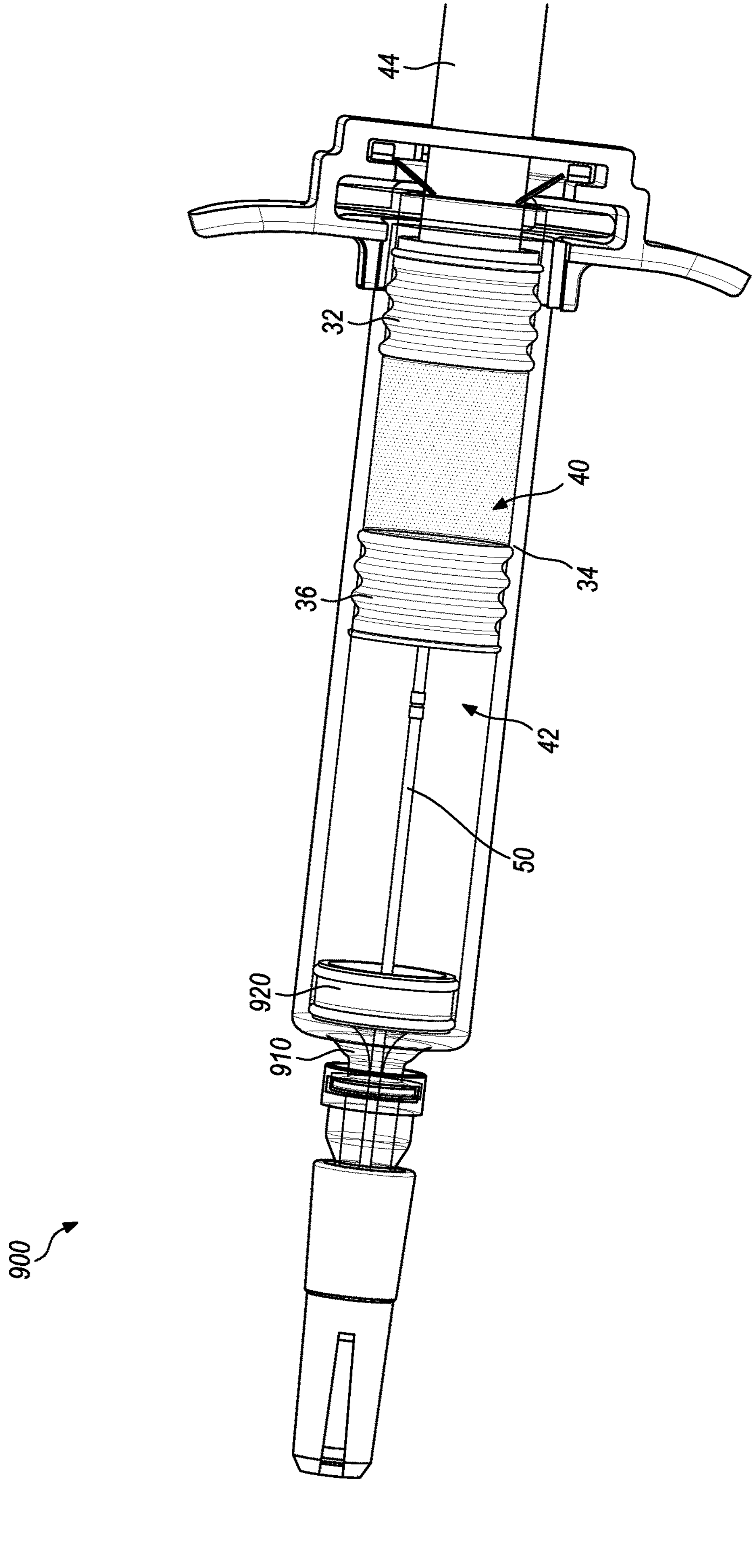
FIG. 13 is a perspective view illustrating various aspects of syringe based dual chamber injection systems according to some embodiments.

FIG. 13 depicts a dual chamber injection system (900) having a valve (920) disposed therein according to some embodiments. Similar to the dual chamber injection systems depicted in FIGS. 6A to 7P, the dual chamber injection system (900) includes an injection system body (34), proximal and distal stopper members (32, 36), a plunger member (44), and an elongate fluid conveying member/needle member (50). The proximal and distal stopper members (32, 36) together with the injection system body (34) form proximal and distal drug chambers (40, 42) as described herein. The proximal and distal drug chambers (40, 42) are prefilled with a liquid first medicine component and a non-liquid second medicine component (not shown for clarity; see 252, 254 in FIGS. 6A and 6B). The elongate fluid conveying member/needle member (50) defines a middle opening (52) fluidly coupled through a needle interior to an open distal end of the elongate fluid conveying member/needle member (50) thereby forming a flow path through the elongate fluid conveying member/needle member (50).

The injection system body (34) includes a distal needle interface (910) at a distal end thereof. In some embodiments, the distal needle interface (910) may be a Luer connector. The distal needle interface (910) may have many small spaces formed therein. If non-liquid second medicine component moves into some of the small spaces in the distal needle interface (910), the non-liquid second medicine component may clog these small spaces and prevent any liquid from exiting the injection system body (34). The non-liquid second medicine component in these small spaces may not dissolve, thereby changing the final concentration of medicines in the mixed medicine.

The valve (920) may perform one, two, three, or all of four functions described below. First, the valve (920) may minimize and/or eliminate movement of the non-liquid second medicine component into the distal needle interface (910) during assembly and storage of the injection system (900). Second, the valve (920) may center and stabilize the elongate fluid conveying member/needle member (50), thereby facilitating piercing of the distal stopper member (36) by the elongate fluid conveying member/needle member (50). Third, the valve (920) may minimize and/or eliminate drug loss during shaking mixing from a vented injection. Fourth, in vented injection systems (900) where the distal needle interface (910) is open to the atmosphere to allow the escape of air during liquid transfer from the proximal chamber (40) to the distal chamber (42), the valve (920) may prevent loss of the mixed medicine from the opening in the distal needle interface (910) during shaking and mixing of the medicine components. This fourth function prevents drug loss and protects the environment from toxic drugs. These valve functions, especially the third and fourth functions, facilitate the drug components in the proximal and distal chambers (40, 42) to be fully mixed before the mixed medicine is ejected distally out of the injection system body (34) through the distal needle interface (910) (e.g., into either a medication bag or a needle).

Figure 14:
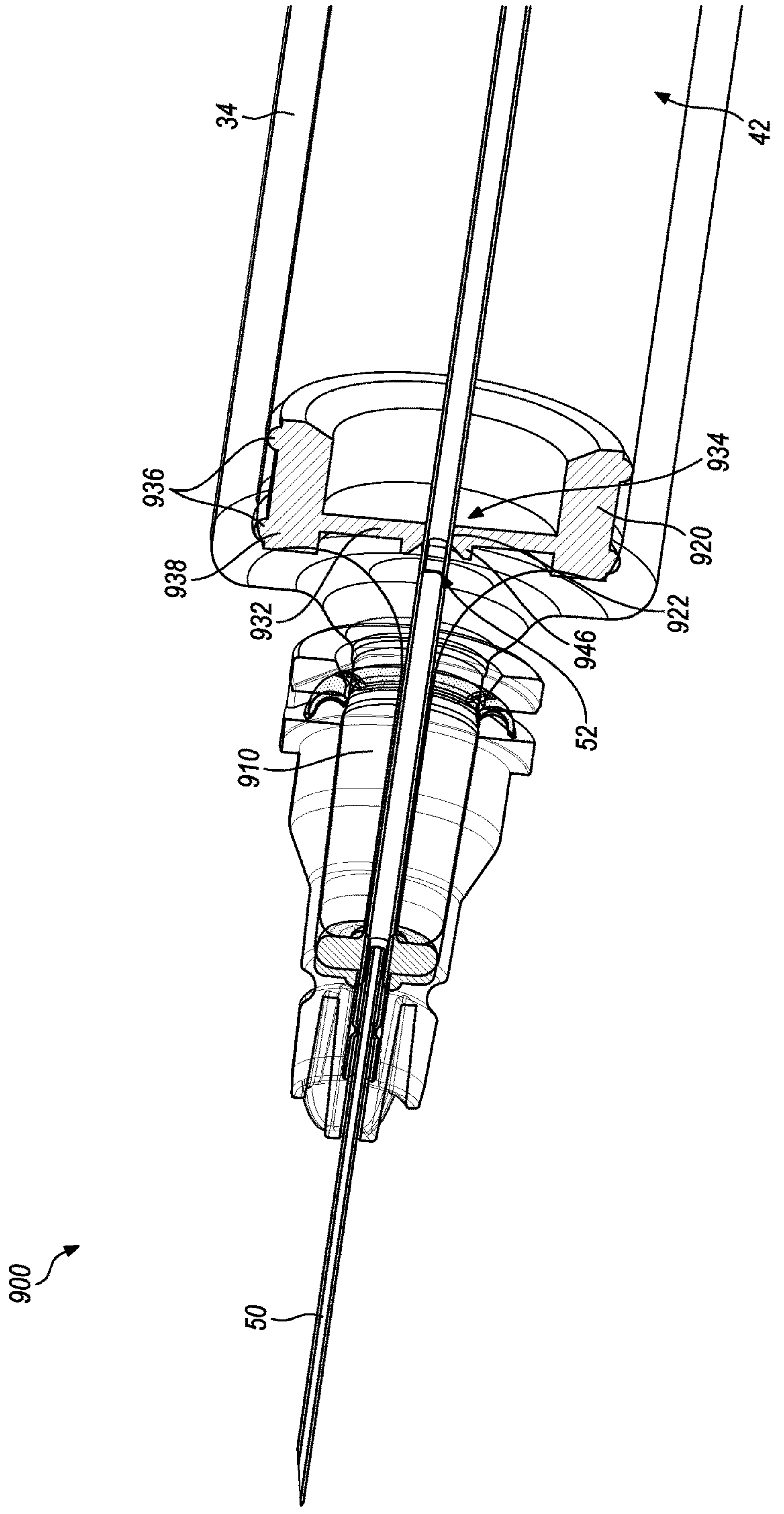
FIGS. 14 to 16 are detailed longitudinal cross-sectional illustrating various aspects of syringe based dual chamber injection systems according to some embodiments.

FIG. 14 depicts the injection system (900) and the valve (920) in greater detail in a closed configuration in which flow between the distal drug chamber (42) and the middle opening (52) of the elongate fluid conveying member/needle member (50) is prevented. The valve (920) may be formed from an elastic material. The elastic material may be one or more of the following materials: rubber, butyl rubber, chlorobutyl rubber, bromobutyl rubber, thermoplastic elastomer, silicone rubber, thermoplastic, Polytetrafluoroethylene (PTFE), thermoset plastic. The valve (920) may be coated with a lubricious polymer such as PTFE film, silicone oil, and/or other lubricious coatings.

The valve (920) includes an elastic diaphragm (932) that defines a diaphragm opening (934) therein and configured to receive at least a portion of the elongate fluid conveying member/needle member (50) therethrough. In the embodiment depicted in FIG. 14, the diaphragm opening (934) is in an approximate center of the elastic diaphragm (932). The valve (920) also includes a seal (922) around the diaphragm opening (934) and configured to prevent fluid flow from the distal drug chamber (42) through the middle opening (52) of the elongate fluid conveying member/needle member (50) when the elastic diaphragm (932) is in the closed configuration depicted in FIG. 14. The valve (920) further includes a pair of outward annular members (936) configured to form a fluid-tight seal between the valve (920) and an inner surface of the injection system body (34). In some embodiments, there may be a singular annular member or more than two annular members. Moreover, the valve (920) includes a distally extending ring (938) to position the elastic diaphragm (932) proximally away from a distal end of the injection system body (34) to provide a space (940) into which the elastic diaphragm (932) may deflect. In addition, the valve (920) includes a distally facing funnel (944) to facilitate assembly and center the elongate fluid conveying member/needle member (50).

In the closed configuration depicted in FIG. 14, the elastic diaphragm (932) is disposed proximal of the middle opening (52) in the elongate fluid conveying member/needle member (50), thereby providing a fluid tight seal separating the middle opening (52) from the distal drug chamber (42). The elastic diaphragm (932) is configured/biased to be in the closed configuration depicted in FIG. 14 when no external forces are acting thereon.

Figure 15:
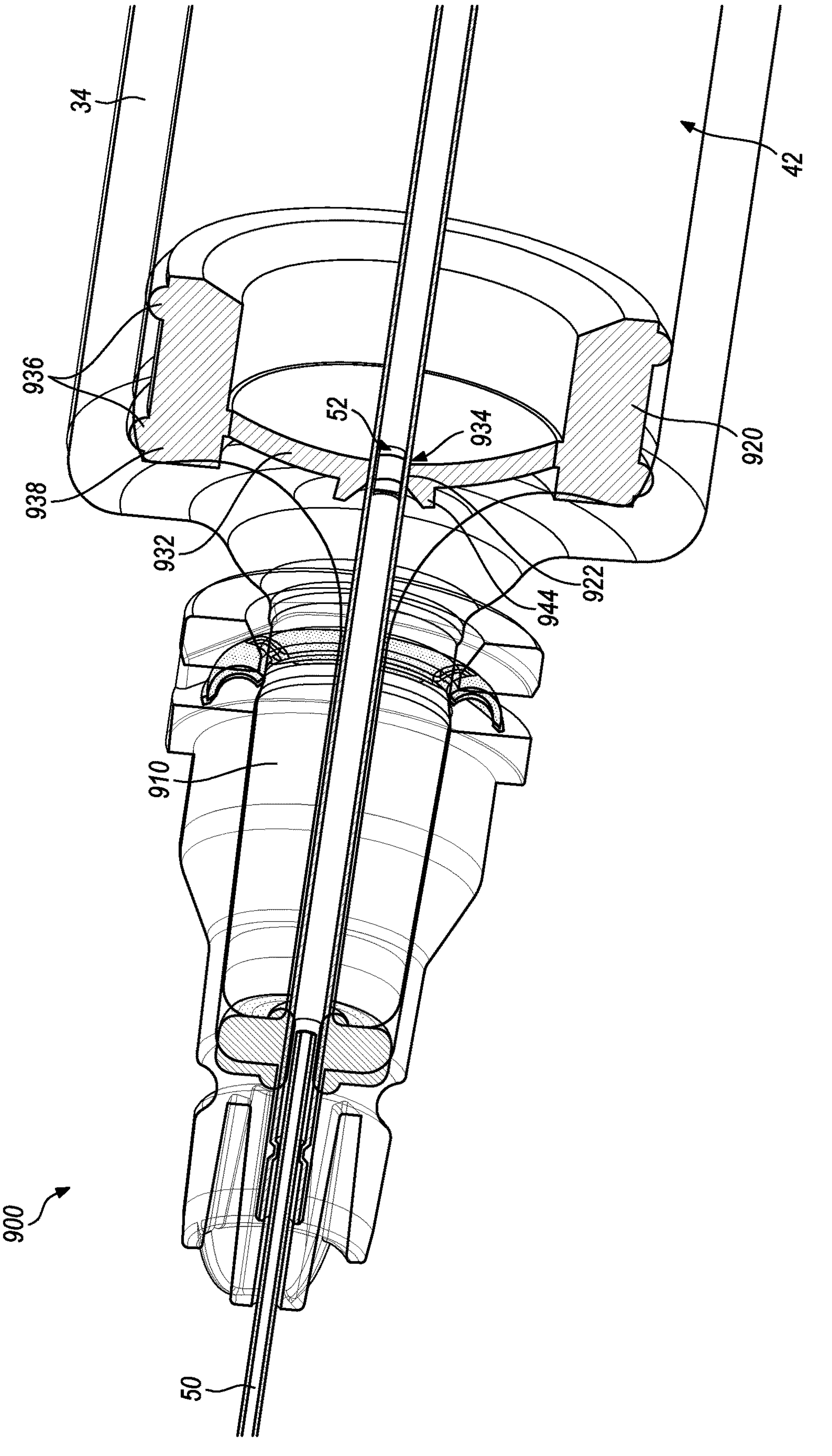

FIG. 15 depicts the injection system (900) and the valve (920) in an open configuration in which flow between the distal drug chamber (42) and the middle opening (52) of the elongate fluid conveying member/needle member (50) is enabled. In the open configuration, the elastic diaphragm (932) deforms/deflects distally over the middle opening (52) thereby opening a flow path between the distal drug chamber (42 and the middle opening (52 of the elongate fluid conveying member/needle member (50). The elastic diaphragm (932) converts from the closed configuration depicted in FIG. 14 to the open configuration depicted in FIG. 15 with increased pressure in the distal drug chamber (42). In some embodiments, the elastic diaphragm (932) is configured to convert from the closed configuration to the open configuration when a pressure in the distal drug chamber (42) is equal to or greater than approximately 10 psi. The elastic diaphragm (932) is configured such that the elastic diaphragm (932) exerts minimal resistance on fluid flow from the distal drug chamber (42) through the middle opening (952) when the elastic diaphragm (932) is in the open configuration.

Figure 16:
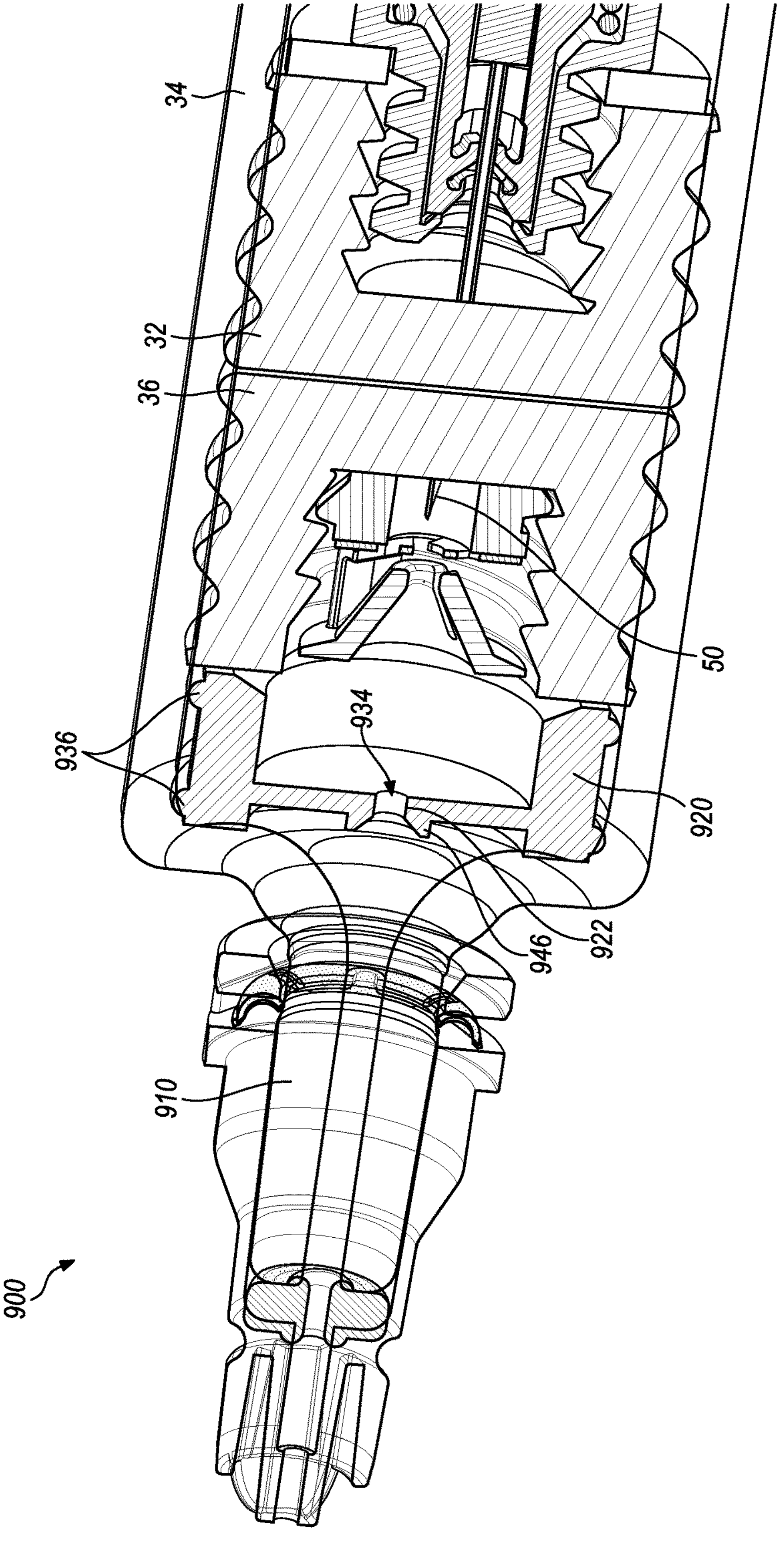

FIG. 16 depicts the injection system (900) after injection is completed and the elongate fluid conveying member/needle member (50) is retracted into the injection system body (34) for safety. Automatic retraction of the needle at least partially within the plunger is described in U.S. utility patent application Ser. No. 14/696,342, which was previously incorporated by reference herein.

Figure 17:
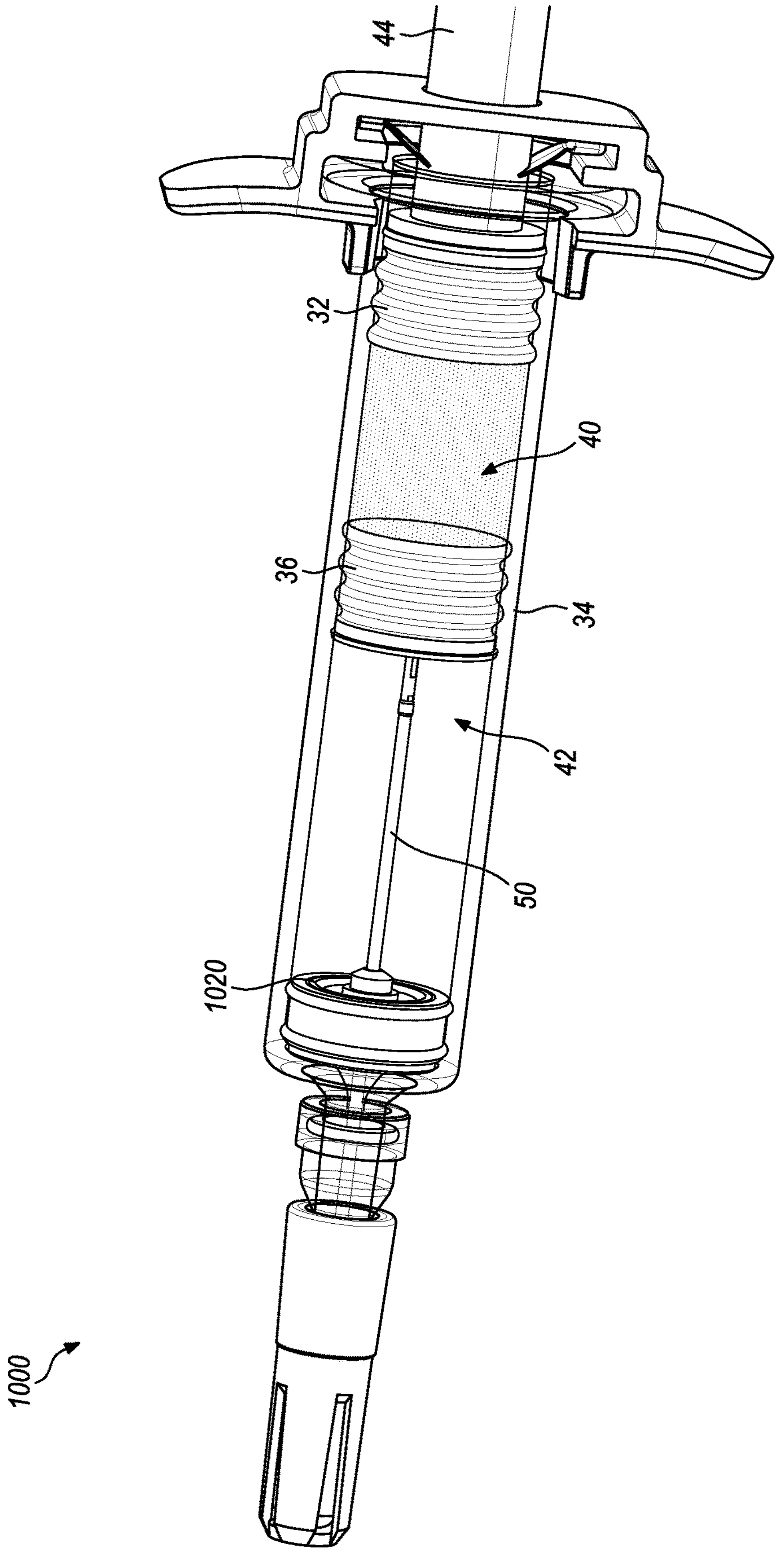
FIG. 17 is a perspective view illustrating various aspects of syringe based dual chamber injection systems according to some embodiments.

FIG. 17 depicts a dual chamber injection system (1000) having a valve (1020) disposed therein according to some embodiments. Similar to the dual chamber injection systems depicted in FIGS. 6A to 7P and 13 to 16, the dual chamber injection system (1000) includes an injection system body (34), proximal and distal stopper members (32, 36), a plunger member (44), and an elongate fluid conveying member/needle member (50). The proximal and distal stopper members (32, 36) together with the injection system body (34) form proximal and distal drug chambers (40, 42) as described herein. The proximal and distal drug chambers (40, 42) are prefilled with a liquid first medicine component and a non-liquid second medicine component (not shown for clarity; see 252, 254 in FIGS. 6A and 6B). The elongate fluid conveying member/needle member (50) defines a middle opening (52) fluidly coupled through a needle interior to an open distal end of the elongate fluid conveying member/needle member (50) thereby forming a flow path through the elongate fluid conveying member/needle member (50).

The injection system body (34) includes a distal needle interface (1010) at a distal end thereof. In some embodiments, the distal needle interface (1010) may be a Luer connector. The distal needle interface (1010) may have many small spaces formed therein. The valve (1020) depicted in FIG. 17 has the same functions as the valve (920) depicted in FIG. 13.

Figure 18:
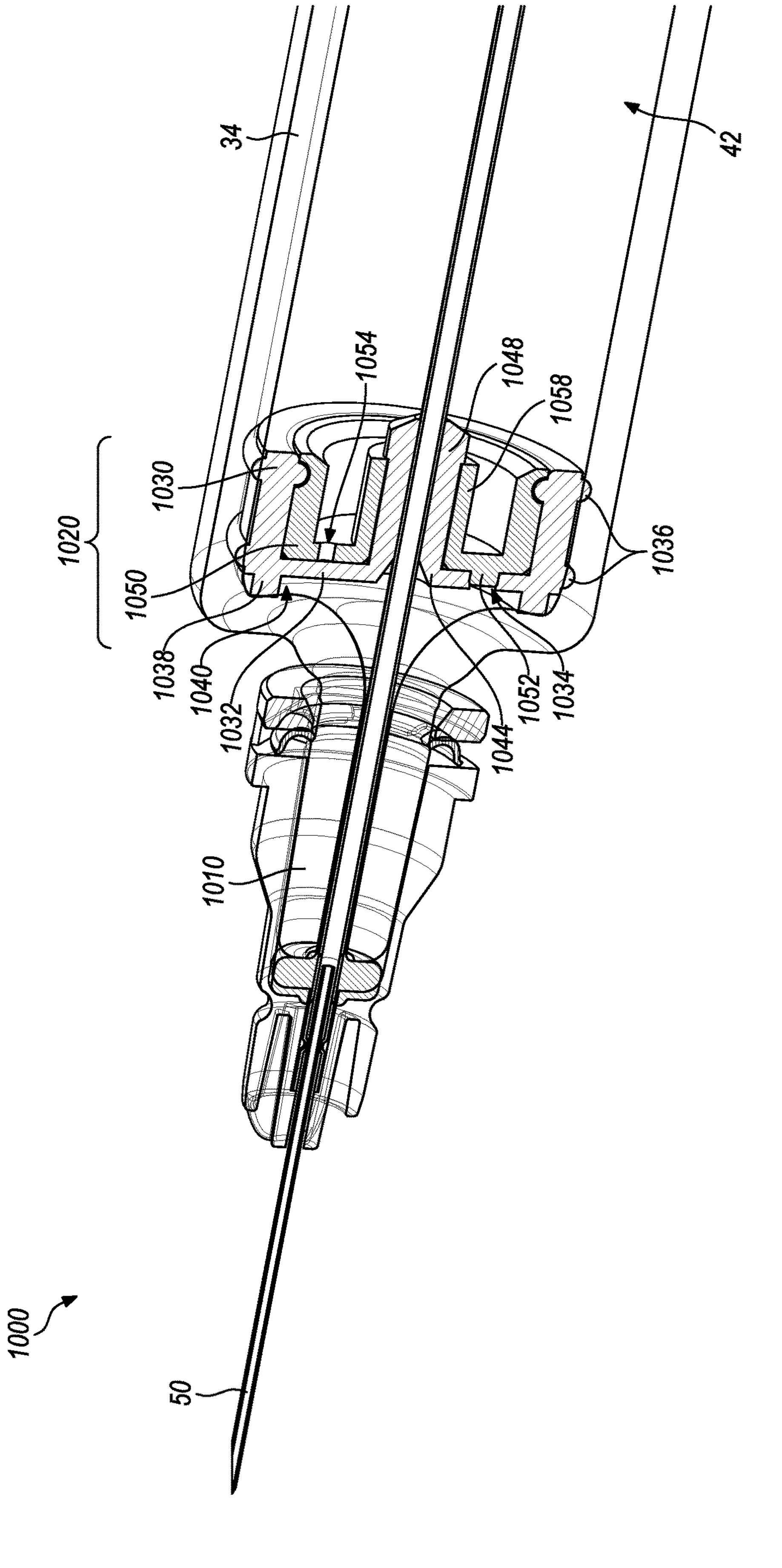
FIGS. 18 and 19 are detailed longitudinal cross-sectional illustrating various aspects of syringe based dual chamber injection systems according to some embodiments.

FIG. 18 depicts the injection system (1000) and the valve (1020) in greater detail in a closed configuration in which flow between the distal drug chamber (42) and the distal needle interface (1010) is prevented. The valve (1020) includes an outer member (1030) and an inner member (1050). The outer member (1030) may be formed from an elastic material, and the inner member (1050) may be formed from a rigid material. The elastic material forming the outer member (1030) may be one or more of the following materials: rubber, butyl rubber, chlorobutyl rubber, bromobutyl rubber, thermoplastic elastomer, silicone rubber, thermoplastic, Polytetrafluoroethylene (PTFE), thermoset plastic. The outer member (1030) may be coated with a lubricious polymer such as PTFE film, silicone oil, and/or other lubricious coatings. The rigid material forming the inner member (1050) may be one or more of the following materials: polymer, metal, glass, ceramic, hard durometer rubber, stainless steel, titanium, glass coated polymer, ceramic coated polymer, cyclic olefin copolymer (COC), cyclic olefin polymer (COP). The inner member (1050) may be coated with a lubricious polymer such as PTFE film, silicone oil, and/or other lubricious coatings.

The outer member (1030) includes a distal diaphragm (1032) that defines a distal opening (1034) therein. In the embodiment depicted in FIG. 18, the distal opening (1034) is in an approximate center of the distal diaphragm (1032). The outer member (1030) also includes a pair of outward annular members (1036) configured to form a fluid-tight seal between the outer member (1030) and an inner surface of the injection system body (34). While two outward annular members (1036) are shown in FIG. 18, other embodiments may include a single annular member or more than two annular members. The outer member (1030) further includes a distally extending ring (1038) to position the distal diaphragm (1032) proximally away from a distal end of the injection system body (34) to provide a space (1040) into which the distal diaphragm (1032) may deflect. The outer member (1030) also defines a radially inward annular member (1048) configured to secure the inner member (1050) in the outer member (1030). In the closed configuration depicted in FIG. 18, the distal diaphragm (1032) is disposed against the inner member (1050). The distal diaphragm (1032) is configured/biased to be in the closed configuration depicted in FIG. 18 when no external forces are acting thereon. In addition, the valve (1020) includes a distally facing funnel (1044) to facilitate assembly and center the elongate fluid conveying member/needle member (50).

The inner member (1050) includes a distally extending member (1052) configured to fit in and interfere with the distal opening (1034) in the distal diaphragm (1032) when the distal diaphragm (1032) is in the closed configuration. The inner member (1050) defines a proximal opening (1054), which is closed/interfered with by the distal diaphragm (1032) when the distal diaphragm (1032) is in the closed configuration. The inner member (1050) also defines an annular groove (1056) configured to interfere with the radially inward annular member (1048) of the outer member (1030) to secure the inner member (1050) in the outer member (1030).

With the distal diaphragm (1032) in the closed configuration against the inner member (1050) as depicted in FIG. 18, the distal diaphragm (1032) closes the proximal opening (1054) interfering with flow therethrough. Further, with the distal diaphragm (1032) in the closed configuration, the distally extending member (1052) closes the distal opening (1034) in the distal diaphragm (1032) interfering with flow therethrough.

Figure 19:
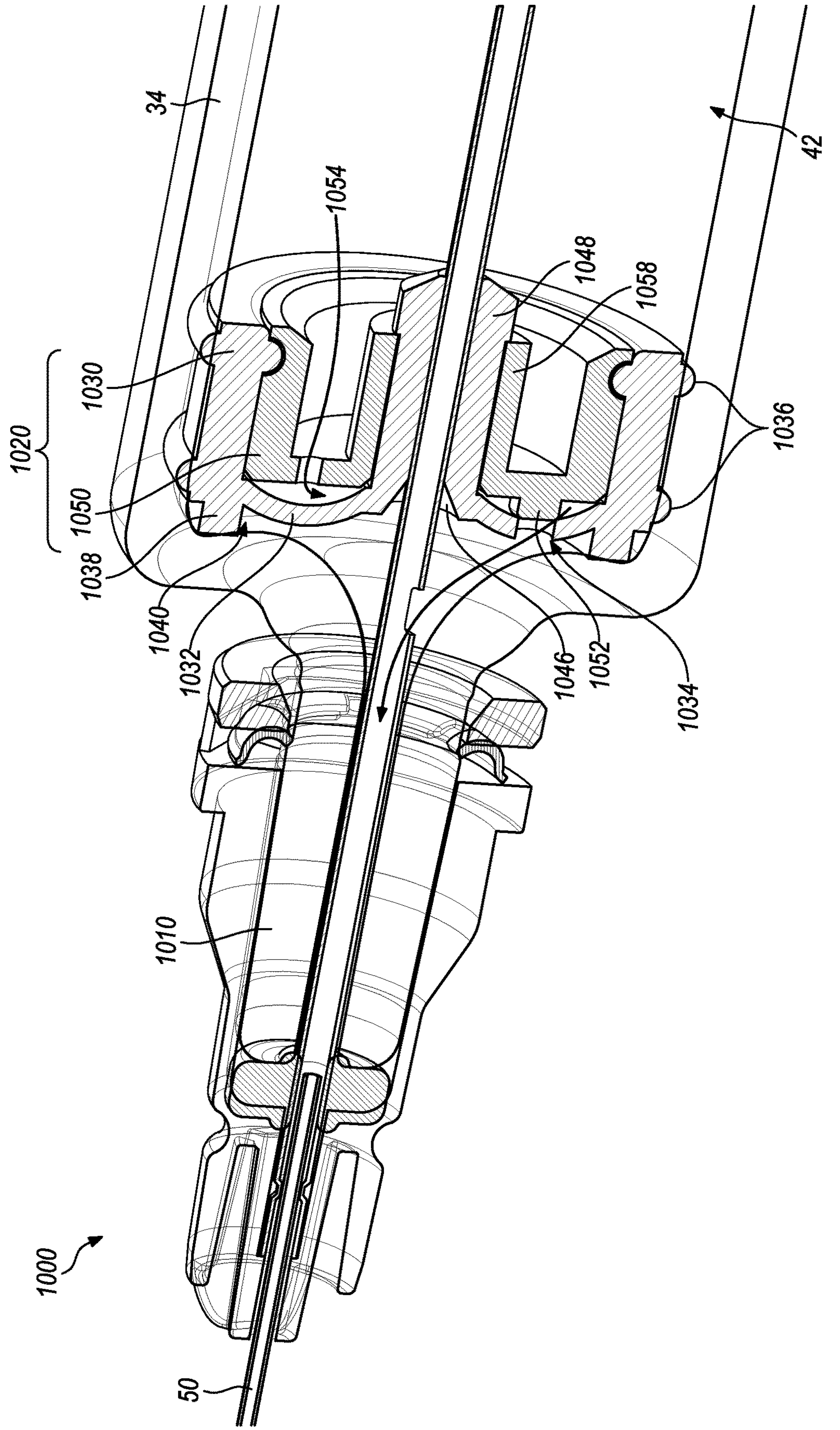

FIG. 19 depicts the injection system (1000) and the valve (1020) in an open configuration in which flow between the distal drug chamber (42) and the distal needle interface (1010) is enabled. In the open configuration, the distal diaphragm (1032) deforms/deflects distally away from the inner member (1050) thereby unblocking the proximal openings (1054) in the inner member (1050) and the distal opening (1034) in the distal diaphragm (1032). The distal diaphragm (1032) converts from the closed configuration depicted in FIG. 18 to the open configuration depicted in FIG. 19 with increased pressure in the distal drug chamber (42). In some embodiments, the distal diaphragm (1032) is configured to convert from the closed configuration to the open configuration when a pressure in the distal drug chamber (42) is equal to or greater than approximately 10 psi. The distal diaphragm (1032) is configured such that the distal diaphragm (1032) exerts minimal resistance on fluid flow from the distal drug chamber (42) through the proximal and distal openings (1054, 1034) when the distal diaphragm (1032) is in the open configuration.

The inner member (1050) defines an outer proximally extending cylindrical member (1058) and the outer member (1030) defines an inner proximally extending cylindrical member (1046). The inner proximally extending cylindrical member (1046) is disposed coaxially around a portion of the elongate fluid conveying member/needle member (50). The outer proximally extending cylindrical member (1058) is disposed coaxially around a portion of the inner proximally extending cylindrical member (1046).

Figure 20:
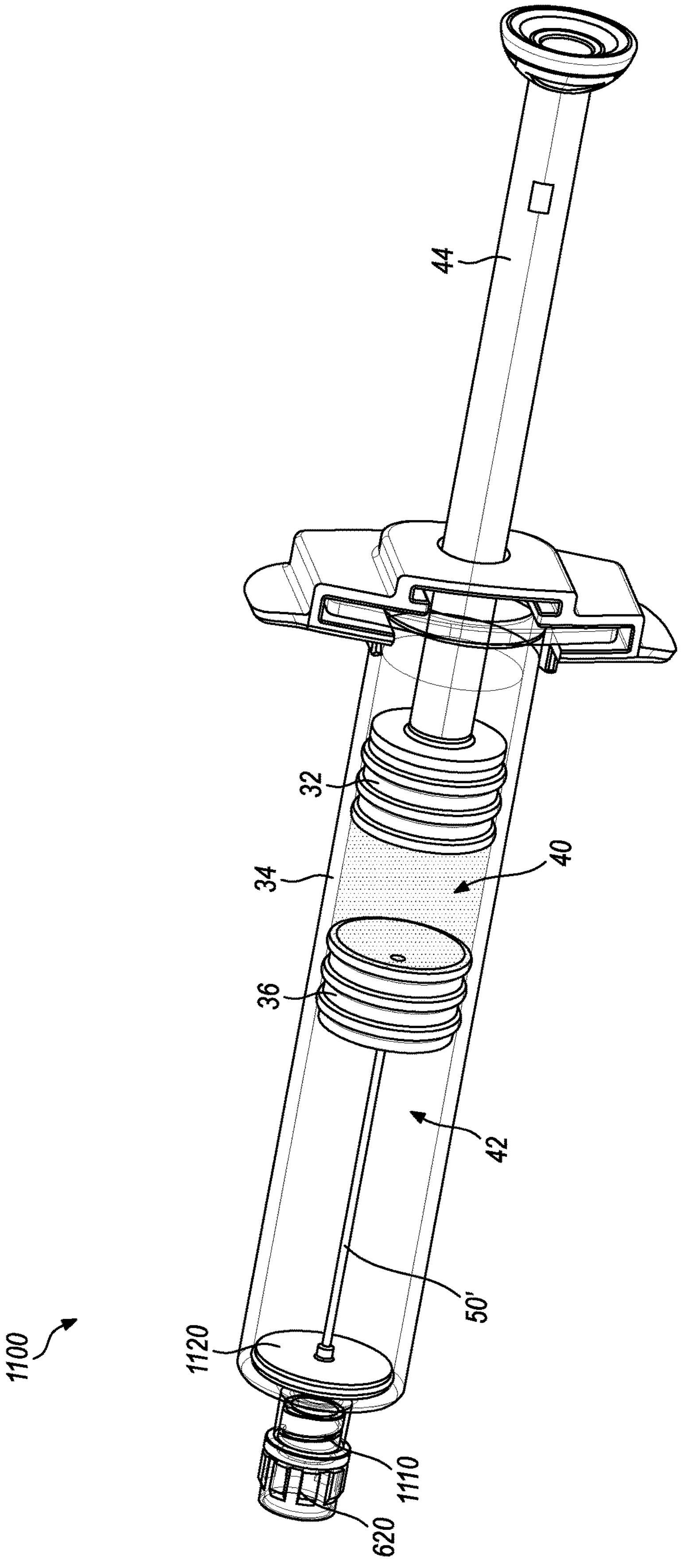
FIGS. 20 and 21 are perspective and detailed perspective views illustrating various aspects of syringe based dual chamber injection systems according to some embodiments.
Figure 21:
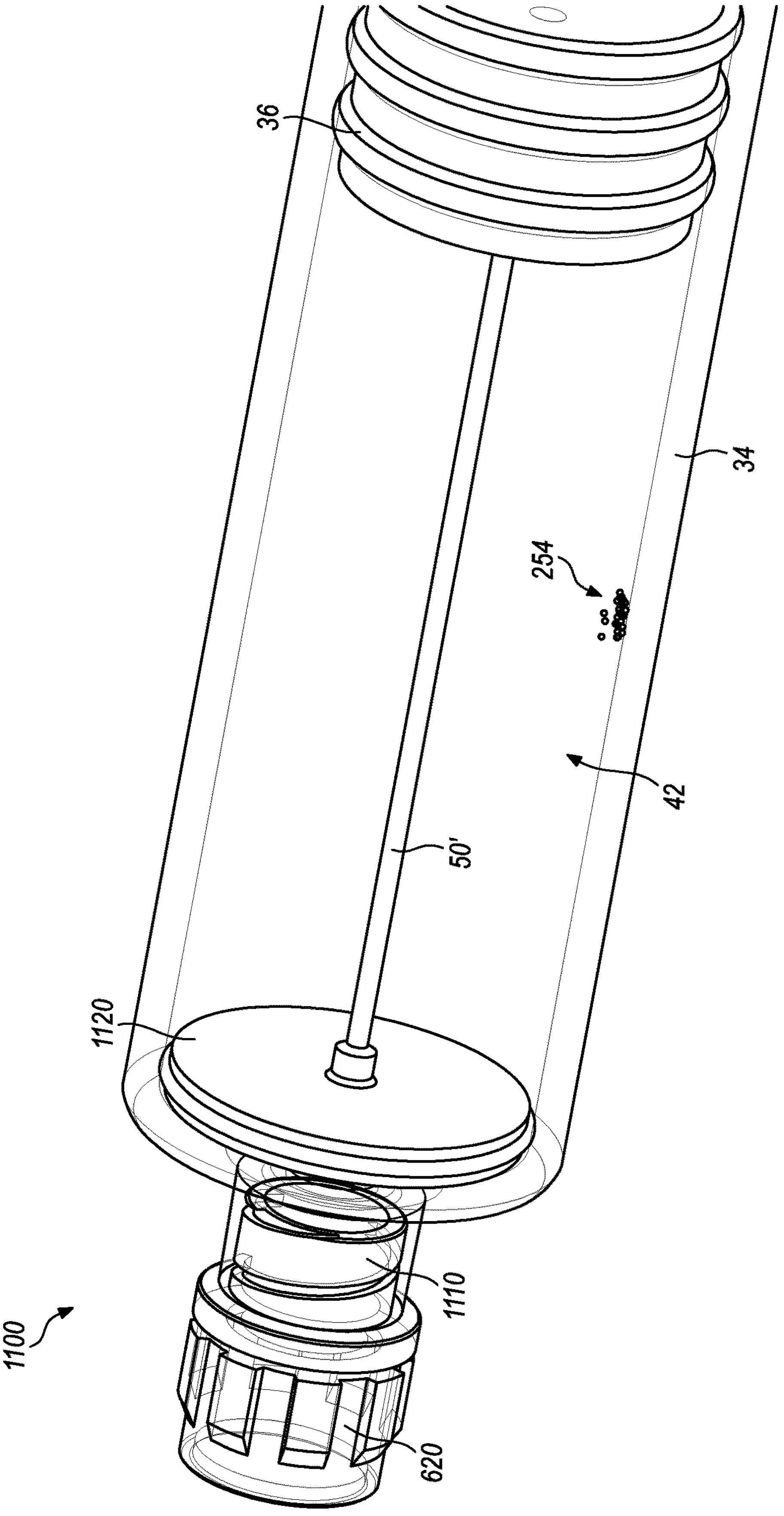

FIGS. 20 and 21 depict a dual chamber injection system (1100) having a valve (1120) disposed therein according to some embodiments. Similar to the dual chamber injection systems depicted in FIGS. 6A to 7P, the dual chamber injection system (1100) includes an injection system body (34), proximal and distal stopper members (32, 36), a plunger member (44), and an elongate fluid conveying member (50'). The proximal and distal stopper members (32, 36) together with the injection system body (34) form proximal and distal drug chambers (40, 42) as described herein. The proximal and distal drug chambers (40, 42) are prefilled with a liquid first medicine component and a non-liquid second medicine component (not shown for clarity; see 252, 254 in FIGS. 6A and 6B and 254 in FIG. 21). The elongate fluid conveying member (50') defines a middle opening (52) fluidly coupled through a fluid conveying interior to an open distal end of the elongate fluid conveying member (50') thereby forming a flow path through the elongate fluid conveying member (50').

The injection system body (34) includes a distal needle interface (1110) at a distal end thereof. In some embodiments, the distal needle interface (1110) may be a Luer connector. The distal needle interface (1110) may have many small spaces formed therein. If non-liquid second medicine component moves into some of the small spaces in the distal needle interface (1110), the non-liquid second medicine component may clog these small spaces and prevent any liquid from exiting the injection system body (34). The non-liquid second medicine component in these small spaces may not dissolve, thereby changing the final concentration of medicines in the mixed medicine. The dual chamber injection system (1100) depicted in FIGS. 20 and 21 is in a storage/transport configuration in which the distal needle interface (1110) is sealed with a cap (620).

The valve (1120) may perform one, two, three, or all of four functions described below. First, the valve (1120) may minimize and/or eliminate movement of the non-liquid second medicine component into the distal needle interface (1110) during assembly and storage of the injection system (1100). Second, the valve (1120) may center and stabilize the elongate fluid conveying member (50'), thereby facilitating piercing of the distal stopper member (36) by the elongate fluid conveying member (50'). Third, the valve (1120) may minimize and/or eliminate drug loss during shaking mixing from a vented injection (see FIG. 26). Fourth, in vented injection systems (1100) where the distal needle interface (1110) is open to the atmosphere to allow the escape of air during liquid transfer from the proximal chamber (40) to the distal chamber (42), the valve (1120) may prevent loss of the mixed medicine from the opening in the distal needle interface (1110) during shaking and mixing of the medicine components (see FIGS. 25 and 26). This fourth function prevents drug loss and protects the environment from toxic drugs. These valve functions, especially the third and fourth functions, facilitate the drug components in the proximal and distal chambers (40, 42) to be fully mixed before the mixed medicine is ejected distally out of the injection system body (34) through the distal needle interface (1110) (e.g., into either a medication bag or a needle).

Figure 22:
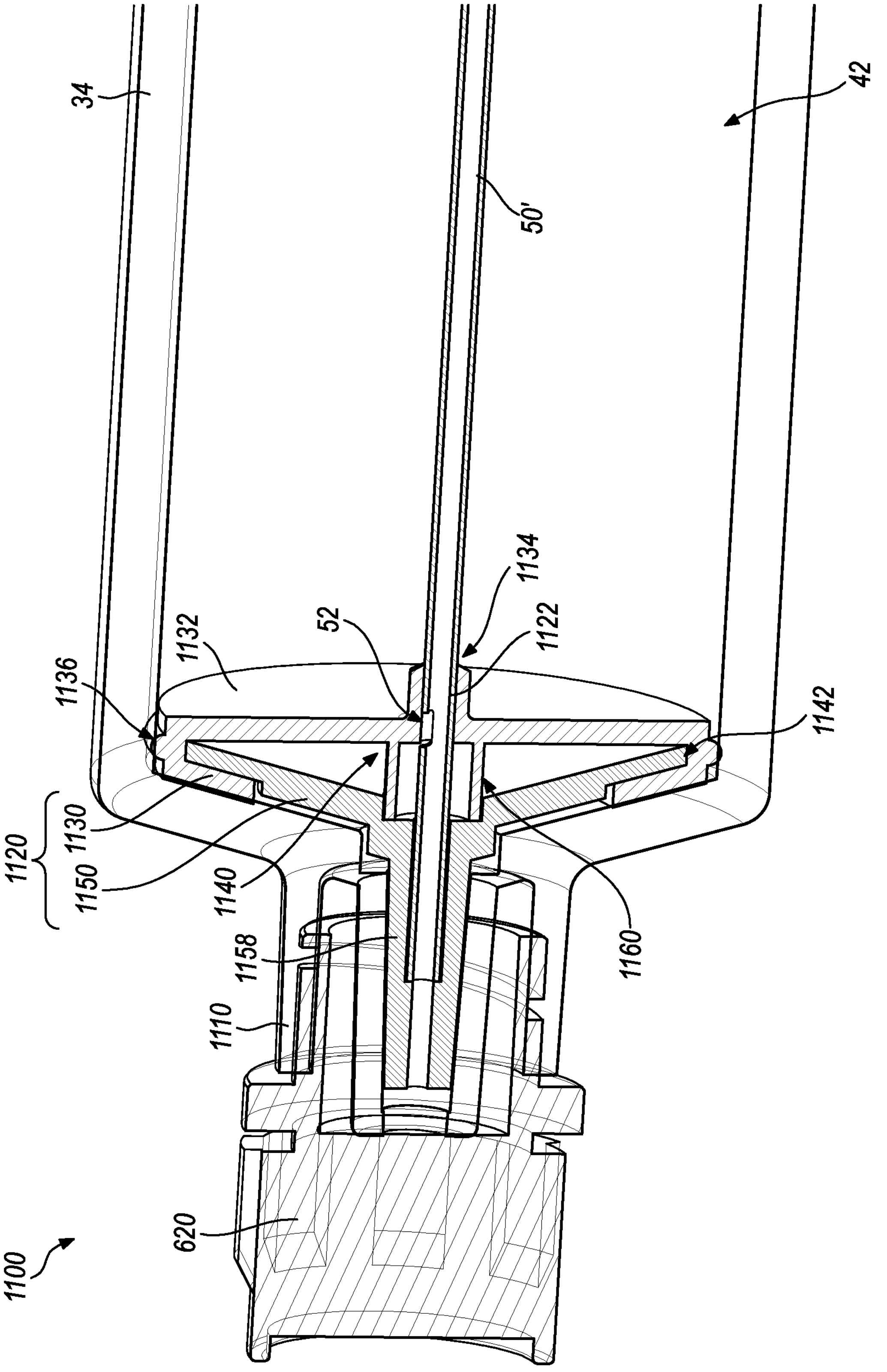
FIGS. 22 to 24 are detailed longitudinal cross-sectional views illustrating various aspects of syringe based dual chamber injection systems according to some embodiments.

FIG. 22 depicts the injection system (1100) and the valve (1120) in greater detail in a closed configuration in which flow between the distal drug chamber (42) and the middle opening (52) of the elongate fluid conveying member (50') is prevented. The valve (1120) may be formed from an elastic material. The valve (1120) includes an outer member (1130) and an inner member (1150). The outer member (1130) may be formed from an elastic material, and the inner member (1150) may be formed from a rigid material. The elastic material forming the outer member (1130) may be one or more of the following materials: rubber, butyl rubber, chlorobutyl rubber, bromobutyl rubber, thermoplastic elastomer, silicone rubber, thermoplastic, Polytetrafluoroethylene (PTFE), thermoset plastic. The outer member (1130) may be coated with a lubricious polymer such as PTFE, silicone oil, and/or other lubricious coatings. The rigid material forming the inner member (1150) may be one or more of the following materials: polymer, metal, glass, ceramic, hard durometer rubber, stainless steel, titanium, glass coated polymer, ceramic coated polymer, cyclic olefin copolymer (COC), cyclic olefin polymer (COP). The inner member (1150) may be coated with a lubricious polymer such as PTFE, silicone oil, and/or other lubricious coatings.

The outer member (1130) includes a distal diaphragm (1132) that defines a distal opening (1134) therein. In the embodiment depicted in FIG. 22, the distal opening (1134) is in an approximate center of the distal diaphragm (1132). The outer member (1130) also includes a seal (1122) around the diaphragm opening (1134) and configured to prevent fluid flow from the distal drug chamber (42) through the middle opening (52) of the elongate fluid conveying member (50') when the elastic diaphragm (1132) is in the closed configuration depicted in FIG. 22. The outer member (1130) further includes an outward annular member (1136) configured to form a fluid-tight seal between the valve (1120) and an inner surface of the injection system body (34). Moreover, the outer member (1130) includes a distally extending support member (1160) to position the elastic diaphragm (1132) proximally away from a proximal surface of the inner member (1150) to provide a space (1140) into which the elastic diaphragm (1132) may deflect. The outer member (1130) also defines an annular groove (1142) configured to secure the inner member (1150) in the outer member (1130). In the closed configuration depicted in FIG. 22, the elastic diaphragm (1132) is disposed proximal of the middle opening (52) in the elongate fluid conveying member (50'), thereby providing a fluid tight seal separating the middle opening (52) from the distal drug chamber (42). The elastic diaphragm (1132) is configured/biased to be in the closed configuration depicted in FIG. 22 when no external forces are acting thereon.

The inner member (1150) includes a distally extending member (1158) configured to form an frictional fit in the distal needle interface (1110). The frictional fit between the distally extending member (1158) and the inner surface of the distal needle interface (1110) couples the inner member (1150) and the valve (1120) to the injection system body (34).

Figure 23:
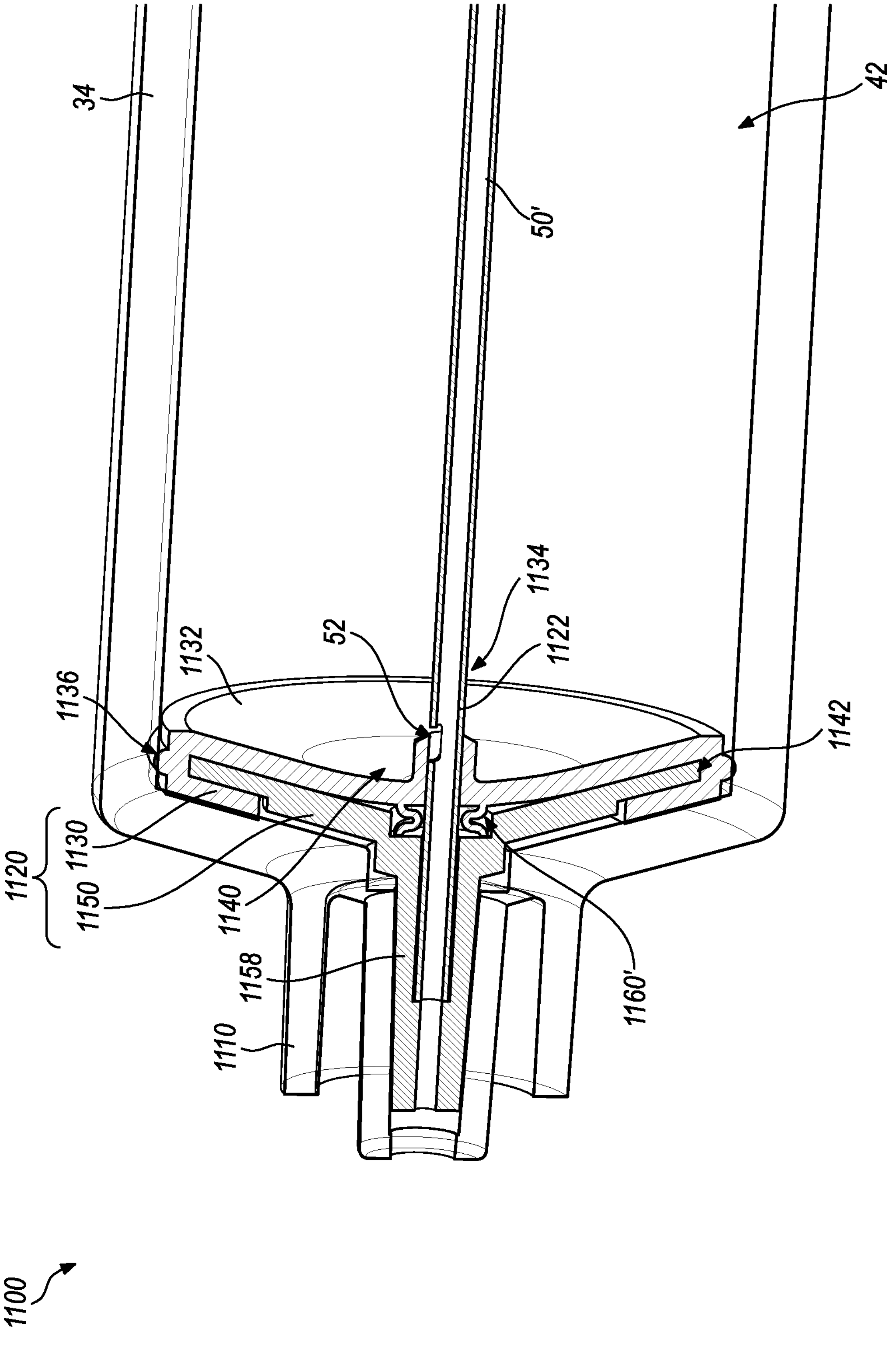

FIG. 23 depicts the injection system (1100) and the valve (1120) in an open configuration in which flow between the distal drug chamber (42) and the middle opening (52) of the elongate fluid conveying member (50') is enabled. In the open configuration, the distally extending support member (1160') of the outer member (1130) buckles/collapses/shortens to allow the elastic diaphragm (1132) to deform/deflect distally over the middle opening (52) thereby opening a flow path between the distal drug chamber (42) and the middle opening (52) of the elongate fluid conveying member (50'). The elastic diaphragm (1132) converts from the closed configuration depicted in FIG. 22 to the open configuration depicted in FIG. 23 with increased pressure in the distal drug chamber (42). In some embodiments, the elastic diaphragm (1132) is configured to convert from the closed configuration to the open configuration when a pressure in the distal drug chamber (42) is equal to or greater than approximately 10 psi. The elastic diaphragm (1132) is configured such that the elastic diaphragm (1132) exerts minimal resistance on fluid flow from the distal drug chamber (42) through the middle opening (1152) when the elastic diaphragm (1132) is in the open configuration. The cap (680) has also been removed from the distal needle interface (1110) to complete a flow path between the distal drug chamber (42) and an exterior of the injection system (1100).

Figure 25:
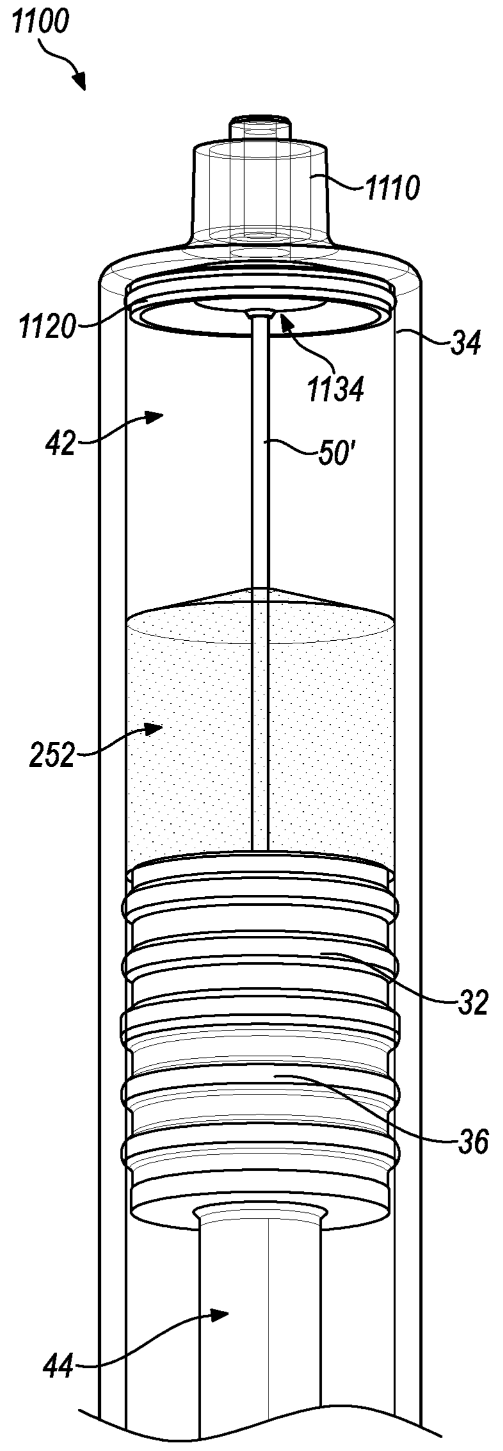
FIGS. 25 to 27 are detailed perspective views depicting various steps in an injection method using a syringe based dual chamber injection systems according to some embodiments.

In some embodiments, the injection system (1100) and the valve (1120) are in the open configuration depicted in FIG. 23 to vent air/pressure that builds up in the distal drug chamber (42) as fluid is transferred from the proximal drug chamber (40) to the distal drug chamber (42) (see FIG. 25). In some embodiments, the injection system (1100) and the valve (1120) are in the open configuration depicted in FIG. 23 to allow a mixed medicine/drug to be ejected from the distal drug chamber (42) (see FIG. 27).

Figure 24:
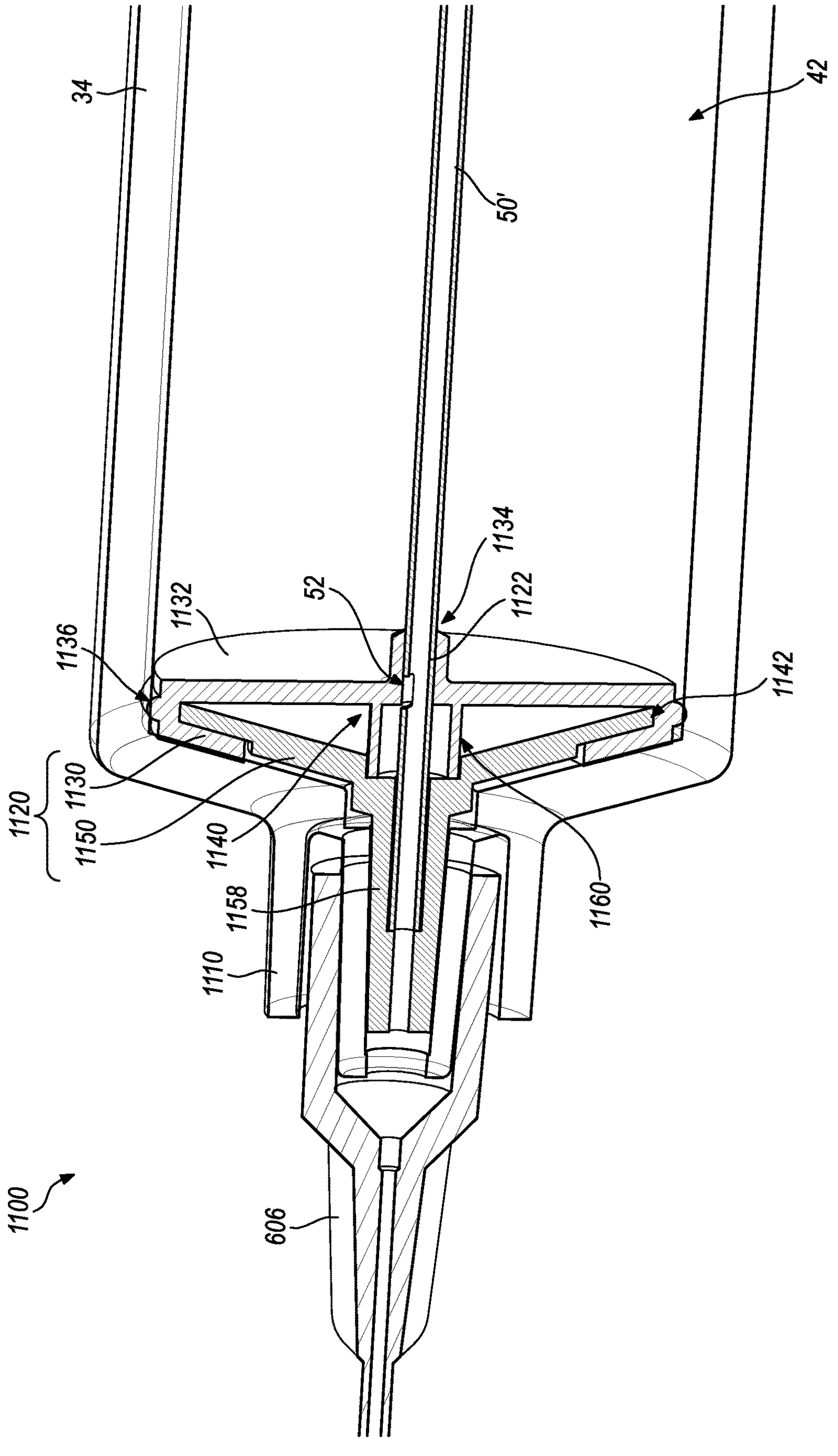

FIG. 24 depicts the injection system (1100) and the valve (1120) in greater detail in a closed configuration similar to that in FIG. 22. The difference between the injection systems (1100) depicted in FIGS. 22 and 24 is that the cap (680) has been replaced with a needle coupling assembly (606), which is coupled to the distal needle interface (1110) to complete a flow path between the distal drug chamber (42) and an exterior of the injection system (1100).

Figure 26:
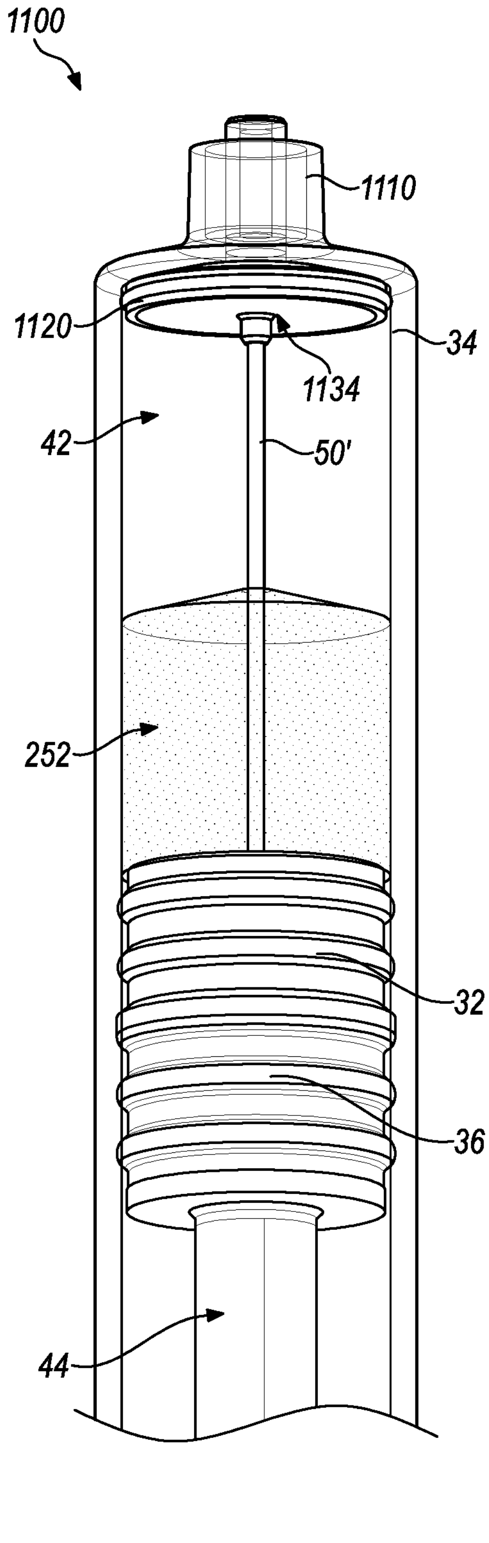
Figure 27:
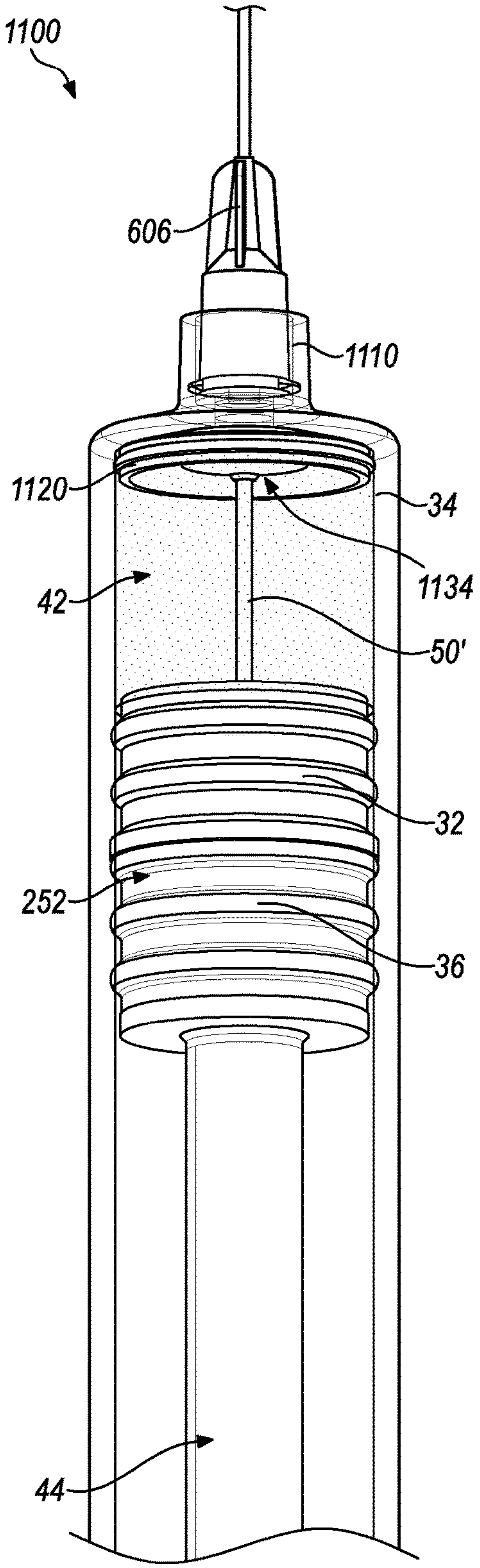
Figure 28:
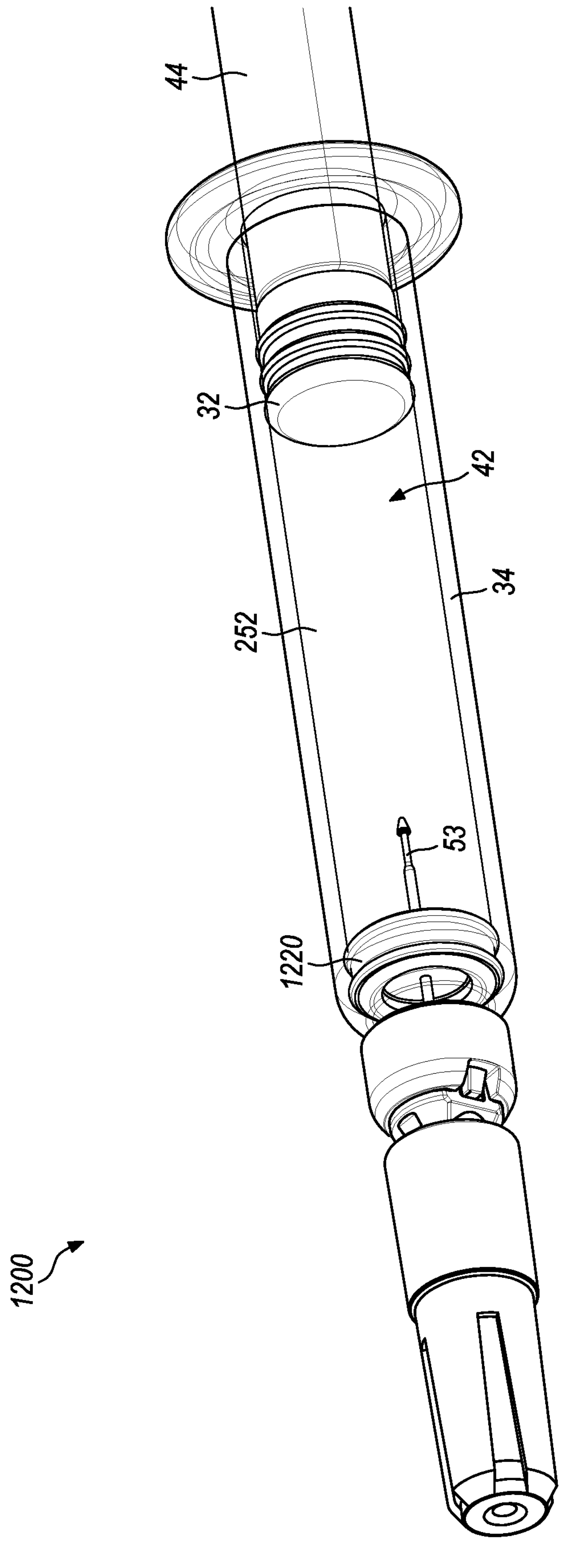
FIGS. 28, 29, and 31 are perspective and detailed perspective views of a syringe based injection system with a valve in closed (FIGS. 28 and 29) an open (FIG. 31) configurations according to some embodiments.

FIGS. 25 to 27 depict various steps in an injection method using the injection system (1100) depicted in FIGS. 20-24 according to some embodiments. In FIG. 25, the proximal stopper member (36) has been moved distally until the proximal drug chamber (40, see FIG. 20) is completely collapsed and the liquid first medicine component (252) therein has been transferred to the distal drug chamber (42). During fluid transfer from the proximal drug chamber (40) to the distal drug chamber (42), the increased pressure in the distal drug chamber (42) shortens the distally extending support member (1160') of the outer member (1130), as shown in FIG. 23. This allows the air/pressure in the distal drug chamber (42) to vent to an exterior of the injection system (1100) through the elongate fluid conveying member (50').

In FIG. 26, the fluid transfer from the proximal drug chamber (40) to the distal drug chamber (42) is complete, and the pressure in the distal drug chamber (42) returns to normal (i.e., atmospheric/external pressure). This allows the distally extending support member (1160') of the outer member (1130) shown in FIG. 23 to spring back/lengthen to the distally extending support member (1160) shown in FIGS. 22 and 24, thereby closing the valve (1120). This closed configuration allows the liquid first medicine component (252) and the non-liquid second medicine component (not shown) in the distal drug chamber (42) to be mixed while minimizing unintended expulsion of the components from the distal drug chamber (42).

In FIG. 27, a needle coupling assembly (606) has been coupled to the distal needle interface (1110) and the excess air has been expelled from the distal drug chamber (42). The increased pressure in the distal drug chamber (42) shortens the distally extending support member (1160') of the outer member (1130), as shown in FIG. 23. This allows the air/pressure in the distal drug chamber (42) to vent to an exterior of the injection system (1100) through the elongate fluid conveying member (50') and allowed ejection of a mixed medicine from the distal drug chamber (42).

FIGS. 28 to 32 depict an injection system (1200) having a valve (1220) disposed therein according to some embodiments. The injection system (1200) includes an injection system body (34), a stopper member (32), a plunger member (44), and a needle assembly, which includes a needle proximal end (53) and a needle joining member (54). The stopper member (32) together with the injection system body (34) form a chamber (42). The chamber (42) may be prefilled with an injectable fluid (252). The needle proximal end (53) and the needle joining member (54) defines a middle opening (52) fluidly coupled through an interior of the needle joining member (54) to an open distal end of the needle assembly thereby forming a flow path through the needle assembly.

Figure 29:
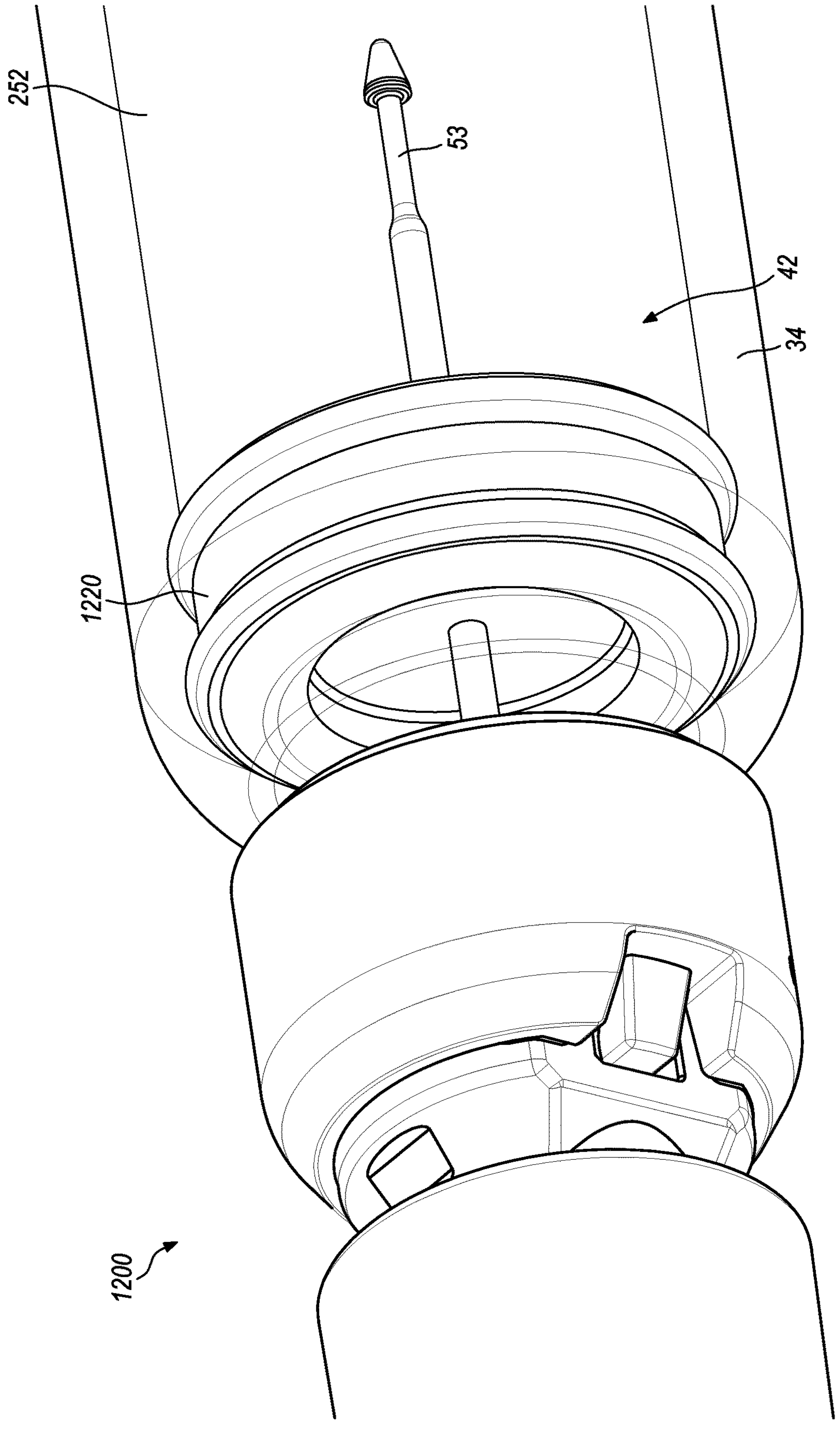
Figure 30:
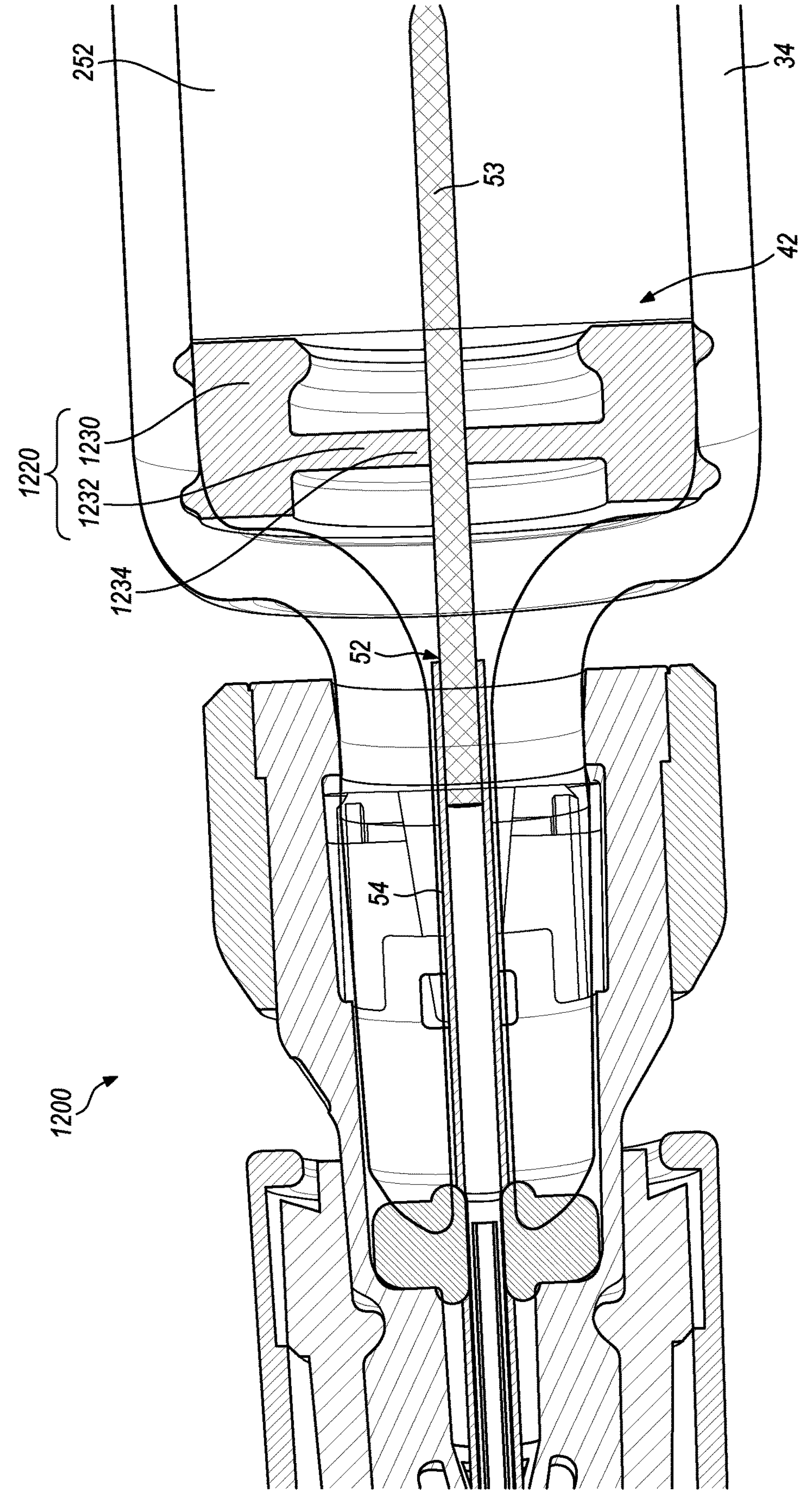
FIGS. 30 and 32 are detailed longitudinal cross-sectional views of a syringe based injection system with a valve in closed (FIG. 30) an open (FIG. 32) configurations according to some embodiments.

As shown in FIGS. 29 and 30, the valve (1220) includes an outer member (1230) and an inner member (1232). The inner member (1232) is an elastic diaphragm having a circumferentially inward facing surface (1234). The inner and/or outer members (1232, 1234) may be constructed from elastic material, which may be one or more of the following materials: rubber, butyl rubber, chlorobutyl rubber, bromobutyl rubber, thermoplastic elastomer, silicone rubber, thermoplastic, Polytetrafluoroethylene (PTFE), thermoset plastic. The inner and/or outer members (1232, 1234) may be coated with a lubricious polymer such as PTFE, silicone oil, and/or other lubricious coatings.

When the injectable fluid (252) in the chamber (42) is at a relatively low pressure (e.g., less than about 25 psi), the valve (1220)/inner member/elastic diaphragm (1232) is in a closed configuration as shown in FIGS. 29 and 30. In the closed configuration, the inner member/elastic diaphragm (1232) is essentially flat and is configured to form a fluid tight seal against a circumferentially outward surface of the needle proximal end (53). The fluid tight seal prevents the injectable fluid (252) from flowing from the chamber (42) to the middle opening (52) in the needle assembly (e.g., during transport and storage of the injection system (1200)).

Figure 31:
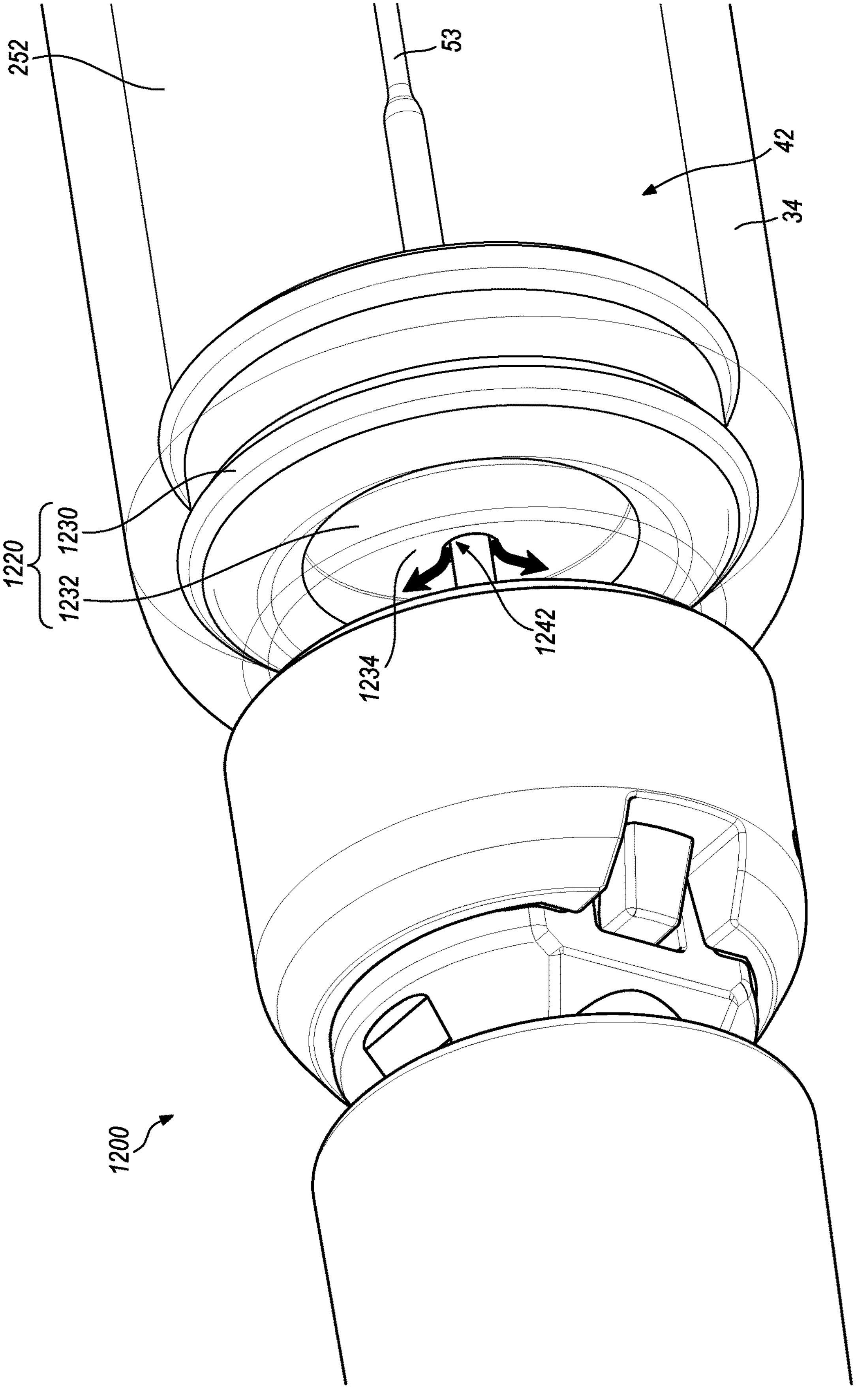
Figure 32:
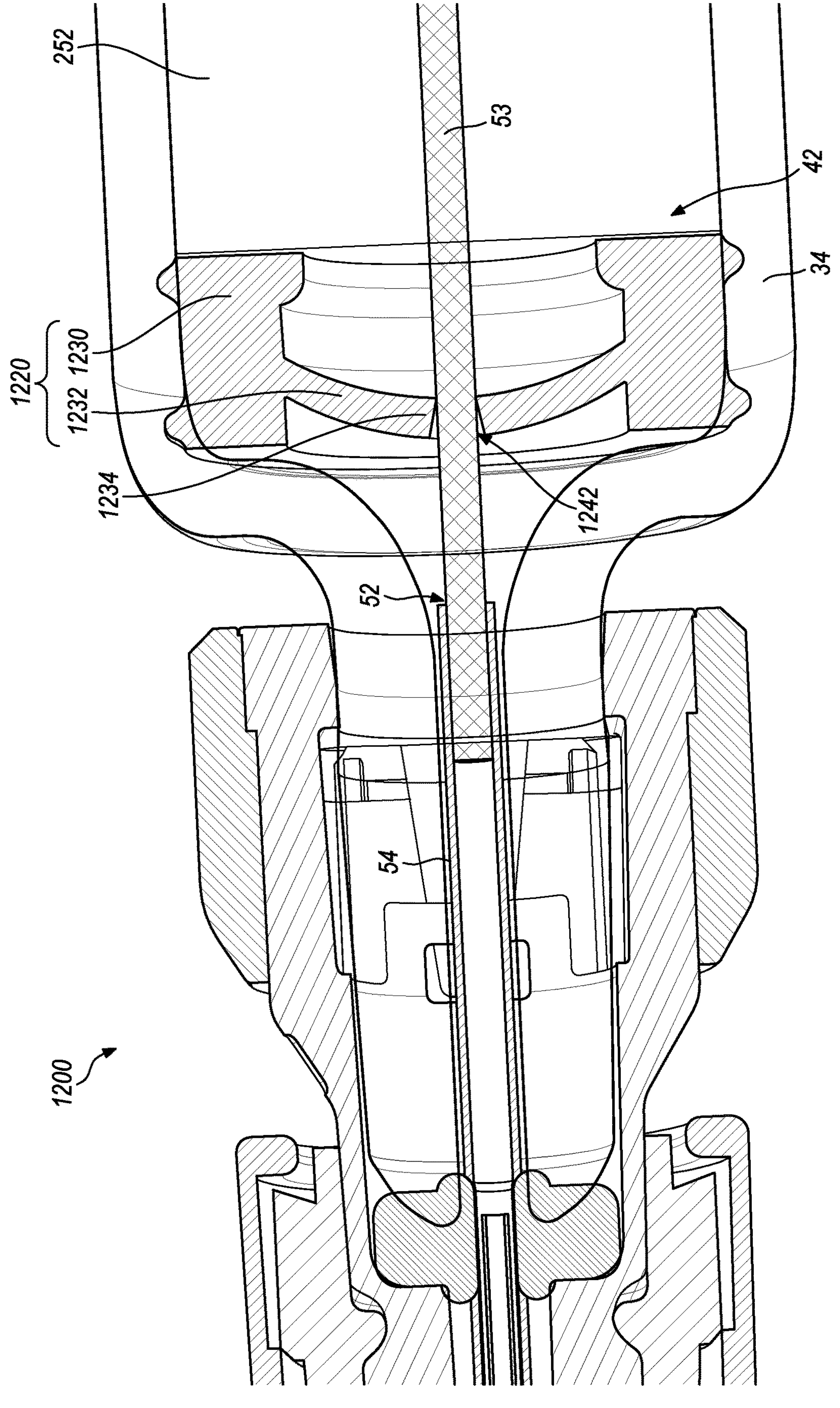

As shown in FIGS. 31 and 32, when the injectable fluid (252) in the chamber (42) is pressurized by application of a distally directed force to the plunger member (44) and the stopper member (32) attach thereto (e.g., greater than or equal to about 25 psi), the valve (1220)/inner member/elastic diaphragm (1232) moves from the closed configuration shown in FIGS. 29 and 30 to the open configuration shown in FIGS. 31 and 32. In the open configuration, the pressure in the chamber (42) elastically deforms the inner member/elastic diaphragm (1232) distally relative to the needle assembly, thereby eliminating the seal between the chamber (42) and the middle opening (52) in the needle assembly (e.g., during injection). When the inner member/elastic diaphragm (1232) is elastically deformed distally relative to the needle assembly, the circumferentially inward facing surface (1234) moves away from the needle proximal end (53), thereby opening a flow path (1242) between the inner member/elastic diaphragm (1232) and the needle proximal end (53). With the valve (1220) in the open configuration, the injectable fluid (252) can flow from the chamber (42) through the flow path (1242) to the middle opening (52) in the needle assembly for injection.

The valve (1220) depicted in FIGS. 28 to 32 adds only one extra part (e.g., the valve (1220)) to create a sealed syringe/injection system (1200). The valve (1220) can create sealed versions of both dual chamber and single-chamber injection systems. Further, because the valve (1220) does not need to be aligned with any opening on the needle assembly, the valve (1220) can be used with larger tolerances in the parts of the injection system (1200) and in assembly of the system (1200).

Figure 33:
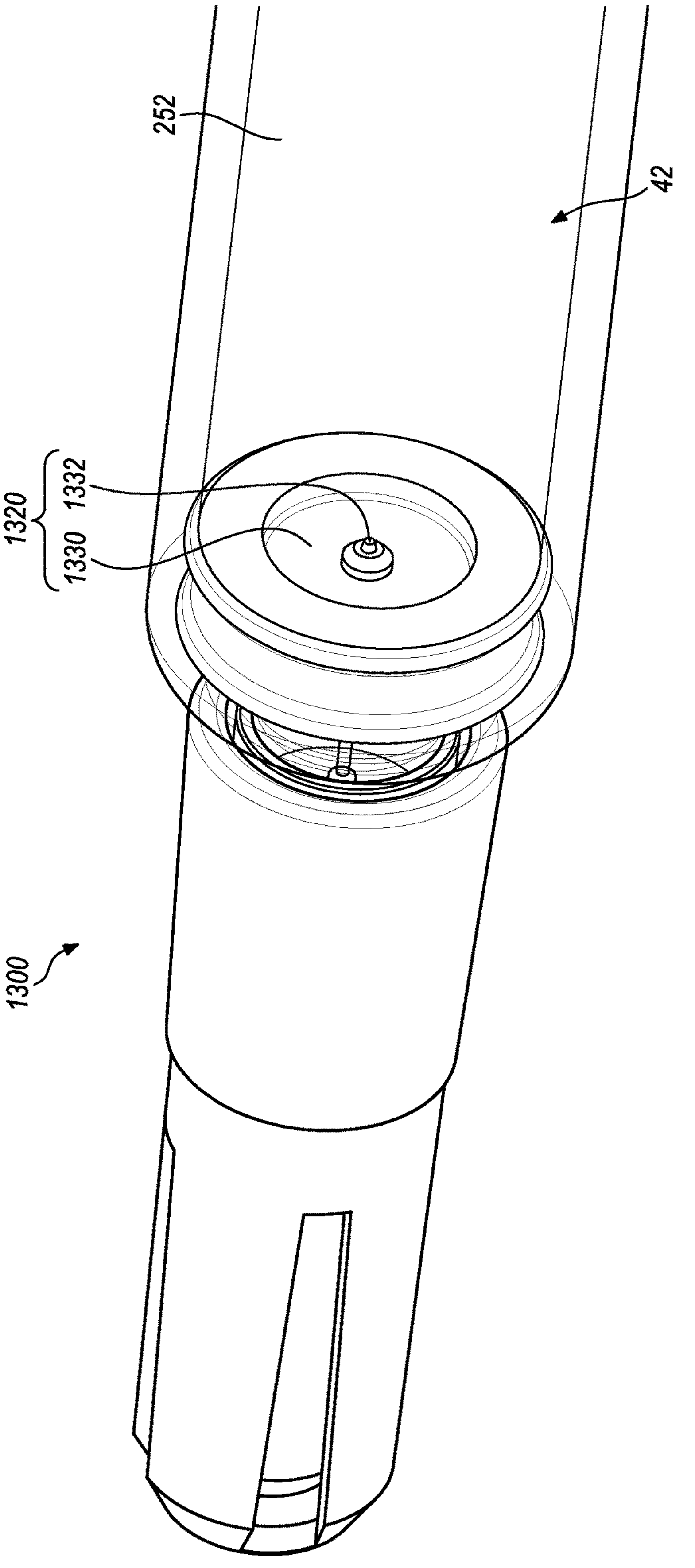
FIGS. 33 to 35 are perspective and detailed perspective views of a syringe based injection system with a valve in closed (FIGS. 33 and 34) an open (FIG. 35) configurations according to some embodiments.
Figure 34:
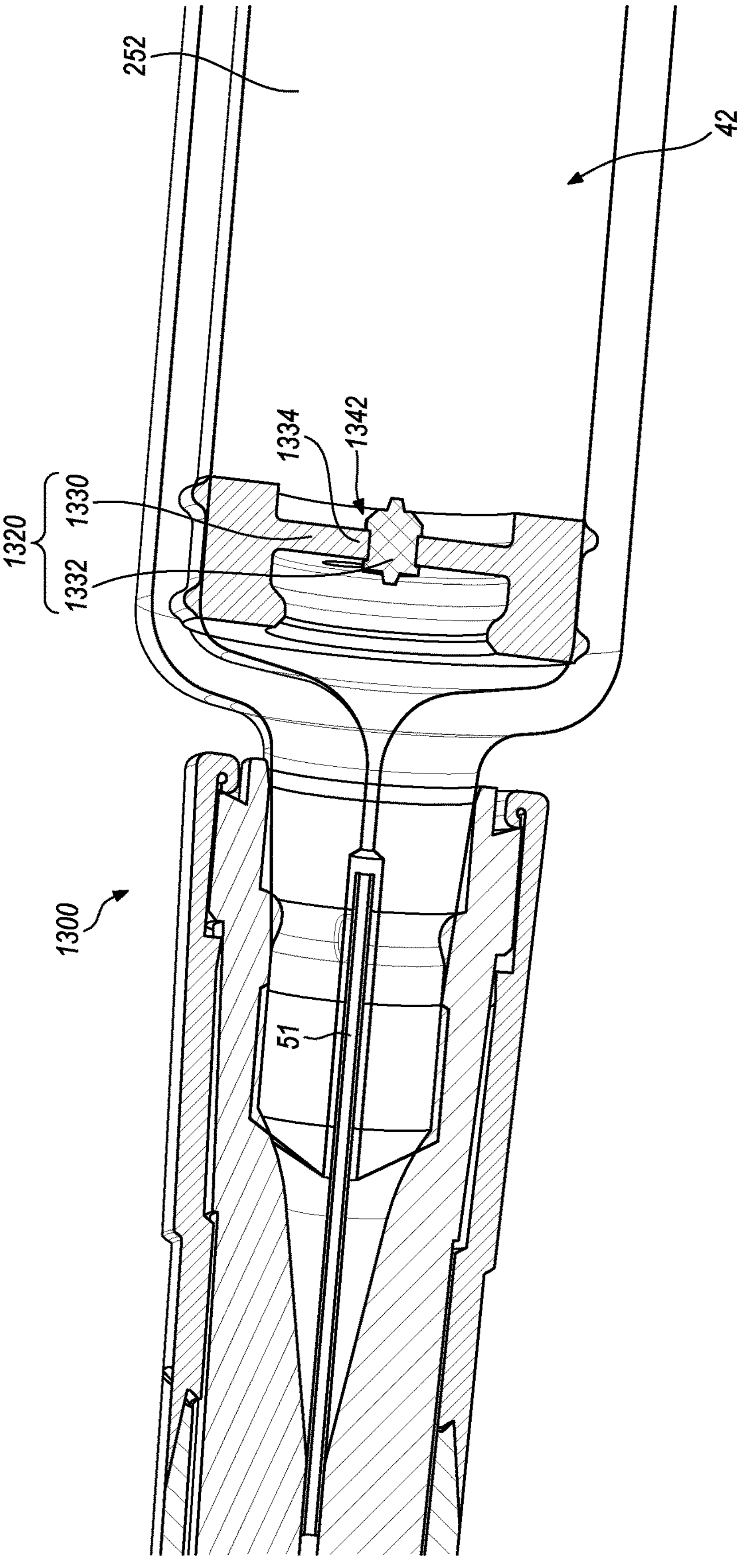
Figure 35:
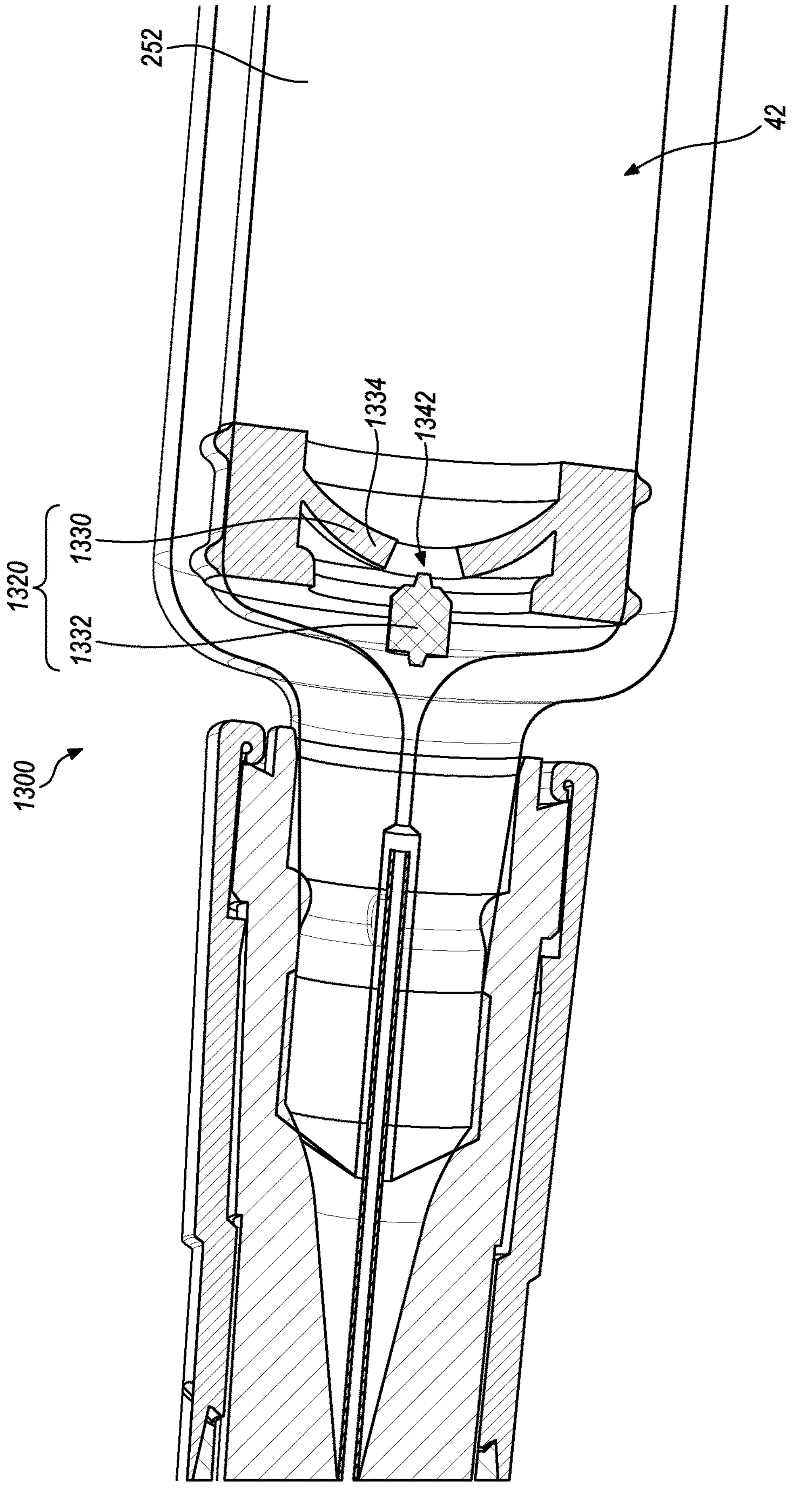

FIGS. 33 to 35 depict an injection system (1300) having a valve (1320) disposed therein according to some embodiments. The injection system (1300) includes an injection system body (34), a stopper member, a plunger member, and a needle (51). The stopper member (32) together with the injection system body (34) form a chamber (42). The chamber (42) may be prefilled with an injectable fluid (252). The needle (51) has open proximal and distal ends.

As shown in FIGS. 33 and 34, the valve (1320) includes an elastic diaphragm (1330) having a circumferentially inward facing surface (1334) that defines a central diaphragm opening (1342). The valve (1320) also includes a plug member (1332) configured to be disposed in the central diaphragm opening (1342) when the valve is in a closed configuration as shown in FIGS. 33 and 34 and described below. When the injectable fluid (252) in the chamber (42) is at a relatively low pressure (e.g., less than about 30 psi), the valve (1320)/elastic diaphragm (1330) is in the closed configuration as shown in FIGS. 33 and 34. In the closed configuration, the inner elastic diaphragm (1330) is essentially flat and is configured to form a fluid tight seal against a circumferentially outward surface of the plug member (1332). The fluid tight seal prevents the injectable fluid (252) from flowing from the chamber (42) to the proximal opening of the needle (51) (e.g., during transport and storage of the injection system (1300)). The elastic diaphragm (1330) may be constructed from one or more of the following materials: rubber, butyl rubber, chlorobutyl rubber, bromobutyl rubber, thermoplastic elastomer, silicone rubber, thermoplastic, Polytetrafluoroethylene (PTFE), thermoset plastic. The elastic diaphragm (1330) may be coated with a lubricious polymer such as PTFE, silicone oil, and/or other lubricious coatings. The rigid material forming the plug member (1332) may be one or more of the following materials: polymer, metal, glass, ceramic, hard durometer rubber, stainless steel, titanium, glass coated polymer, ceramic coated polymer, cyclic olefin copolymer (COC), cyclic olefin polymer (COP). The inner member may be coated with a lubricious polymer such as PTFE film, silicone oil, and/or other lubricious coatings.

As shown in FIG. 35, when the injectable fluid (252) in the chamber (42) is pressurized by application of a distally directed force to the plunger member (44) and the stopper member (32) attach thereto (e.g., greater than or equal to about 30 psi), the elastic diaphragm (1330) moves from the closed configuration shown in FIGS. 33 and 34 to the open configuration shown in FIG. 35. In the open configuration, the pressure in the chamber (42) elastically deforms the elastic diaphragm (1330) distally away from the stopper member, thereby eliminating the seal between the chamber (42) and the proximal opening of the needle (51) (e.g., during injection). When the elastic diaphragm (1330) is elastically deformed distally away from the stopper member, the circumferentially inward facing surface (1334) moves away from the plug member (1332), thereby releasing the plug member (1332) from the diaphragm opening (1342) and opening the diaphragm opening (1342). With the valve (1320) in the open configuration, the injectable fluid (252) can flow from the chamber (42) through the diaphragm opening (1342) to the proximal opening of the needle (51) for injection.

The plug member (1332) include a smaller radius portion disposed longitudinally between proximal and distal larger radius portions in some embodiments. In an alternative embodiment, the plug member (1332) may be a ball bearing sized and shaped to close the diaphragm opening (1342) with the valve (1320) in the closed configuration and to be dislodged from the diaphragm opening (1342) with the valve (1320) in the open configuration. In some embodiments, the plug member (1332) has a diameter of approximately 0.050 inches, and a cross-sectional surface area of approximately 0.002 square inches the proximal direction. In such embodiments, approximately 30 psi of pressure applied to the valve (1320) causes the deflection of the diaphragm (1330) shown in FIG. 35. The deflection of the diaphragm (1330) allows a thin pressurized film of injectable fluid (252) to flow between the diaphragm (1330) and the plug member (1332), which reduces friction between these two parts to near zero and allow the shear forces of the injectable fluid (252) flowing past the plug member (1332) to dislodge the plug member (1332) from the diaphragm opening (1342) as shown in FIG. 35.

In another embodiment the plug member (1332) may have proximal and/or distal engagement ribs extending from an outer diameter to increase the mechanical interference with the elastic diaphragm (1330) to increase the pressure required to dislodge the plug member (1332). While the valve (1320) is shown in a single chamber injection system (1330), the valve (1320) can be used to create sealed versions of both dual chamber and single-chamber injection systems.

The valve (1320) shown in FIGS. 33 to 35 mitigates the increase in required operating pressure with age of the injection systems, which can become undesirably large with valves including elastic polymer/hard polymer interfaces that adhere to each other over time. The valve (1320) includes an elastic polymer diaphragm (1330) and a metal plug member (1334), and the interaction between these parts generate minimal increases in operating pressure with age of the injection system (1300).

The predetermined amount of force to convert a valve/diaphragm from a closed configuration to an open configuration can be modulated to accommodate a combination of the system function requirements and the aesthetic impression on the user. If the activation force is too low, it may work, but be too difficult for the user to apply the force lightly enough, and the user may overshoot. If the force is too high, the user may find that it is "too hard" to activate the system. Fortunately, the predetermined amount of force can be "tune" a range by modifying various component characteristics.

In some embodiments, various aspects of the valves (820, 920, 1020, 1120, 1220, 1320) disclosed herein may be modified to tune the amount of force/pressure required to open the valves (820, 920, 1020, 1120, 1220, 1320). These aspects include, but are not limited to: (1) the outer diameter of the diaphragms (832, 932, 1032, 1132, 1232, 1330); (2) the thickness of the diaphragms (832, 932, 1032, 1132, 1232, 1330); (3) the amount of interference between the plug member (1332) and the elastic diaphragm (1330). The amount of interference between the plug member (1332) and the elastic diaphragm (1330) can be modified by adding protrusions/bumps to the circumferentially inward facing surface (1334) that defines the central diaphragm opening (1342) to increase the amount of interference and thereby the amount of force/pressure needed to dislodge/release the plug member (1332) to open the valve (1320).

While the embodiments described above include dual chamber safety injection systems, the scope of the claims also include other multiple chamber safety injection systems. For multiple chamber safety injection systems with more than two chambers, more than two stopper members are inserted into an injection system body (e.g., syringe body, cartridge body, etc.) to define a corresponding number of chambers.

While the prefilled dual chamber safety injection systems depicted and described herein include syringes with staked needles, the various configurations/embodiments described herein (e.g., serial injection, detent dual chamber, threaded plunger member, and shielded and vented needle cover) can be used with cartridges an auto injector, and injection systems with Luer connectors, transfer pipes, and no needles such as those described in U.S. Utility patent application Ser. Nos. 15/801,281 and 15/801,259, which were previously incorporated by reference herein.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, ETFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. An injection system, comprising:

an injection system body defining a proximal opening at a proximal end thereof and a distal needle interface at a distal end thereof;

proximal and distal stopper members disposed in the injection system body, forming a proximal drug chamber between the proximal and distal stopper members and a distal drug chamber between the distal stopper member and the distal end of the injection system body;

a plunger member configured to insert the proximal stopper member relative to the injection system body; and a valve forming an openable barrier between the distal needle interface and the distal drug chamber, the valve comprising an outer member comprising a distal diaphragm which defines a distal opening therein, and an inner member comprising a distally extending member configured to fit in and interfere with the distal opening in the distal diaphragm when the distally extending member is disposed in the distal opening in the distal diaphragm, wherein the distal diaphragm is configured to elastically deform distally away from the inner member with increased pressure in the distal drug chamber to allow flow from the distal drug chamber to the distal needle interface, wherein the distal diaphragm is biased in a closed configuration in which the distal diaphragm is disposed against the inner member to position the distal opening in the distal diaphragm around the distally extending member of the inner member unless the distal diaphragm is deformed in an open configuration in which the distal diaphragm is disposed away from the inner member, wherein the inner member defines an annular groove, and wherein the outer member further comprises a radially inward annular member configured to interfere with the annular groove in the inner member to secure the inner member in the outer member.

2. The system of claim 1, wherein the distal diaphragm is configured to convert from the closed configuration to the open configuration when a pressure in the distal drug chamber is equal to or greater than approximately 10 psi.

3. The system of claim 1, wherein when the distal diaphragm is in the open configuration, the distal diaphragm exerts minimal resistance on fluid flow from the distal drug chamber through the distal opening in the distal diaphragm to the distal needle interface.

4. The system of claim 1, the outer member further comprising a plurality of radially outward annular members configured to form a fluid-tight seal between the outer member and an inner surface of the injection system body.

5. The system of claim 1, the outer member further comprising a distally extending ring configured to provide a space for the distal diaphragm to deform distally to convert from the closed configuration to the open configuration.

6. The system of claim 1, the outer member defining an annular groove configured to secure the inner member in the outer member.

7. The system of claim 1, wherein the inner member defines a proximal opening, and wherein the distal diaphragm interferes fluid flow through with the proximal opening when the distal diaphragm is in the closed configuration.

8. The system of claim 1, wherein the outer member is formed from a deformable material, and wherein the inner member is formed from a rigid material.

9. An injection system, comprising:

an injection system body defining a proximal opening at a proximal end thereof and a distal needle interface at a distal end thereof;

proximal and distal stopper members disposed in the injection system body, forming a proximal drug chamber between the proximal and distal stopper members and a distal drug chamber between the distal stopper member and the distal end of the injection system body;

a plunger member configured to insert the proximal stopper member relative to the injection system body; and a valve forming an openable barrier between the distal needle interface and the distal drug chamber, the valve comprising an outer member comprising a distal diaphragm which defines a distal opening therein, and an inner member comprising a distally extending member configured to fit in and interfere with the distal opening in the distal diaphragm when the distally extending member is disposed in the distal opening in the distal diaphragm, wherein the distal diaphragm is configured to elastically deform distally away from the inner member with increased pressure in the distal drug chamber to allow flow from the distal drug chamber to the distal needle interface, wherein the distal diaphragm is biased in a closed configuration in which the distal diaphragm is disposed against the inner member to position the distal opening in the distal diaphragm around the distally extending member of the inner member unless the distal diaphragm is deformed in an open configuration in which the distal diaphragm is disposed away from the inner member, wherein the outer member further comprises a plurality of radially outward annular members configured to form a fluid-tight seal between the outer member and an inner surface of the injection system body, and wherein at least one pair of longitudinally adjacent radially outward annular members of the plurality of radially outward annular members defines a space therebetween.

10. An injection system, comprising:

an injection system body defining a proximal opening at a proximal end thereof and a distal needle interface at a distal end thereof;

proximal and distal stopper members disposed in the injection system body, forming a proximal drug chamber between the proximal and distal stopper members and a distal drug chamber between the distal stopper member and the distal end of the injection system body;

a plunger member configured to insert the proximal stopper member relative to the injection system body; and a valve forming an openable barrier between the distal needle interface and the distal drug chamber, the valve comprising an outer member comprising a distal diaphragm which defines a distal opening therein, and an inner member comprising a distally extending member configured to fit in and interfere with the distal opening in the distal diaphragm when the distally extending member is disposed in the distal opening in the distal diaphragm, wherein the distal diaphragm is configured to elastically deform distally away from the inner member with increased pressure in the distal drug chamber to allow flow from the distal drug chamber to the distal needle interface, wherein the distal diaphragm is biased in a closed configuration in which the distal diaphragm is disposed against the inner member to position the distal opening in the distal diaphragm around the distally extending member of the inner member unless the distal diaphragm is deformed in an open configuration in which the distal diaphragm is disposed away from the inner member, wherein the system further comprises a needle member removably coupled to the distal needle interface, wherein the inner member defines an outer proximally extending cylindrical member, and wherein the outer member defines an inner proximally extending cylindrical member disposed coaxially around a portion of the needle and at least partially coaxially within the outer proximally extending cylindrical member.

11. The system of claim 10, the outer member further comprising a distally facing funnel disposed adjacent the distal opening in the distal diaphragm.

12. An injection system, comprising:

an injection system body defining a proximal opening at a proximal end thereof and a distal needle interface at a distal end thereof;

proximal and distal stopper members disposed in the injection system body, forming a proximal drug chamber between the proximal and distal stopper members and a distal drug chamber between the distal stopper member and the distal end of the injection system body;

a plunger member configured to insert the proximal stopper member relative to the injection system body;

a fluid conveying member removably coupled to the distal needle interface and having a middle opening disposed adjacent a distal end of the syringe body; and a valve forming an openable barrier between the middle opening and the distal drug chamber, the valve comprising an elastic diaphragm defining a diaphragm opening therein and disposed around the fluid conveying member adjacent the middle opening therein, and a seal around the diaphragm opening configured to prevent fluid flow from the distal drug chamber through the middle opening of the fluid conveying member when the elastic diaphragm is in a closed configuration, wherein the elastic diaphragm is configured to elastically deform into an open configuration with increased pressure in the distal drug chamber to move the seal distally relative to the fluid conveying member to allow flow from the distal drug chamber through the middle opening of the fluid conveying member, wherein the valve further comprises a plurality of radially outward annular members configured to form a fluid-tight seal between the valve and an inner surface of the injection system body, and wherein at least one pair of longitudinally adjacent radially outward annular members of the plurality of radially outward annular members defines a space therebetween.

13. The system of claim 12, wherein the elastic diaphragm is biased in the closed configuration in which the seal is disposed around the fluid conveying member proximal of the middle opening unless the elastic diaphragm is deformed into the open configuration in which the elastic diaphragm is disposed at least partially distal of the middle opening.

14. An injection system, comprising:

an injection system body defining a proximal opening at a proximal end thereof and a distal needle interface at a distal end thereof;

a stopper member disposed in the injection system body, forming a drug chamber between the stopper member and the distal end of the injection system body;

a plunger member configured to insert the stopper member relative to the injection system body;

a needle hub assembly coupled to the distal needle interface, the needle hub assembly comprising a needle hub coupled to the distal needle interface, and a needle member removably coupled to the needle hub and having a middle opening disposed adjacent the distal end of the injection system body; and a valve forming an openable barrier between the middle opening and the drug chamber, the valve comprising an elastic diaphragm having a circumferentially inward facing surface defining a diaphragm opening therein and disposed around the needle member proximal of the middle opening therein, wherein the circumferentially inward facing surface is configured to form a seal around the with the needle member to prevent fluid flow from the drug chamber to the middle opening of the needle member when the elastic diaphragm is in a closed configuration, wherein the elastic diaphragm is configured to elastically deform into an open configuration with increased pressure in the drug chamber to deform the elastic diaphragm distally relative to the needle member to move the circumferentially inward facing surface away from the needle member to allow flow from the drug chamber to the middle opening of the needle member, wherein the valve further comprises a plurality of radially outward annular members configured to form a fluid-tight seal between the valve and an inner surface of the injection system body, and wherein at least one pair of longitudinally adjacent radially outward annular members of the plurality of radially outward annular members defines a space therebetween.

15. The system of claim 14, wherein the needle member is made from a metal.

16. An injection system, comprising:

an injection system body defining a proximal opening at a proximal end thereof and a distal needle interface at a distal end thereof;

a stopper member disposed in the injection system body, forming a drug chamber between the stopper member and the distal end of the injection system body;

a plunger member configured to insert the stopper member relative to the injection system body; and a valve forming an openable barrier between the distal needle interface and the drug chamber, the valve comprising an outer member comprising a diaphragm which defines a diaphragm opening therein, and an inner member configured to fit in the diaphragm opening, wherein the inner member is configured to interfere with the diaphragm opening when the diaphragm is in a closed configuration and the inner member is disposed in the diaphragm to form the openable barrier between the distal needle interface and the drug chamber, and wherein the diaphragm is configured to elastically deform into an open configuration with increased pressure in the drug chamber to deform the elastic diaphragm distally away from the stopper member to allow the inner member to separate from the diaphragm to allow flow from the drug chamber to the distal needle interface, wherein the inner member defines an annular groove, and wherein the outer member further comprises a radially inward annular member configured to interfere with the annular groove in the inner member to secure the inner member in the outer member.

17. The system of claim 16, wherein the inner member is made from a metal.

18. The system of claim 16, wherein the inner member comprises a smaller radius portion disposed longitudinally between proximal and distal larger radius portions.

* * * * *